United States Patent
Reiser et al.

(10) Patent No.: US 8,668,927 B2
(45) Date of Patent: Mar. 11, 2014

(54) DYNAMIN MEDIATED DISEASES AND ASSOCIATED METHODS AND PRODUCTS

(75) Inventors: Jochen Reiser, Miami, FL (US); Sanja Sever, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 869 days.

(21) Appl. No.: 12/693,858

(22) Filed: Jan. 26, 2010

(65) Prior Publication Data

US 2010/0221317 A1 Sep. 2, 2010

Related U.S. Application Data

(62) Division of application No. 11/594,003, filed on Nov. 7, 2006, now Pat. No. 7,670,817.

(60) Provisional application No. 60/734,900, filed on Nov. 8, 2005.

(51) Int. Cl.
*A61K 38/55* (2006.01)

(52) U.S. Cl.
USPC ........................................... 424/450

(58) Field of Classification Search
None
See application file for complete search history.

(56) References Cited

U.S. PATENT DOCUMENTS

| 5,883,121 A | 3/1999 | Yamashita et al. |
| 2003/0054984 A1 | 3/2003 | Yong et al. |
| 2003/0166213 A1 | 9/2003 | Greenspan et al. |
| 2004/0253606 A1 | 12/2004 | Aziz et al. |

FOREIGN PATENT DOCUMENTS

| WO | 01/64880 | 9/2001 |
| WO | 02/00878 | 1/2002 |

OTHER PUBLICATIONS

Tuttle et al. (American Journal of Kidney Disease 2003, 42:456-465).*
Ahn et al., "An alternate targeting pathway for procathepsin L in mouse fibroblasts," Traffic (Feb. 2002) 3(2):147-59.
Almeida et al., "Cathepsin B activity regulation. Heparin-like glycosaminogylcans protect human cathepsin B from alkaline pH•induced inactivation," J Biol Chem. (Jan. 12, 2001) 276(2):944-51.
Asamuna et al., "Synaptopodin regulates the actin-bundling activity of alpha-actinin in an isoform-specific manner." J. Clin Invest. (May 2005) 115(5):1188-98.
Attwood, "Genomics. The Babel of bioinformatics," Science (2000) 290:471-473.
Cohen et al., "Quantitative gene expression analysis in renal biopsies: a novel protocol for a high-throughput multicenter application," Kidney Int. (Jan. 2002) 61(1):133-40.

Damke et al., "Induction of mutant dynamin specifically blocks endocytic coated vesicle formation" J Cell Biol. (Nov. 1994) 127(4):915-34.
Damke et al., "Expression, purification, and functional assays for self-association of dynamin-1," Methods Enzymol. (2001) 329:447-57.
Goulet et al., "A novel proteolytically processed CDP/Cux isoform of 90 kDa is generated by cathepsin L" Biol Chem. (Sep. 2006) 387(9):1285-93.
Hsieh et al., "A role for cathepsin L and cathepsin S in peptide generation for MHC class II presentation" J Immunol. (Mar. 15, 2002) 168(6):2618-25.
Ishidoh et al., "Mullti-step processing of procathepsin L in vitro," FEBS Lett. (Oct. 3, 1994) 352(3):281-4.
Kim et al., "Increased expression and apical targeting of renal ENaC subunits in puromycin aminonucleosidc-induced nephrotic syndrome in rats," Am J Physiol Renal Physiol. (May 2004) 286(5):F922-35.
Moeller et al., "Podocyte-specific expression of cre recombinase in transgenic mice," Genesis. (Jan. 2003) 35(1):39-42.
Mundel et al., "Rearrangements of the cytoskeleton and cell contacts induce process formation during differentiation of conditionally immortalized mouse podocyte cell lines," Exp Cell Res. (Oct. 10, 1997) 236(1):248-58.
Nakagawa et al., "Cathepsin L: critical role in li degradation and CD4 T cell selection in the thymus," Science (Apr. 17, 1998) 280(5362):450-3.
Nakamura et al., "Modulation of basement membrane component gene expression in glomeruli of aminonucleoside nephrosis," Lab Invest. (May 1991) 64(5):640-7.
Regele et al., "Glomerular expression of dystroglycans is reduced in minimal change nephrosis but not in focal segmental glomerulosclerosis," J. Am Soc. Nephrol. (Mar. 2000) 11(3):403-12.
Reiser et al., "Podocyte migration during nephrotic syndrome requires a coordinated interplay between cathepsin L and alpha3 intcgrin," J Biol Chem. (Aug. 13, 2004) 279(13):34827-32.
Reiser et. al., "Induction of B7-1 in podocytes is associated with nephrotic syndrome," J Clin Invest. (May 2004) 113 (10):1390-7.
Reiser et. al., "The glomemlar slit diaphragm is a modified adherens junction," J Am Soc Nephrol. (Jan. 2000) 11(1):1-8.
Roth et al., "Cathepsin L deficiency as molecular defect of furless: hyperproliferation of keratinocytes and pertubation of hair follicle cycling," FASEB J. (Oct. 2000) 14(13):2075-86.
Schmid et al., "Gene expression profiles of podocyte-associated molecules as diagnostic markers in acquired proteinuric diseases," J Am Soc Nephrol. (Nov. 2003) 14(11):2958-66.
Schwartz et al., "Podocin, a raft-associated component of the glomerular slit diaphragm, interacts with CD2AP and nephrin," J Clin Invest. (Dec. 2001) 108(11):1621-9.
Skolnick et al., "From genes to protein structure and function: novel applications of computational approaches in the genomic era" Trends in Biotech (2000) 18:34-39.

* cited by examiner

*Primary Examiner* — Sharon Wen

(74) *Attorney, Agent, or Firm* — Brian E. Davy; Bozicevic, Field & Francis LLP

(57) ABSTRACT

This invention relates generally to the treatment of cathepsin or dynamin mediated diseases, such as proteinuria, cancer, and cognitive disease and related products. Diagnostic and other assays are also provided, as well as methods for podocyte cell gene transfer.

4 Claims, 46 Drawing Sheets

Rodent Glomerular Disease Models

Rodent Glomerular Disease Models

Rodent Glomerular Disease Models

Rodent Glomerular Disease Models

Rodent Glomerular Disease Models

Rodent Glomerular Disease Models

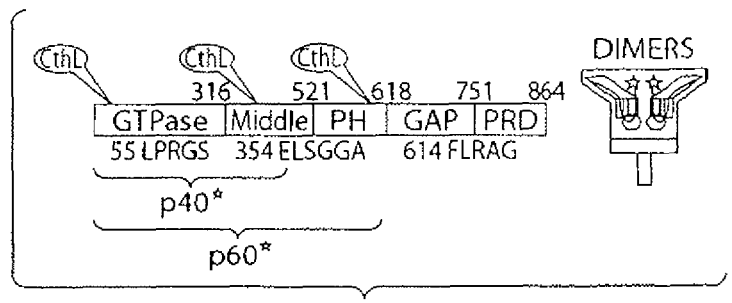

Fig. 4A

```
Dyn1 H. sapiens:      331 QMVQQFAVDFEKRIEGSGDQIDTYELSGGAR INRIFHERFPFE
Dyn2 H. sapiens:      331 QMVQQFGVDFEKRIEGSGDQVDTLELSGGAR INRIFHERFPFE
Dyn1 M. musculus:     331 QMVQQFAVDFEKRIEGSGDQIDTYELSGGAR INRIFHERFPFE
Dyn2 M. musculus:     331 QMVQQFGVDFEKRIEGSGDQVDTLELSGGAR INRIFHERFPFE
Shi  D. melanogaster: 327 LQMIQQLQSDFERTIEGSALVNTNELSGGAK INRIFHERLRFE
Dyn  C. elegans:      334 MVTQFNADIERSIEGSSAKLVSTNELSGGAR INRLFHERFPFE
Vps1 S. cerevisiae:   370 SMIDTFSNEYAGILDGEAKELSSQELSGGAR ISYVFHETFKNG
Dyn1 CthLm:                                           EQSVGA
```

Fig. 4B

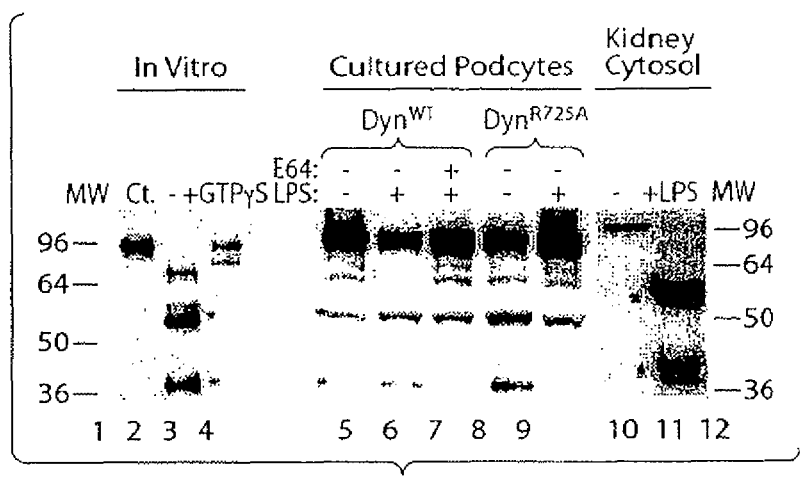

Fig. 4C

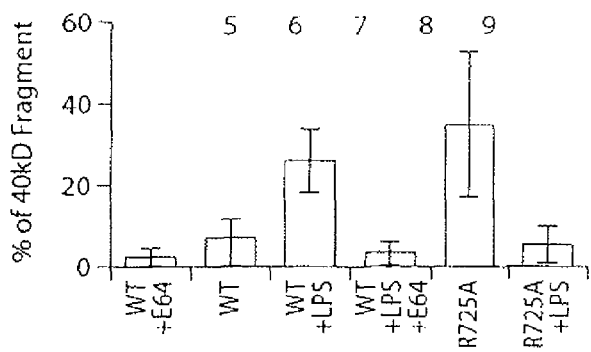 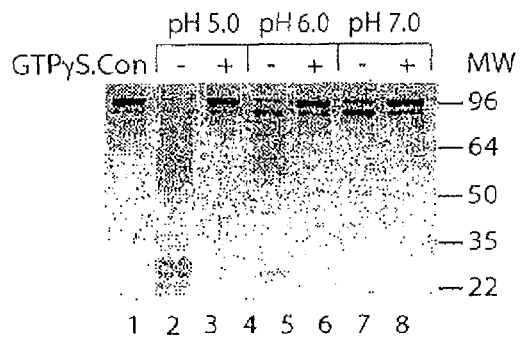
Fig. 4D  Fig. 4E
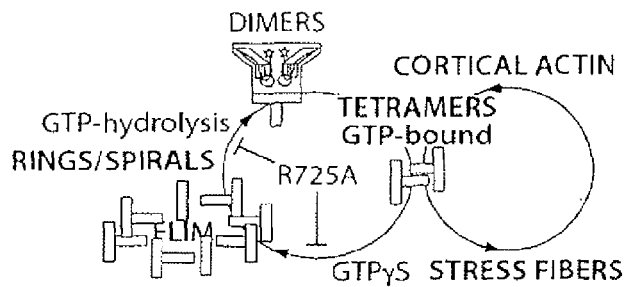
Fig. 4F
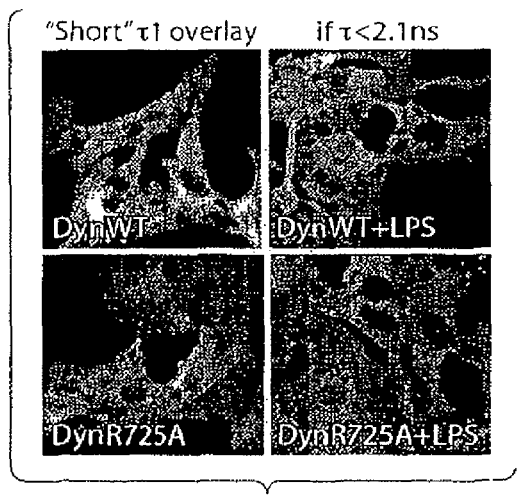
Fig. 4G

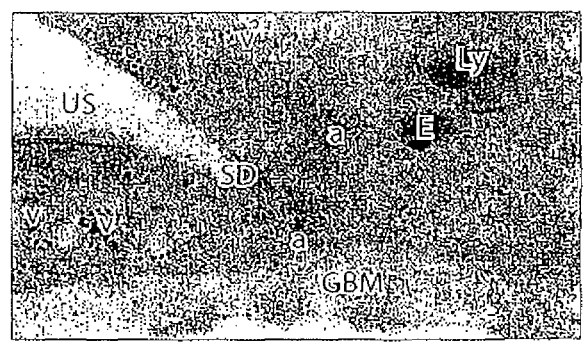
Fig. 18A
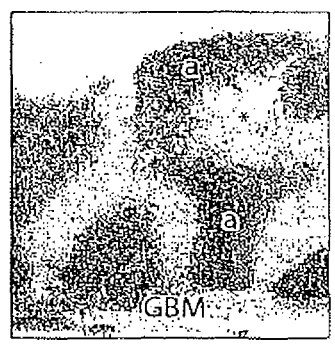
Fig. 18B
  
Fig. 18C        Fig. 18D        Fig. 18E

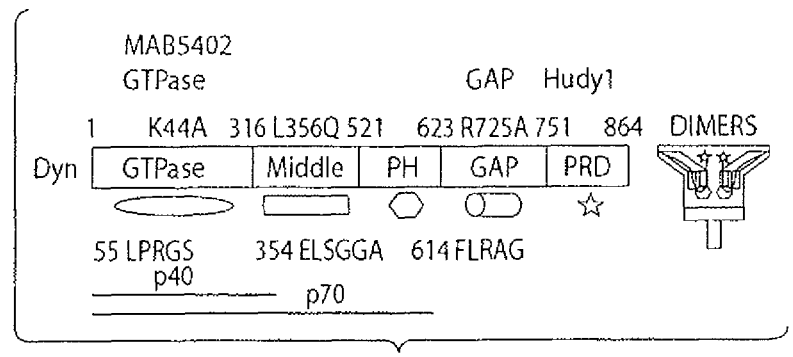

Fig. 19A

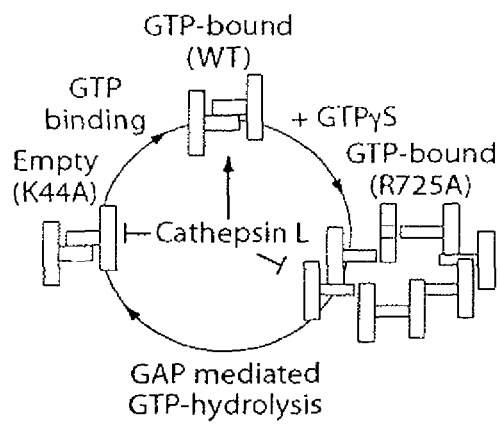

Fig. 19A'

```
Dyn1 H. sapiens:        331 QMVQQFAVDFEKRIEGSGDQIDTYELSGGARINRIFHERFPFE
Dyn2 H. sapiens:        331 QMVQQFGVDFEKRIEGSGDQVDTLELSGGARINRIFHERFPFE
Dyn1 M. musculus:       331 QMVQQFAVDFEKRIEGSGDQIDTYELSGGARINRIFHERFPFE
Dyn2 M. musculus:       331 QMVQQFGVDFEKRIEGSGDQVDTLELSGGARINRIFHERFPFE
Shi  D. melanogaster:   327 LQMIQQLQSDFERTIEGSALVNTNELSGGAKINRIFHERLRFE
Dyn  C. elegans:        334 MVTQFNADIERSIEGSSAKLVSTNELSGGARINRLFHERFPFE
Vps1 S. cerevisiae:     370 SMIDTFSNEYAGILDGEAKELSSQELSGGARISYVFHETFKNG
DynL356Q:                                         EQSVGA
```

Fig. 19B

```
                         SEQUENCE LISTING

<160> NUMBER OF SEQ ID NOS: 32

<210> SEQ ID NO 1
<211> LENGTH: 864
<212> TYPE: PRT
<213> ORGANISM: homo sapiens

<400> SEQUENCE: 1

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Leu Ala Ala Glu Arg
                245                 250                 255

Lys Phe Phe Leu Ser His Pro Ser Tyr Arg His Leu Ala Asp Arg Met
            260                 265                 270

Gly Thr Pro Tyr Leu Gln Lys Val Leu Asn Gln Gln Leu Thr Asn His
        275                 280                 285

Ile Arg Asp Thr Leu Pro Gly Leu Arg Asn Lys Leu Gln Ser Gln Leu
    290                 295                 300

Leu Ser Ile Glu Lys Glu Val Glu Glu Tyr Lys Asn Phe Arg Pro Asp
305                 310                 315                 320
```

```
Asp Pro Ala Arg Lys Thr Lys Ala Leu Leu Gln Met Val Gln Gln Phe
            325                 330                 335

Ala Val Asp Phe Glu Lys Arg Ile Glu Gly Ser Gly Asp Gln Ile Asp
        340                 345                 350

Thr Tyr Glu Leu Ser Gly Gly Ala Arg Ile Asn Arg Ile Phe His Glu
    355                 360                 365

Arg Phe Pro Phe Glu Leu Val Lys Met Glu Phe Asp Glu Lys Glu Leu
    370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
            405                 410                 415

Val Lys Lys Ile Arg Glu Pro Cys Leu Lys Cys Val Asp Met Val Ile
        420                 425                 430

Ser Glu Leu Ile Ser Thr Val Arg Gln Cys Thr Lys Lys Leu Gln Gln
    435                 440                 445

Tyr Pro Arg Leu Arg Glu Glu Met Glu Arg Ile Val Thr Thr His Ile
    450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
            485                 490                 495

Ala Asn Ala Gln Gln Arg Ser Asn Gln Met Asn Lys Lys Lys Thr Ser
        500                 505                 510

Gly Asn Gln Asp Glu Ile Leu Val Ile Arg Lys Gly Trp Leu Thr Ile
    515                 520                 525

Asn Asn Ile Gly Ile Met Lys Gly Gly Ser Lys Glu Tyr Trp Phe Val
    530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
            565                 570                 575

Lys Gly Phe Met Ser Ser Lys His Ile Phe Ala Leu Phe Asn Thr Glu
        580                 585                 590

Gln Arg Asn Val Tyr Lys Asp Tyr Arg Gln Leu Glu Leu Ala Cys Glu
    595                 600                 605

Thr Gln Glu Glu Val Asp Ser Trp Lys Ala Ser Phe Leu Arg Ala Gly
    610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
            645                 650                 655

Arg Gln Val Glu Thr Ile Arg Asn Leu Val Asp Ser Tyr Met Ala Ile
        660                 665                 670

Val Asn Lys Thr Val Arg Asp Leu Met Pro Lys Thr Ile Met His Leu
    675                 680                 685

Met Ile Asn Asn Thr Lys Glu Phe Ile Phe Ser Glu Leu Leu Ala Asn
    690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
            725                 730                 735

Glu Ala Leu Ser Ile Ile Gly Asp Ile Asn Thr Thr Thr Val Ser Thr
        740                 745                 750
```

Pro Met Pro Pro Pro Val Asp Asp Ser Trp Leu Gln Val Gln Ser Val
        755                 760                 765

Pro Ala Gly Arg Arg Ser Pro Thr Ser Ser Pro Thr Pro Gln Arg Arg
    770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
            805                 810                 815

Ser Arg Pro Gly Ala Ser Pro Asp Pro Phe Gly Pro Pro Gln Val
            820                 825                 830

Pro Ser Arg Pro Asn Arg Ala Pro Pro Gly Val Pro Ser Arg Ser Gly
        835                 840                 845

Gln Ala Ser Pro Ser Arg Pro Glu Ser Pro Arg Pro Pro Phe Asp Leu
    850                 855                 860

<210> SEQ ID NO 2
<211> LENGTH: 3216
<212> TYPE: DNA
<213> ORGANISM: homo sapiens

<400> SEQUENCE: 2
gggcgcgcgg ctgcagcggc ggagccggag tcggagccgg agcgctagc ggcagccgga      60 tcgcagcctg cggggcccgc cgcagccatg gcaaccgcg gcatggaaga tctcatcccg     120
ctggtcaacc ggctgcaaga cgccttctct gccatcggcc agaacgcgga cctcgacctg     180
ccgcagatcg ctgtggtggg cggccagagc gccggcaaga gctcggtgct cgagaatttc     240
gtaggcaggg acttcttgcc tcgaggatct ggcattgtca cccgacgtcc cctggtcttg     300
cagctggtca atgcaaccac agaatatgcc gagttcctgc actgcaaggg aaagaaattc     360
accgacttcg aggaggtgcg ccttgagatc gaggccgaga ccgacaggt caccggcacc     420 aacaagggca tctcgccggt gcctatcaac ctccgcgtct actcgccgca cgtgctgaac     480
ctgaccctgg tggacctgcc cggaatgacc aaggtcccgg tggggaccaa acctcccgac     540
atcgagttcc agatccgaga catgcttatg cagtttgtca ccaaggagaa ctgcctcatc     600
ctggccgtgt cccccgccaa ctctgacctg gccaattctg acgccctcaa ggtcgccaag     660
gaggtggacc cccagggcca gcgcaccatc ggggtcatca ccaagctgga cctgatggac     720
gagggcacag atgcccgtga tgtgctggag aacaagctgc tccccctgcg cagaggctac     780
attggagtgg tgaaccggag ccagaaggac attgatggca agaaggacat taccgccgcc     840
ttggctgctg aacgaaagtt cttcctctcc catccatctt atcgccactt ggctgaccgt     900
atgggcacgc cctacctgca gaaggtcctc aatcagcaac tgacgaacca catccgggac     960
acactgccgg gctgcggaa caagctgcag agccagctac tgtccattga aggaggtg    1020 gaggaataca gaacttccg ccctgatgac ccagctcgca agaccaaggc cctgctgcag    1080
atggtccagc agttcgccgt agactttgag aagcgcattg agggctcagg agatcagatc    1140
gacacctacg aactgtcagg gggagcccgc attaaccgaa tcttccacga gcgcttccct    1200
ttcgagctgg tcaagatgga gtttgatgag aaggaactcc gaagggagat cagctatgct    1260
atcaagaata tccatggcat tagaacgggg ctgtttaccc cagacatggc ctttgagacc    1320
attgtgaaaa gcaggtgaa gaagatccga gaaccgtgtc tcaagtgtgt ggacatggtt    1380
atctcggagc taatcagcac cgttagacag tgcaccaaga agctccagca gtacccgcgg    1440
ctacgggagg agatggagcg catcgtgacc acccacatcc gggagcgcga gggccgcact    1500

| | |
|---|---|
| aaggagcagg tcatgcttct catcgatatc gagctggctt acatgaacac caaccatgag | 1560 |
| gacttcatag gctttgccaa tgctcagcag aggagcaacc agatgaacaa gaagaagact | 1620 |
| tcagggaacc aggatgagat tctggtcatc cgcaagggct ggctgactat caataatatt | 1680 |
| ggcatcatga aagggggctc caaggagtac tggtttgtgc tgactgctga gaatctgtcc | 1740 |
| tggtacaagg atgatgagga gaaagagaag aaatacatgc tgtctgtgga caacctcaag | 1800 |
| ctgcgggacg tggagaaggg ctttatgtcg agcaagcata tctttgccct ctttaacacg | 1860 |
| gagcagagga atgtctacaa ggattatcgg cagctggagc tagcctgtga gacacaggag | 1920 |
| gaggtggaca gctggaaggc ctccttcctg agggctggcg tgtaccctga gcgtgttggg | 1980 |
| gacaaagaga agccagcga gaccgaggag aatggctccg acagcttcat gcattccatg | 2040 |
| gacccacagc tggaacggca agtggagacc atccggaatc ttgtggactc atacatggcc | 2100 |
| attgtcaaca agaccgtgag ggacctcatg cccaagacca tcatgcacct catgattaac | 2160 |
| aataccaagg agttcatctt ctcggagctg ctggccaacc tgtactcgtg tggggaccag | 2220 |
| aacacgctga tggaggagtc ggcggagcag gcacagcggc gcgacgagat gctgcgcatg | 2280 |
| taccacgcac tgaaggaggc gctcagcatc atcggcgaca tcaacacgac caccgtcagc | 2340 |
| acgcccatgc ccccgcccgt ggacgactcc tggctgcagg tgcagagcgt accggccgga | 2400 |
| cgcaggtcgc ccacgtccag ccccacgccg cagcgccgag ccccgccgt gccccagcc | 2460 |
| cggcccgggt cgcggggccc tgctcctggg cctccgcctg ctgggtccgc cctgggggggg | 2520 |
| gcgcccccg tgcctccag gccggggggct ccctgacc ctttcggccc tcccctcag | 2580 |
| gtgccctcgc gccccaaccg cgcccgccc ggggtcccca gccgatcggg tcaggcaagt | 2640 |
| ccatcccgtc ctgagagccc caggcccccc ttcgacctct aaacagatcc ctcctcttct | 2700 |
| cggagacctc cctttccaag cctgcctgga cggctgttct gtgacttgac agtggctccc | 2760 |
| ccagccccaa agccagcccc cttcatctgt gacttaatct gttgtagtgg tgagctgata | 2820 |
| cattcaggtg tgaccgttgg tgaaaacttg tgccccttct gtggtatgcc cttgccctgt | 2880 |
| tctataaata tctataaata tcatatatata tacacaccta cacatggcca accgcctcgc | 2940 |
| ctctagcgct gggaatcagt cactgtgcta tccttgtgga gtcttgtggc ccaactacca | 3000 |
| gagaacgctg tccccgaca tcccactcca agtgtgcca cctccagtga gcctccttgt | 3060 |
| catgcccggc ctgtggacag ccagcccccg ccatccctcc cacccctac caagcatggg | 3120 |
| ggtgctgtgc aggcagccgt gtggcctgac agtttctacc agtcctgctg tccctcggct | 3180 |
| gagaataaaa cccatttctg gatgatgggg aatgtc | 3216 |

<210> SEQ ID NO 3
<211> LENGTH: 864
<212> TYPE: PRT
<213> ORGANISM: homo sapiens

<400> SEQUENCE: 3

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                    85                  90                  95

Val Arg Leu Glu Ile Glu Ala Glu Thr Asp Arg Val Thr Gly Thr Asn
                100                 105                 110

Lys Gly Ile Ser Pro Val Pro Ile Asn Leu Arg Val Tyr Ser Pro His
                115                 120                 125

Val Leu Asn Leu Thr Leu Val Asp Leu Pro Gly Met Thr Lys Val Pro
            130                 135                 140

Val Gly Asp Gln Pro Pro Asp Ile Glu Phe Gln Ile Arg Asp Met Leu
145                 150                 155                 160

Met Gln Phe Val Thr Lys Glu Asn Cys Leu Ile Leu Ala Val Ser Pro
                165                 170                 175

Ala Asn Ser Asp Leu Ala Asn Ser Asp Ala Leu Lys Val Ala Lys Glu
            180                 185                 190

Val Asp Pro Gln Gly Gln Arg Thr Ile Gly Val Ile Thr Lys Leu Asp
            195                 200                 205

Leu Met Asp Glu Gly Thr Asp Ala Arg Asp Val Leu Glu Asn Lys Leu
210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Leu Ala Ala Glu Arg
                245                 250                 255

Lys Phe Phe Leu Ser His Pro Ser Tyr Arg His Leu Ala Asp Arg Met
                260                 265                 270

Gly Thr Pro Tyr Leu Gln Lys Val Leu Asn Gln Gln Leu Thr Asn His
            275                 280                 285

Ile Arg Asp Thr Leu Pro Gly Leu Arg Asn Lys Leu Gln Ser Gln Leu
            290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
                340                 345                 350

Thr Tyr Glu Gln Ser Val Gly Ala Arg Ile Asn Arg Ile Phe His Glu
            355                 360                 365

Arg Phe Pro Phe Glu Leu Val Lys Met Glu Phe Asp Glu Lys Glu Leu
370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
                405                 410                 415

Val Lys Lys Ile Arg Glu Pro Cys Leu Lys Cys Val Asp Met Val Ile
                420                 425                 430

Ser Glu Leu Ile Ser Thr Val Arg Gln Cys Thr Lys Lys Leu Gln Gln
            435                 440                 445

Tyr Pro Arg Leu Arg Glu Glu Met Glu Arg Ile Val Thr Thr His Ile
            450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Asn Gln Met Asn Lys Lys Lys Thr Ser

```
                    500                 505                 510
Gly Asn Gln Asp Glu Ile Leu Val Ile Arg Lys Gly Trp Leu Thr Ile
            515                 520                 525

Asn Asn Ile Gly Ile Met Lys Gly Gly Ser Lys Glu Tyr Trp Phe Val
            530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
            565                 570                 575

Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
            595                 600                 605

Thr Gln Glu Glu Val Asp Ser Trp Lys Ala Ser Phe Leu Arg Ala Gly
            610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
            645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
            675                 680                 685

Met Ile Asn Asn Thr Lys Glu Phe Ile Phe Ser Glu Leu Leu Ala Asn
            690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
            725                 730                 735

Glu Ala Leu Ser Ile Ile Gly Asp Ile Asn Thr Thr Thr Val Ser Thr
            740                 745                 750

Pro Met Pro Pro Pro Val Asp Asp Ser Trp Leu Gln Val Gln Ser Val
            755                 760                 765

Pro Ala Gly Arg Arg Ser Pro Thr Ser Ser Pro Thr Pro Gln Arg Arg
            770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
            805                 810                 815

Ser Arg Pro Gly Ala Ser Pro Asp Pro Phe Gly Pro Pro Pro Gln Val
            820                 825                 830

Pro Ser Arg Pro Asn Arg Ala Pro Pro Gly Val Pro Ser Arg Ser Gly
            835                 840                 845

Gln Ala Ser Pro Ser Arg Pro Glu Ser Pro Arg Pro Phe Asp Leu
            850                 855                 860

<210> SEQ ID NO 4
<211> LENGTH: 864
<212> TYPE: PRT
<213> ORGANISM: homo sapiens

<400> SEQUENCE: 4

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
```

```
                20                  25                  30
Gln Ile Ala Val Val Gly Gly Gln Ser Ala Gly Lys Ser Val Leu
            35                  40                  45
Glu Asn Phe Val Gly Arg Asp Phe Leu Pro Arg Gly Ser Gly Ile Val
        50                  55                  60
Thr Arg Arg Pro Leu Val Leu Gln Leu Val Asn Ala Thr Thr Glu Tyr
65                  70                  75                  80
Ala Glu Phe Leu His Cys Lys Gly Lys Lys Phe Thr Asp Phe Glu Glu
                85                  90                  95
Val Arg Leu Glu Ile Glu Ala Glu Thr Asp Arg Val Thr Gly Thr Asn
            100                 105                 110
Lys Gly Ile Ser Pro Val Pro Ile Asn Leu Arg Val Tyr Ser Pro His
            115                 120                 125
Val Leu Asn Leu Thr Leu Val Asp Leu Pro Gly Met Thr Lys Val Pro
        130                 135                 140
Val Gly Asp Gln Pro Pro Asp Ile Glu Phe Gln Ile Arg Asp Met Leu
145                 150                 155                 160
Met Gln Phe Val Thr Lys Glu Asn Cys Leu Ile Leu Ala Val Ser Pro
                165                 170                 175
Ala Asn Ser Asp Leu Ala Asn Ser Asp Ala Leu Lys Val Ala Lys Glu
            180                 185                 190
Val Asp Pro Gln Gly Gln Arg Thr Ile Gly Val Ile Thr Lys Leu Asp
            195                 200                 205
Leu Met Asp Glu Gly Thr Asp Ala Arg Asp Val Leu Glu Asn Lys Leu
        210                 215                 220
Leu Pro Leu Arg Arg Gly Tyr Ile Gly Val Val Asn Arg Ser Gln Lys
225                 230                 235                 240
Asp Ile Asp Gly Lys Lys Asp Ile Thr Ala Ala Leu Ala Ala Glu Arg
                245                 250                 255
Lys Phe Phe Leu Ser His Pro Ser Tyr Arg His Leu Ala Asp Arg Met
            260                 265                 270
Gly Thr Pro Tyr Leu Gln Lys Val Leu Asn Gln Gln Leu Thr Asn His
            275                 280                 285
Ile Arg Asp Thr Leu Pro Gly Leu Arg Asn Lys Leu Gln Ser Gln Leu
        290                 295                 300
Leu Ser Ile Glu Lys Glu Val Glu Glu Tyr Lys Asn Phe Arg Pro Asp
305                 310                 315                 320
Asp Pro Ala Arg Lys Thr Lys Ala Leu Leu Gln Met Val Gln Gln Phe
                325                 330                 335
Ala Val Asp Phe Glu Lys Arg Ile Glu Gly Ser Gly Asp Gln Ile Asp
            340                 345                 350
Thr Tyr Glu Leu Ser Gly Gly Ala Arg Ile Asn Arg Ile Phe His Glu
            355                 360                 365
Arg Phe Pro Phe Glu Leu Val Lys Met Glu Phe Asp Glu Lys Glu Leu
        370                 375                 380
Arg Arg Glu Ile Ser Tyr Ala Ile Lys Asn Ile His Gly Ile Arg Thr
385                 390                 395                 400
Gly Leu Phe Thr Pro Asp Met Ala Phe Glu Thr Ile Val Lys Lys Gln
                405                 410                 415
Val Lys Lys Ile Arg Glu Pro Cys Leu Lys Cys Val Asp Met Val Ile
            420                 425                 430
Ser Glu Leu Ile Ser Thr Val Arg Gln Cys Thr Lys Lys Leu Gln Gln
        435                 440                 445
```

```
Tyr Pro Arg Leu Arg Glu Glu Met Glu Arg Ile Val Thr His Ile
450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Asn Gln Met Asn Lys Lys Thr Ser
            500                 505                 510

Gly Asn Gln Asp Glu Ile Leu Val Ile Arg Lys Gly Trp Leu Thr Ile
        515                 520                 525

Asn Asn Ile Gly Ile Met Lys Gly Gly Ser Lys Glu Tyr Trp Phe Val
530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
                565                 570                 575

Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
        595                 600                 605

Thr Gln Glu Glu Val Asp Ser Trp Lys Ala Ser Phe Leu Arg Ala Gly
610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
        675                 680                 685

Met Ile Asn Asn Thr Lys Glu Phe Ile Phe Ser Glu Leu Leu Ala Asn
690                 695                 700

Leu Tyr Ser Cys Gly Asp Gln Asn Thr Leu Met Glu Glu Ser Ala Glu
705                 710                 715                 720

Gln Ala Gln Arg Ala Asp Glu Met Leu Arg Met Tyr His Ala Leu Lys
                725                 730                 735

Glu Ala Leu Ser Ile Ile Gly Asp Ile Asn Thr Thr Val Ser Thr
            740                 745                 750

Pro Met Pro Pro Pro Val Asp Asp Ser Trp Leu Gln Val Gln Ser Val
                755                 760                 765

Pro Ala Gly Arg Arg Ser Pro Thr Ser Ser Pro Thr Pro Gln Arg Arg
770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Gln Val
            820                 825                 830

Pro Ser Arg Pro Asn Arg Ala Pro Pro Gly Val Pro Ser Arg Ser Gly
        835                 840                 845

Gln Ala Ser Pro Ser Arg Pro Glu Ser Pro Arg Pro Pro Phe Asp Leu
850                 855                 860
```

<210> SEQ ID NO 5

```
<211> LENGTH: 864
<212> TYPE: PRT
<213> ORGANISM: homo sapiens

<400> SEQUENCE: 5
```

| | | | | | | | | | | | | | | | |
|---|---|---|---|---|---|---|---|---|---|---|---|---|---|---|---|
| Met | Gly | Asn | Arg | Gly | Met | Glu | Asp | Leu | Ile | Pro | Leu | Val | Asn | Arg | Leu |
| 1 | | | | 5 | | | | | 10 | | | | | 15 | |
| Gln | Asp | Ala | Phe | Ser | Ala | Ile | Gly | Gln | Asn | Ala | Asp | Leu | Asp | Leu | Pro |
| | | | 20 | | | | | 25 | | | | | 30 | | |
| Gln | Ile | Ala | Val | Val | Gly | Gly | Gln | Ser | Ala | Gly | Lys | Ser | Ser | Val | Leu |
| | | 35 | | | | | 40 | | | | | 45 | | | |
| Glu | Asn | Phe | Val | Gly | Arg | Asp | Phe | Leu | Pro | Arg | Gly | Ser | Gly | Ile | Val |
| 50 | | | | | 55 | | | | | 60 | | | | | |
| Thr | Arg | Arg | Pro | Leu | Val | Leu | Gln | Leu | Val | Asn | Ala | Thr | Thr | Glu | Tyr |
| 65 | | | | 70 | | | | | 75 | | | | | 80 | |
| Ala | Glu | Phe | Leu | His | Cys | Lys | Gly | Lys | Lys | Phe | Thr | Asp | Phe | Glu | Glu |
| | | | | 85 | | | | | 90 | | | | | 95 | |
| Val | Arg | Leu | Glu | Ile | Glu | Ala | Glu | Thr | Asp | Arg | Val | Thr | Gly | Thr | Asn |
| | | | 100 | | | | | 105 | | | | | 110 | | |
| Lys | Gly | Ile | Ser | Pro | Val | Pro | Ile | Asn | Leu | Arg | Val | Tyr | Ser | Pro | His |
| | | 115 | | | | | 120 | | | | | 125 | | | |
| Val | Leu | Asn | Leu | Thr | Leu | Val | Asp | Leu | Pro | Gly | Met | Thr | Lys | Val | Pro |
| 130 | | | | | 135 | | | | | 140 | | | | | |
| Val | Gly | Asp | Gln | Pro | Pro | Asp | Ile | Glu | Phe | Gln | Ile | Arg | Asp | Met | Leu |
| 145 | | | | 150 | | | | | 155 | | | | | 160 | |
| Met | Gln | Phe | Val | Thr | Lys | Glu | Asn | Cys | Leu | Ile | Leu | Ala | Val | Ser | Pro |
| | | | | 165 | | | | | 170 | | | | | 175 | |
| Ala | Asn | Ser | Asp | Leu | Ala | Asn | Ser | Asp | Ala | Leu | Lys | Val | Ala | Lys | Glu |
| | | | 180 | | | | | 185 | | | | | 190 | | |
| Val | Asp | Pro | Gln | Gly | Gln | Arg | Thr | Ile | Gly | Val | Ile | Thr | Lys | Leu | Asp |
| | | 195 | | | | | 200 | | | | | 205 | | | |
| Leu | Met | Asp | Glu | Gly | Thr | Asp | Ala | Arg | Asp | Val | Leu | Glu | Asn | Lys | Leu |
| 210 | | | | | 215 | | | | | 220 | | | | | |
| Leu | Pro | Leu | Arg | Arg | Gly | Tyr | Ile | Gly | Val | Val | Asn | Arg | Ser | Gln | Lys |
| 225 | | | | | 230 | | | | | 235 | | | | | 240 |
| Asp | Ile | Asp | Gly | Lys | Lys | Asp | Ile | Thr | Ala | Ala | Leu | Ala | Ala | Glu | Arg |
| | | | | 245 | | | | | 250 | | | | | 255 | |
| Lys | Phe | Phe | Leu | Ser | His | Pro | Ser | Tyr | Arg | His | Leu | Ala | Asp | Arg | Met |
| | | | 260 | | | | | 265 | | | | | 270 | | |
| Gly | Thr | Pro | Tyr | Leu | Gln | Lys | Val | Leu | Asn | Gln | Leu | Thr | Asn | His | |
| | | | 275 | | | | | 280 | | | | | 285 | | |
| Ile | Arg | Asp | Thr | Leu | Pro | Gly | Leu | Arg | Asn | Lys | Leu | Gln | Ser | Gln | Leu |
| | | 290 | | | | | 295 | | | | | 300 | | | |
| Leu | Ser | Ile | Glu | Lys | Glu | Val | Glu | Tyr | Lys | Asn | Phe | Arg | Pro | Asp | |
| 305 | | | | | 310 | | | | | 315 | | | | | 320 |
| Asp | Pro | Ala | Arg | Lys | Thr | Lys | Ala | Leu | Leu | Gln | Met | Val | Gln | Gln | Phe |
| | | | | 325 | | | | | 330 | | | | | 335 | |
| Ala | Val | Asp | Phe | Glu | Lys | Arg | Ile | Glu | Gly | Ser | Gly | Asp | Gln | Ile | Asp |
| | | | 340 | | | | | 345 | | | | | 350 | | |
| Thr | Tyr | Glu | Leu | Ser | Gly | Gly | Ala | Arg | Ile | Asn | Arg | Ile | Phe | His | Glu |
| | | 355 | | | | | 360 | | | | | 365 | | | |
| Arg | Phe | Pro | Phe | Glu | Leu | Val | Lys | Met | Glu | Phe | Asp | Glu | Lys | Glu | Leu |
| 370 | | | | | 375 | | | | | 380 | | | | | |
| Arg | Arg | Glu | Ile | Ser | Tyr | Ala | Ile | Lys | Asn | Ile | His | Gly | Ile | Arg | Thr |
| 385 | | | | | 390 | | | | | 395 | | | | | 400 |

```
Gly Leu Phe Thr Pro Asp Met Ala Phe Glu Thr Ile Val Lys Lys Gln
                405                 410                 415

Val Lys Lys Ile Arg Glu Pro Cys Leu Lys Cys Val Asp Met Val Ile
            420                 425                 430

Ser Glu Leu Ile Ser Thr Val Arg Gln Cys Thr Lys Lys Leu Gln Gln
            435                 440                 445

Tyr Pro Arg Leu Arg Glu Glu Met Glu Arg Ile Val Thr Thr His Ile
    450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Asn Gln Met Asn Lys Lys Lys Thr Ser
            500                 505                 510

Gly Asn Gln Asp Glu Ile Leu Val Ile Arg Lys Gly Trp Leu Thr Ile
            515                 520                 525

Asn Asn Ile Gly Ile Met Lys Gly Gly Ser Lys Glu Tyr Trp Phe Val
    530                 535                 540

Leu Thr Ala Glu Asn Leu Ser Trp Tyr Lys Asp Glu Glu Lys Glu
545                 550                 555                 560

Lys Lys Tyr Met Leu Ser Val Asp Asn Leu Lys Leu Arg Asp Val Glu
                565                 570                 575

Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
            595                 600                 605

Thr Gln Glu Glu Val Asp Ser Trp Lys Ala Ser Phe Leu Arg Ala Gly
    610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
            675                 680                 685

Met Ile Asn Asn Thr Lys Glu Phe Ile Phe Ser Glu Leu Leu Ala Asn
    690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asn Ile Asn Thr Thr Thr Val Ser Thr
            740                 745                 750

Pro Met Pro Pro Pro Val Asp Asp Ser Trp Leu Gln Val Gln Ser Val
            755                 760                 765

Pro Ala Gly Arg Arg Ser Pro Thr Ser Ser Pro Thr Pro Gln Arg Arg
    770                 775                 780

Ala Pro Ala Val Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Pro Gln Val
```

```
               820               825                 830
Pro Ser Arg Pro Asn Arg Ala Pro Pro Gly Val Pro Ser Arg Ser Gly
        835                 840                 845

Gln Ala Ser Pro Ser Arg Pro Glu Ser Pro Arg Pro Pro Phe Asp Leu
    850                 855                 860
```

<210> SEQ ID NO 6
<211> LENGTH: 3187
<212> TYPE: DNA
<213> ORGANISM: homo sapiens

<400> SEQUENCE: 6

| | | | | | |
|---|---|---|---|---|---|
| cgcccggagt | cggagccggg | agcgctagcg | gcagccggat | cgcagcctgc | ggggcccgcc | 60 |
| gcagccatgg | gcaaccgcgg | catggaagat | ctcatcccgc | tggtcaaccg | gctgcaagac | 120 |
| gccttctctg | ccatcggcca | gaacgcggac | ctcgacctgc | cgcagatcgc | tgtggtgggc | 180 |
| ggccagagcg | ccggcaagag | ctcggtgctc | gagaatttcg | taggcaggga | cttcttgcct | 240 |
| cgaggatctg | gcattgtcac | ccgacgtccc | ctggtcttgc | agctggtcaa | tgcaaccaca | 300 |
| gaatatgccg | agttcctgca | ctgcaaggga | agaaaattca | ccgacttcga | ggaggtgcgc | 360 |
| cttgagatcg | aggccgagac | cgacagggtc | accggcacca | caagggcat | ctcgccggtg | 420 |
| cctatcaacc | tccgcgtcta | ctcgccgcac | gtgctgaacc | tgaccctggt | ggacctgccc | 480 |
| ggaatgacca | aggtcccggt | gggggaccaa | cctcccgaca | tcgagttcca | gatccgagac | 540 |
| atgcttatgc | agtttgtcac | caaggagaac | tgcctcatcc | tggccgtgtc | ccccgccaac | 600 |
| tctgacctgg | ccaattctga | cgccctcaag | gtcgccaagg | aggtggaccc | ccagggccag | 660 |
| cgcaccatcg | ggtcatcac | caagctggac | ctgatggacg | agggcacaga | tgcccgtgat | 720 |
| gtgctggaga | caagctgct | cccctgcgc | agaggctaca | ttggagtggt | gaaccggagc | 780 |
| cagaaggaca | ttgatggcaa | gaaggacatt | accgccgcct | ggctgctgaa | cgaaagttc | 840 |
| ttcctctccc | atccatctta | tcgccacttg | gctgaccgta | tgggcacgcc | ctacctgcag | 900 |
| aaggtcctca | atcagcaact | gacgaaccac | atccgggaca | cactgccggg | gctgcgaaac | 960 |
| aagctgcaga | gccagctact | gtccattgag | aaggaggtgg | aggaatacaa | gaacttccgc | 1020 |
| cctgatgacc | cagctcgcaa | gaccaaggcc | ctgctgcaga | tggtccagca | gtttgccgta | 1080 |
| gactttgaga | gcgcattga | gggctcagga | gatcagatcg | acacctacga | actgtcaggg | 1140 |
| ggagcccgca | ttaaccgaat | cttccacgag | cgcttccctt | tcgagctggt | caagatggag | 1200 |
| tttgatgaga | ggaactccg | aagggagatc | agctatgcta | tcaagaatat | ccatggcatt | 1260 |
| agaacggggc | tgtttacccc | agacatggcc | tttgagacca | ttgtgaaaa | gcaggtgaag | 1320 |
| aagatccgag | aaccgtgtct | caagtgtgtg | gacatggtta | tctcggagct | aatcagcacc | 1380 |
| gttagacagt | gcaccaagaa | gctccagcag | tacccgcggc | tacgggagga | gatggagcgc | 1440 |
| atcgtgacca | cccacatccg | ggagcgcgag | ggccgcacta | aggagcaggt | catgcttctc | 1500 |
| atcgatatcg | agctggctta | catgaacacc | aaccatgagg | acttcatagg | ctttgccaat | 1560 |
| gctcagcaga | ggagcaacca | gatgaacaag | aagaagactt | cagggaacca | ggatgagatt | 1620 |
| ctggtcatcc | gcaagggctg | gctgactatc | aataatattg | gcatcatgaa | aggggctcc | 1680 |
| aaggagtact | ggtttgtgct | gactgctgag | aatctgtcct | ggtacaagga | tgatgaggag | 1740 |
| aaagagaaga | aatacatgct | gtctgtggac | aacctcaagc | tgcgggacgt | ggagaagggc | 1800 |
| tttatgtcga | gcaagcatat | cttttgccctc | tttaacacgg | agcagaggaa | tgtctacaag | 1860 |
| gattatcggc | agctggagct | agcctgtgag | acacaggagg | aggtggacag | ctggaaggcc | 1920 |

```
tccttcctga gggctggcgt gtaccctgag cgtgttgggg acaaagagaa agccagcgag    1980
accgaggaga atggctccga cagcttcatg cattccatgg acccacagct ggaacggcaa    2040
gtggagacca tccggaatct tgtggactca tacatggcca ttgtcaacaa gaccgtgagg    2100
gacctcatgc ccaagaccat catgcacctc atgattaaca ataccaagga gttcatcttc    2160
tcggagctgc tggccaacct gtactcgtgt ggggaccaga acacgctgat ggaggagtcg    2220
gcggagcagg cacagcggcg cgacgagatg ctgcgcatgt accacgcact gaaggaggcg    2280
ctcagcatca tcggcaacat caacacgacc accgtcagca cgcccatgcc cccgcccgtg    2340
gacgactcct ggctgcaggt gcagagcgta ccggccggac gcaggtcgcc cacgtccagc    2400
cccacgccgc agcgccgagc ccccgccgtg cccccagccc ggcccgggtc gcggggccct    2460
gctcctgggc ctccgcctgc tgggtccgcc ctggggggg cgcccccgt gcctccagg    2520
ccggggcttt ccctgaccc tttcggccct cccctcagg tgccctcgcg ccccaaccgc    2580
gccccgcccg ggtccccag ccgatcgggt caggcaagtc catcccgtcc tgagagcccc    2640
aggcccccct tcgacctcta aacagatccc tcctcttctc ggagacctcc ctttccaagc    2700
ctgcctggac ggctgttctg tgacttgaca gtggctcccc cagccccaaa gccagccccc    2760
ttcatctgtg acttaatctg ttgtagtggt gagctgatac attcaggtgt gaccgttggt    2820
gaaaacttgt gccccttctg tggtatgccc ttgccctgtt ctataaatat ctataaatac    2880
tcatatatat acacacctac acatggccaa ccgcctcgcc tctagcgctg ggaatcagtc    2940
actgtgctat ccttgtggag tcttgtggcc caactaccag agaacgctgt ccccgacat    3000
cccactccaa agtgtgccac ctccagtgag cctccttgtc atgcccggcc tgtggacagc    3060
cagcccccgc catccctccc accccctacc aagcatgggg gtgctgtgca ggcagccgtg    3120
tggcctgaca gtttctacca gtcctgctgt ccctcggctg agaataaaac ccatttctgg    3180
atgatgg                                                              3187
```

<210> SEQ ID NO 7
<211> LENGTH: 864
<212> TYPE: PRT
<213> ORGANISM: homo sapiens

<400> SEQUENCE: 7

Met Gly Asn Arg Gly Met Glu Asp Leu Ile Pro Leu Val Asn Arg Leu
1               5                   10                  15

Gln Asp Ala Phe Ser Ala Ile Gly Gln Asn Ala Asp Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Val Leu Gln Leu Val Asn Ala Thr Thr Glu Tyr
65                  70                  75                  80

Ala Glu Phe Leu His Cys Lys Gly Lys Lys Phe Thr Asp Phe Glu Glu
                85                  90                  95

Val Arg Leu Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Val Asp Leu Pro Gly Met Thr Lys Val Pro
    130                 135                 140

Val Gly Asp Gln Pro Pro Asp Ile Glu Phe Gln Ile Arg Asp Met Leu

```
                145                 150                 155                 160
Met Gln Phe Val Thr Lys Glu Asn Cys Leu Ile Leu Ala Val Ser Pro
                    165                 170                 175

Ala Asn Ser Asp Leu Ala Asn Ser Asp Ala Leu Lys Val Ala Lys Glu
                180                 185                 190

Val Asp Pro Gln Gly Gln Arg Thr Ile Gly Val Ile Thr Lys Leu Asp
            195                 200                 205

Leu Met Asp Glu Gly Thr Asp Ala Arg Asp Val Leu Glu Asn Lys Leu
        210                 215                 220

Leu Pro Leu Arg Arg Gly Tyr Ile Gly Val Val Asn Arg Ser Gln Lys
225                 230                 235                 240

Asp Ile Asp Gly Lys Lys Asp Ile Thr Ala Ala Leu Ala Ala Glu Arg
                245                 250                 255

Lys Phe Phe Leu Ser His Pro Ser Tyr Arg His Leu Ala Asp Arg Met
                260                 265                 270

Gly Thr Pro Tyr Leu Gln Lys Val Leu Asn Gln Gln Leu Thr Asn His
            275                 280                 285

Ile Arg Asp Thr Leu Pro Gly Leu Arg Asn Lys Leu Gln Ser Gln Leu
        290                 295                 300

Leu Ser Ile Glu Lys Glu Val Glu Glu Tyr Lys Asn Phe Arg Pro Asp
305                 310                 315                 320

Asp Pro Ala Arg Lys Thr Lys Ala Leu Leu Gln Met Val Gln Gln Phe
                325                 330                 335

Ala Val Asp Phe Glu Lys Arg Ile Glu Gly Ser Gly Asp Gln Ile Asp
                340                 345                 350

Thr Tyr Glu Leu Ser Gly Gly Ala Arg Ile Asn Arg Ile Phe His Glu
            355                 360                 365

Arg Phe Pro Phe Glu Leu Val Lys Met Glu Phe Asp Glu Lys Glu Leu
        370                 375                 380

Arg Arg Glu Ile Ser Tyr Ala Ile Lys Asn Ile His Gly Ile Arg Thr
385                 390                 395                 400

Gly Leu Phe Thr Pro Asp Met Ala Phe Glu Thr Ile Val Lys Lys Gln
                405                 410                 415

Val Lys Lys Ile Arg Glu Pro Cys Leu Lys Cys Val Asp Met Val Ile
                420                 425                 430

Ser Glu Leu Ile Ser Thr Val Arg Gln Cys Thr Lys Lys Leu Gln Gln
            435                 440                 445

Tyr Pro Arg Leu Arg Glu Glu Met Glu Arg Ile Val Thr Thr His Ile
        450                 455                 460

Arg Glu Arg Glu Gly Arg Thr Lys Glu Gln Val Met Leu Leu Ile Asp
465                 470                 475                 480

Ile Glu Leu Ala Tyr Met Asn Thr Asn His Glu Asp Phe Ile Gly Phe
                485                 490                 495

Ala Asn Ala Gln Gln Arg Ser Asn Gln Met Asn Lys Lys Lys Thr Ser
                500                 505                 510

Gly Asn Gln Asp Glu Ile Leu Val Ile Arg Lys Gly Trp Leu Thr Ile
            515                 520                 525

Asn Asn Ile Gly Ile Met Lys Gly Gly Ser Lys Glu Tyr Trp Phe Val
        530                 535                 540

Leu Thr Ala Glu Asn Leu Ser Trp Tyr Lys Asp Asp Glu Glu Lys Glu
545                 550                 555                 560

Lys Lys Tyr Met Leu Ser Val Asp Asn Leu Lys Leu Arg Asp Val Glu
                565                 570                 575
```

```
Lys Gly Phe Met Ser Ser Lys His Ile Phe Ala Leu Phe Asn Thr Glu
            580                 585                 590

Gln Arg Asn Val Tyr Lys Asp Tyr Arg Gln Leu Glu Leu Ala Cys Glu
        595                 600                 605

Thr Gln Glu Glu Val Asp Ser Trp Lys Ala Ser Phe Leu Arg Ala Gly
    610                 615                 620

Val Tyr Pro Glu Arg Val Gly Asp Lys Glu Lys Ala Ser Glu Thr Glu
625                 630                 635                 640

Glu Asn Gly Ser Asp Ser Phe Met His Ser Met Asp Pro Gln Leu Glu
                645                 650                 655

Arg Gln Val Glu Thr Ile Arg Asn Leu Val Asp Ser Tyr Met Ala Ile
            660                 665                 670

Val Asn Lys Thr Val Arg Asp Leu Met Pro Lys Thr Ile Met His Leu
        675                 680                 685

Met Ile Asn Asn Thr Lys Glu Phe Ile Phe Ser Glu Leu Leu Ala Asn
    690                 695                 700

Leu Tyr Ser Cys Gly Asp Gln Asn Thr Leu Met Glu Glu Ser Ala Glu
705                 710                 715                 720

Gln Ala Gln Arg Arg Asp Glu Met Leu Arg Met Tyr His Ala Leu Lys
                725                 730                 735

Glu Ala Leu Ser Ile Ile Gly Asn Ile Asn Thr Thr Thr Val Ser Thr
            740                 745                 750

Pro Met Pro Pro Val Asp Asp Ser Trp Leu Gln Val Gln Ser Val
        755                 760                 765

Pro Ala Gly Arg Arg Ser Pro Thr Ser Ser Pro Thr Pro Gln Arg Arg
    770                 775                 780

Ala Pro Ala Val Pro Pro Ala Arg Pro Gly Ser Arg Gly Pro Ala Pro
785                 790                 795                 800

Gly Pro Pro Pro Ala Gly Ser Ala Leu Gly Gly Ala Pro Pro Val Pro
                805                 810                 815

Ser Arg Pro Gly Ala Ser Pro Asp Pro Phe Gly Pro Pro Gln Val
            820                 825                 830

Pro Ser Arg Pro Asn Arg Ala Pro Pro Gly Val Pro Ser Arg Ser Gly
        835                 840                 845

Gln Ala Ser Pro Ser Arg Pro Glu Ser Pro Arg Pro Pro Phe Asp Leu
850                 855                 860

<210> SEQ ID NO 8
<211> LENGTH: 240
<212> TYPE: DNA
<213> ORGANISM: homo sapiens

<400> SEQUENCE: 8
gagatcagct atgctatcaa gaatatccat ggcattagga cgggcctctt cacacctgac      60
ctcgcttttg aagccacagt gaaaaagcag gtgcagaagc tcaaagagcc cagtatcaag     120
tgtgtggata tggtagtcag tgagctcaca gccaccatca gaaagtgtag cgaaaagctc     180
cagcagtacc cgcggctacg ggaggagatg gagcgcatcg tgaccaccca catccgggag     240

<210> SEQ ID NO 9
<211> LENGTH: 80
<212> TYPE: PRT
<213> ORGANISM: homo sapiens

<400> SEQUENCE: 9

Glu Ile Ser Tyr Ala Ile Lys Asn Ile His Gly Ile Arg Thr Gly Leu
1               5                   10                  15
```

Phe Thr Pro Asp Leu Ala Phe Glu Ala Thr Val Lys Lys Gln Val Gln
            20                  25                  30

Lys Leu Lys Glu Pro Ser Ile Lys Cys Val Asp Met Val Val Ser Glu
        35                  40                  45

Leu Thr Ala Thr Ile Arg Lys Cys Ser Glu Lys Leu Gln Gln Tyr Pro
    50                  55                  60

Arg Leu Arg Glu Glu Met Glu Arg Ile Val Thr Thr His Ile Arg Glu
65                  70                  75                  80

<210> SEQ ID NO 10
<211> LENGTH: 950
<212> TYPE: DNA
<213> ORGANISM: homo sapiens

<400> SEQUENCE: 10
gacgagatgc tgcgcatgta ccacgcactg aaggaggcgc tcagcatcat cggcaacatc      60
aacacgacca ccgtcagcac gcccatgccc ccgcccgtgg acgactcctg gctgcaggtg     120
cagagcgtac cggccggacg caggtcgccc acgtccagcc ccacgccgca cgccgagcc     180 cccgccgtgc cccagcccg gcccgggtcg cggggccctg ctcctgggcc tccgcctgct     240
gggtccgccc tggggggggc gcccccgtg ccctccaggc gggggcttc ccctgaccct     300 ttcggccctc cccctcaggt gccctcgcgc ccaaccgcg cccgccggg gtccccagc     360 cagccgatcg ggtcaggcaa gtccatcccg tcctgagagc cccaggcccc ccttcgacct     420
ctaaacagat ccctcctctt tcggagacc tcccttccca gcctgcctg acggctgtt     480 ctgtgacttg acagtggctc ccccagcccc aaagccagcc cccttcatct gtgacttaat     540
ctgttgtagt ggtgagctga tacattcagg tgtgaccgtt ggtgaaaact tgtgcccctt     600
ctgtggtatg cccttgccct gttctataaa tatctataaa tactcatata tatacacacc     660
tacacatggc caaccgcctc gcctctagcg ctgggaatca gtcactgtgc tatccttgtg     720
gagtcttgtg gcccaactac cagagaacgc tgtccccga catcccactc caaagtgtgc     780
cacctccagt gagcctcctt gtcatgcccg gcctgtggac agccagcccc cgccatccct     840
cccaccccct accaagcatg ggggtgctgt gcaggcagcc gtgtggcctg acagtttcta     900
ccagtcctgc tgtccctcgg ctgagaataa aacccatttc tggatgatgg                950

<210> SEQ ID NO 11
<211> LENGTH: 131
<212> TYPE: PRT
<213> ORGANISM: homo sapiens

<400> SEQUENCE: 11

Asp Glu Met Leu Arg Met Tyr His Ala Leu Lys Glu Ala Leu Ser Ile
1               5                   10                  15

Ile Gly Asn Ile Asn Thr Thr Thr Val Ser Thr Pro Met Pro Pro Pro
            20                  25                  30

Val Asp Asp Ser Trp Leu Gln Val Gln Ser Val Pro Ala Gly Arg Arg
        35                  40                  45

Ser Pro Thr Ser Ser Pro Thr Pro Gln Arg Arg Ala Pro Ala Val Pro
    50                  55                  60

Pro Ala Arg Pro Gly Ser Arg Gly Pro Ala Gly Pro Pro Pro Ala
65                  70                  75                  80

Gly Ser Ala Leu Gly Gly Ala Pro Pro Val Pro Ser Arg Pro Gly Ala
                85                  90                  95

Ser Pro Asp Pro Phe Gly Pro Pro Pro Gln Val Pro Ser Arg Pro Asn

Arg Ala Pro Pro Gly Val Pro Ser Gln Pro Ile Gly Ser Gly Lys Ser
        115                 120                 125

Ile Pro Ser
    130

<210> SEQ ID NO 12
<211> LENGTH: 983
<212> TYPE: DNA
<213> ORGANISM: homo sapiens

<400> SEQUENCE: 12
gacgagatgc tgcgcatgta ccacgcactg aaggaggcgc tcagcatcat cggcaacatc      60
aacacgacca ccgtcagcac gcccatgccc ccgcccgtgg acgactcctg gctgcaggtg     120
cagagcgtac cggccggacg caggtcgccc acgtccagcc ccacgccgca gcgccgagcc     180
cccgccgtgc ccccagcccg gcccgggtcg cggggccctg ctcctgggcc tccgcctgct     240
gggtccgccc tggggggggc gccccccgtg ccctccaggc cgggggcttc ccctgaccct     300
ttcggccctc cccctcaggt gccctcgcgc ccaaccgcg cccgcccgg gtcccaga       360 atcactatca gtgaccctg aggagcgtca gccatgccga tcgggtcagg caagtccatc      420
ccgtcctgag agccccaggc cccccttcga cctctaaaca gatccctcct cttctcggag     480
acctcccttt ccaagcctgc ctggacggct gttctgtgac ttgacagtgg ctccccagc     540 cccaaagcca gccccttca tctgtgactt aatctgttgt agtggtgagc tgatacattc     600
aggtgtgacc gttggtgaaa acttgtgccc cttctgtggt atgcccttgc cctgttctat     660
aaatatctat aaatactcat atatatacac acctacacat ggccaaccgc ctcgcctcta     720
gcgctgggaa tcagtcactg tgctatcctt gtggagtctt gtggcccaac taccagaaa     780 cgctgtcccc cgacatccca ctccaaagtg tgccacctcc agtgagcctc cttgtcatgc     840
ccggcctgtg gacagccagc cccgccatc cctcccaccc cctaccaagc atggggtgc      900 tgtgcaggca gccgtgtggc ctgacagttt ctaccagtcc tgctgtccct cggctgagaa     960
taaaacccat ttctggatga tgg                                             983

<210> SEQ ID NO 13
<211> LENGTH: 126
<212> TYPE: PRT
<213> ORGANISM: homo sapiens

<400> SEQUENCE: 13

Asp Glu Met Leu Arg Met Tyr His Ala Leu Lys Glu Ala Leu Ser Ile
1               5                   10                  15

Ile Gly Asn Ile Asn Thr Thr Thr Val Ser Thr Pro Met Pro Pro
            20                  25                  30

Val Asp Asp Ser Trp Leu Gln Val Gln Ser Val Pro Ala Gly Arg Arg
        35                  40                  45

Ser Pro Thr Ser Ser Pro Thr Pro Gln Arg Arg Ala Pro Ala Val Pro
    50                  55                  60

Pro Ala Arg Pro Gly Ser Arg Gly Pro Ala Pro Gly Pro Pro Ala
65                  70                  75                  80

Gly Ser Ala Leu Gly Gly Ala Pro Pro Val Pro Ser Arg Pro Gly Ala
                85                  90                  95

Ser Pro Asp Pro Phe Gly Pro Pro Gln Val Pro Ser Arg Pro Asn
            100                 105                 110

Arg Ala Pro Pro Gly Val Pro Arg Ile Thr Ile Ser Asp Pro 115                 120                 125

<210> SEQ ID NO 14
<211> LENGTH: 125
<212> TYPE: PRT
<213> ORGANISM: homo sapiens

<400> SEQUENCE: 14

Met Lys Thr Ser Gly Asn Gln Asp Glu Ile Leu Val Ile Arg Lys Gly
1               5                   10                  15

Trp Leu Thr Ile Asn Asn Ile Gly Ile Met Lys Gly Gly Ser Lys Glu
            20                  25                  30

Tyr Trp Phe Val Leu Thr Ala Glu Asn Leu Ser Trp Tyr Lys Asp Asp
        35                  40                  45

Glu Glu Lys Glu Lys Lys Tyr Met Leu Ser Val Asp Asn Leu Lys Leu
    50                  55                  60

Arg Asp Val Glu Lys Gly Phe Met Ser Ser Lys His Ile Phe Ala Leu
65                  70                  75                  80

Phe Asn Thr Glu Gln Arg Asn Val Tyr Lys Asp Tyr Arg Gln Leu Glu
                85                  90                  95

Leu Ala Cys Glu Thr Gln Glu Glu Val Asp Ser Trp Lys Ala Ser Phe
            100                 105                 110

Leu Arg Ala Gly Val Tyr Pro Glu Arg Val Gly Asp Lys
        115                 120                 125

<210> SEQ ID NO 15
<211> LENGTH: 125
<212> TYPE: PRT
<213> ORGANISM: homo sapiens

<400> SEQUENCE: 15

Met Lys Thr Ser Gly Asn Gln Asp Glu Ile Leu Val Ile Arg Lys Gly
1               5                   10                  15

Trp Leu Thr Ile Asn Asn Ile Gly Ile Met Lys Gly Gly Ser Lys Glu
            20                  25                  30

Tyr Trp Phe Val Leu Thr Ala Glu Asn Leu Ser Trp Tyr Lys Asp Asp
        35                  40                  45

Glu Glu Lys Glu Lys Lys Tyr Met Leu Ser Val Asp Asn Leu Lys Leu
    50                  55                  60

Arg Asp Val Glu Lys Gly Phe Met Ser Ser Lys His Ile Phe Ala Leu
65                  70                  75                  80

Phe Asn Thr Glu Gln Arg Asn Val Tyr Lys Asp Tyr Arg Gln Leu Glu
                85                  90                  95

Leu Ala Cys Glu Thr Gln Glu Glu Val Asp Ser Trp Lys Ala Ser Phe
            100                 105                 110

Leu Arg Ala Gly Val Tyr Pro Glu Arg Val Gly Asp Lys
        115                 120                 125

<210> SEQ ID NO 16
<211> LENGTH: 122
<212> TYPE: PRT
<213> ORGANISM: homo sapiens

<400> SEQUENCE: 16

Lys Lys Thr Ser Gly Asn Gln Asp Glu Ile Leu Val Ile Arg Lys Gly
1               5                   10                  15

Trp Leu Thr Ile Asn Asn Ile Gly Ile Met Lys Gly Gly Ser Lys Glu
            20                  25                  30

Tyr Trp Phe Val Leu Thr Ala Glu Asn Leu Ser Trp Tyr Lys Asp Asp
         35                  40                  45

Glu Glu Lys Glu Lys Lys Tyr Met Leu Ser Val Asp Asn Leu Lys Leu
 50                  55                  60

Arg Asp Val Glu Lys Gly Phe Met Ser Ser Lys His Ile Phe Ala Leu
 65                  70                  75                  80

Phe Asn Thr Glu Gln Arg Asn Val Tyr Lys Asp Tyr Arg Gln Leu Glu
                 85                  90                  95

Leu Ala Cys Glu Thr Gln Glu Val Asp Ser Trp Lys Ala Ser Phe
                100                 105                 110

Leu Arg Ala Gly Val Tyr Pro Glu Arg Val
        115                 120

<210> SEQ ID NO 17
<211> LENGTH: 122
<212> TYPE: PRT
<213> ORGANISM: homo sapiens

<400> SEQUENCE: 17

Lys Lys Thr Ser Gly Asn Gln Asp Glu Ile Leu Val Ile Arg Lys Gly
 1               5                  10                  15

Trp Leu Thr Ile Asn Asn Ile Gly Ile Met Lys Gly Gly Ser Lys Glu
                 20                  25                  30

Tyr Trp Phe Val Leu Thr Ala Glu Asn Leu Ser Trp Tyr Lys Asp Asp
         35                  40                  45

Glu Glu Lys Glu Lys Lys Tyr Met Leu Ser Val Asp Asn Leu Lys Leu
 50                  55                  60

Arg Asp Val Glu Lys Gly Phe Met Ser Ser Lys His Ile Phe Ala Leu
 65                  70                  75                  80

Phe Asn Thr Glu Gln Arg Asn Val Tyr Lys Asp Tyr Arg Gln Leu Glu
                 85                  90                  95

Leu Ala Cys Glu Thr Gln Glu Val Asp Ser Trp Lys Ala Ser Phe
                100                 105                 110

Leu Arg Ala Gly Val Tyr Pro Glu Arg Val
        115                 120

<210> SEQ ID NO 18
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 18
cgacattgag ctggcttaca                                              20

<210> SEQ ID NO 19
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 19
catcgagtgc atgaagctgt                                              20

<210> SEQ ID NO 20
<211> LENGTH: 19
<212> TYPE: DNA
<213> ORGANISM: artificial sequence
<220> FEATURE:

-continued

<223> OTHER INFORMATION: synthetic oligonucleotide

<400> SEQUENCE: 20
accccacact tgcagaaaa                                                  19

<210> SEQ ID NO 21
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 21
ggctctttca gcttgaccac                                                 20

<210> SEQ ID NO 22
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 22
cactcttcaa caccgagcaa                                                 20

<210> SEQ ID NO 23
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 23
ggttgcgtat ggtctccact                                                 20

<210> SEQ ID NO 24
<211> LENGTH: 21
<212> TYPE: DNA
<213> ORGANISM: artificial sequence
<220> FEATURE:
<223> OTHER INFORMATION: synthetic oligonucleotide

<400> SEQUENCE: 24
cttcctgaag tgttgcaact a                                               21

<210> SEQ ID NO 25
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 25
cccaaggtga ccccgaat                                                   18

<210> SEQ ID NO 26
<211> LENGTH: 16
<212> TYPE: DNA
<213> ORGANISM: artificial sequence
<220> FEATURE:
<223> OTHER INFORMATION: synthetic oligonucleotide

<400> SEQUENCE: 26
ctgccgccgc ttctca                                                     16

<210> SEQ ID NO 27

-continued

```
<211> LENGTH: 27
<212> TYPE: DNA
<213> ORGANISM: artificial sequence
<220> FEATURE:
<223> OTHER INFORMATION: synthetic oligonucleotide

<400> SEQUENCE: 27
acttgctgga tctggtacag acagcgg                                     27

<210> SEQ ID NO 28
<211> LENGTH: 5
<212> TYPE: PRT
<213> ORGANISM: homo sapiens

<400> SEQUENCE: 28

Leu Pro Arg Gly Ser
1               5

<210> SEQ ID NO 29
<211> LENGTH: 6
<212> TYPE: PRT
<213> ORGANISM: homo sapiens

<400> SEQUENCE: 29

Glu Leu Ser Gly Gly Ala
1               5

<210> SEQ ID NO 30
<211> LENGTH: 5
<212> TYPE: PRT
<213> ORGANISM: homo sapiens

<400> SEQUENCE: 30

Phe Leu Arg Ala Gly
1               5

<210> SEQ ID NO 31
<211> LENGTH: 6
<212> TYPE: PRT
<213> ORGANISM: homo sapiens

<400> SEQUENCE: 31

Glu Gln Ser Val Gly Ala
1               5

<210> SEQ ID NO 32
<211> LENGTH: 18
<212> TYPE: DNA
<213> ORGANISM: artificial sequence
<220> FEATURE:
<223> OTHER INFORMATION: synthetic oligonucleotide

<400> SEQUENCE: 32
gtggactgtt ctcacgct                                               18
```

DYNAMIN MEDIATED DISEASES AND ASSOCIATED METHODS AND PRODUCTS

This application is a divisional application of, and claims priority to, U.S. Ser. No. 11/594,003, filed Nov. 7, 2006 and now allowed, which in turn claims the benefit under 35 U.S.C. §119(e) of the filing date of U.S. Ser. No. 60/734,900 filed on Nov. 8, 2005, both of which their contents are incorporated herein by reference in their entireties.

FEDERALLY SPONSORED RESEARCH

This invention was made with Government support under NIH NIDDK 1 RO1 DK064787-01A2. The Government may have certain rights to this invention.

FIELD OF INVENTION

This invention relates generally to the treatment of cathepsin or dynamin mediated diseases, such as proteinuria, cancer, and cognitive disease and related products. Diagnostic and other assays are also provided, as well as methods for podocyte cell gene transfer.

BACKGROUND OF INVENTION

About 20 million Americans have kidney insufficiency, a significant independent risk factor for cardio-vascular disease. The number of people diagnosed with kidney disease has doubled each decade for the last two decades impacting on human suffering and enormous Medicare costs imposed by end-stage renal disease. Urinary protein loss (proteinuria) is a common feature of kidney dysfunction of glomerular origin and is itself a risk factor for both renal and extra-renal diseases including cardiovascular disease. Diabetic kidney disease, for example, the most common and fastest growing form of ESRF in the U.S., is first manifest by the leakage of a small amount of protein in the urine and altered podocyte behavior. Kidney podocytes are highly differentiated cells and form the outer part of the ultrafiltration barrier. Their foot processes (FP) are interconnected by the slit diaphragm (SD). Proteinuric kidney diseases are typically associated with podocyte membrane remodeling (FP effacement and SD disruption).

SUMMARY OF INVENTION

The present invention provides a method for treating a disorder characterized by proteinuria comprising administering to a patient in a need thereof an effective amount of a dynamin protease resistance agent for treating the disorder characterized by proteinuria. In one embodiment, the disorder characterized by proteinuria is selected from the group consisting of: diabetes, hypertension, kidney disease, minimal change disease, membranous glomerulonephritis, focal segmental glomerulosclerosis, post-infectious glomerulonephritis, mesangioproliferative glomerulonephritis, HIV-associated nephropathy, IgA-nephropathy, diabetic neuropathy and cardiovascular disease.

In one aspect of the invention, the administering of the dynamin protease resistance agent induces the formation of actin stress fibers in podocytes. In one embodiment the administering of the dynamin protease resistance agent results in a proteolytic-cleavage resistant dynamin that is resistant to cleavage by cathepsin L. In yet another embodiment the proteolytic-cleavage resistant dynamin is resistant to proteolysis due to an altered proteolytic cleavage site. In one embodiment the dynamin protease resistance agent is proteolytic-cleavage resistant recombinant dynamin with the sequence of SEQ ID NO. 3 (L356Q, G358V). In one embodiment the dynamin protease resistance agent results in multimeric dynamin structures. In yet another embodiment the dynamin protease resistance agent results in dynamin that has impaired GTP hydrolysis. In one embodiment the dynamin protease resistance agent is a recombinant dynamin with the sequence of SEQ ID NO. 4 (R725A).

In one aspect of the invention an isolated polypeptide of SEQ ID NO. 1 or an active fragment thereof is provided, wherein the isolated polypeptide contains at least one mutation rendering it resistant to proteolytic-cleavage. In one embodiment the mutation of the recombinant dynamin does not impair its ability to form actin stress fibers in podocytes. In one embodiment the polypeptide is resistant to proteolytic-cleavage by cathepsin L. In one embodiment the polypeptide is resistant to cathepsin L cleavage because of a mutated cathepsin L-cleavage site. In one embodiment the mutation is L356Q, G358V. In yet another embodiment the polypeptide is resistant to cathepsin L cleavage because it forms multimeric structures. In one embodiment the polypeptide is impaired in GTP-hydrolysis.

In one aspect of the invention a pharmaceutical preparation comprising the isolated polypeptide is provided, and a pharmaceutically acceptable carrier. In one embodiment an isolated nucleic acid or a complement thereof, that encodes the polypeptide is provided.

In one aspect of the invention a recombinant expression vector is provided that comprises an isolated nucleic acid operably-linked to a promoter, wherein the isolated nucleic acid encodes the polypeptides disclosed herein or a complement thereof.

In one embodiment, a promoter is used that is not podocyte specific.

In one embodiment the promoter is a cytomegalovirus (CMV) promoter.

In one embodiment the promoter is a podocyte specific promoter. In one embodiment the promoter is a podocin promoter.

In one embodiment of the invention a host cell containing the vector disclosed herein is provided.

In one aspect of the invention a pharmaceutical preparation comprising the nucleic acid disclosed herein, and a pharmaceutically acceptable carrier is provided. In one embodiment the pharmaceutically acceptable carrier is a liposome.

In one aspect of the invention a method for treating a disorder characterized by proteinuria is provided comprising administering to a patient in a need thereof an effective amount of the polypeptide disclosed herein for treating the disorder characterized by proteinuria. In one embodiment the disorder characterized by proteinuria is selected from the group consisting of: diabetes, hypertension, kidney disease, minimal change disease, membranous glomerulonephritis, focal segmental glomerulosclerosis, post-infectious glomerulonephritis, mesangioproliferative glomerulonephritis, HIV-associated nephropathy, IgA-nephropathy, diabetic neuropathy and cardiovascular disease.

In one embodiment a method for treating a disorder characterized by proteinuria is provided comprising administering to a patient in a need thereof an effective amount of the nucleic acid disclosed herein for treating the disorder characterized by proteinuria.

In one aspect of the invention a method for detection of a disorder characterized by proteinuria comprising: determining an amount of dynamin in a podocyte cell; comparing the amount of dynamin to a pre-determined threshold or to a control level; detecting a disorder characterized by proteinuria wherein the amount of dynamin is below the predetermined threshold. In one embodiment the amount of dynamin is determined as a level of dynamin expression. In one embodiment the step of determining the amount of dynamin is performed using immunogold electron microscopy. In one embodiment the amount of dynamin is determined in a biological sample that contains podocytes. In one embodiment of the invention the biological sample is a biopsy sample of nephritic tissue.

In one aspect of the invention a method for screening for modulators of dynamin-dynamin interactions is provided comprising: contacting a dynamin expressing cell with a putative modulator of dynamin-dynamin interactions, staining the cell with antibodies to dynamin, wherein the antibodies are conjugated to either donor or receptor florophore; and, determining the dynamin-dynamin interaction by the analyzing the FRET data wherein a modulator of dynamin-dynamin interactions is identified based on a change in FRET signal from a baseline or a control sample. In one embodiment of the invention the dynamin is proteolysis-resistant dynamin. In one embodiment of the invention the putative modulator is a small molecule. In one embodiment of the invention the putative modulator is a known drug. In one embodiment of the invention the dynamin is overexpressed in the cell.

In one aspect of the invention a method for treating a disorder characterized by formation of cortical actin is provided comprising administering to a patient in a need thereof an effective amount of a dynamin protease resistance agent for treating the disorder characterized by formation of cortical actin. In one embodiment of the invention the disorder characterized by formation of cortical actin is cognitive impairment. In one embodiment of the invention the cognitive impairment is Alzheimer's or dementia. In one embodiment of the invention the dynamin protease resistance agent induces the formation of actin stress fibers in a neuron. In one embodiment of the invention the dynamin protease resistance agent results in a proteolytic-cleavage resistant dynamin that is resistant to cleavage by cathepsin L. In one embodiment of the invention the proteolytic-cleavage resistant dynamin is resistant to proteolysis due to altered proteolytic cleavage site. In one embodiment of the invention the proteolytic-cleavage resistant dynamin has the sequence of SEQ ID NO. 3 (L356Q, G358V). In one embodiment of the invention the dynamin protease resistance agent results in multimeric dynamin structures. In one embodiment of the invention the dynamin protease resistance agent results in dynamin that has impaired GTP hydrolysis. In one embodiment of the invention the dynamin protease resistance agent has the sequence of SEQ ID NO. 4 (R725A).

In one aspect of the invention a method for treating cancer comprising administering to a patient in a need thereof an effective amount of a dynamin protease resistance agent for treating cancer. In one embodiment of the invention the cancer is metastatic cancer and wherein the effective amount is an effective amount for preventing metastasis. In one embodiment of the invention the dynamin protease resistance agent induces the formation of actin stress fibers in a cancer cell. In one embodiment of the invention the dynamin protease resistance agent results in a proteolytic-cleavage resistant dynamin that is resistant to cleavage by cathepsin L. In one embodiment of the invention the proteolytic-cleavage resistant dynamin is resistant to proteolysis due to altered proteolytic cleavage site. In one embodiment of the invention the proteolytic-cleavage resistant dynamin has the sequence of SEQ ID NO. 3 (L356Q, G358V). In one embodiment of the invention the dynamin protease resistance agent results in multimeric dynamin structures. In one embodiment of the invention the dynamin protease resistance agent results in dynamin that has impaired GTP hydrolysis. In one embodiment of the invention the dynamin protease resistance agent has the sequence of SEQ ID NO. 4 (R725A).

In one aspect of the invention a method for delivering a gene to a podocyte in vivo, comprising: contacting a podocyte with an expression vector formulated in liposomes, wherein the expression vector encodes a gene endogenous to the podocyte. In one embodiment of the invention the gene is a urokinase receptor. In one embodiment of the invention the urokinase receptor is soluble. In one embodiment of the invention the urokinase receptor is membrane anchored. In one embodiment of the invention the urokinase receptor is a fragment. In one embodiment of the invention the urokinase receptor gene has a modified urokinase receptor function. In one embodiment of the invention the modified urokinase receptor function reduced. In one embodiment of the invention the modified urokinase receptor function enhanced. In one embodiment of the invention the gene is a dynamin mutant.

In one aspect of the invention a method for delivering a gene to a podocyte in a host is provided comprising contacting a podocyte with an expression vector formulated in liposomes, wherein the host is not immunocompromised.

In one aspect of the invention the dynamin protease resistance agent is a protease inhibitor. In one embodiment the protease inhibitor is a cathepsin inhibitor. In one embodiment the cathepsin inhibitor is cathepsin siRNA. In one embodiment the cathepsin inhibitor is a epoxysuccinyl peptide derivative. The epoxysuccinyl peptide derivative is E-64, E-64a, E-64b, E-64c, E-64d, CA-074, CA-074 Me, CA-030 or CA-028. In one embodiment the cathepsin inhibitor is Z-Phe-Phe-FMK, H-Arg-Lys-Leu-Trp-NH2, N-(1-Naphthalenylsulfonyl)-Ile-Trp-aldehyde, Z-Phe-Tyr(tBu)-diazomethylketone, or Z-Phe-Tyr-aldehyde. In one embodiment the cathepsin inhibitor is a small molecule. In one embodiment the small molecule is isolated from a small molecule combinatorial library.

BRIEF DESCRIPTION OF DRAWINGS

The accompanying drawings are not limiting with respect to the scope of the invention:

FIG. 4 is a panel of schemes (A, F), a table of sequences (B), Western blots (C, E), a bar graph (D) and an immunostain image (G) that show that dynamin is a specific proteolytic target of cathepsin L. A) Computer based cleavage site prediction of cathepsin L. Based on experimentally determined cleavage sites from databases, cleavage sites were aligned by Jotun Hein algorithm and motifs discovered by Block Maker software. Dynamin GTPase aminoacid sequence contains 3 potential cathepsin L cleavage sites. B) The high score cleavage site of dynamin is evolutionally preserved in many species. C) Western Blot of purified dynamin cleaved by cathepsin L at extralysosomal pH (7.0). The detection of cleavage products by GTPase antibody (N-terminus) yield two major fragments (40 kDa and 60 kDa). Importantly, processing of dynamin is inhibited by addition of GTPgammaS A similar cleavage of dynamin was also present in cultured podocytes and was induced after LPS administration. The cleavage could be blocked by administration of cathepsin L inhibitor E64. R725A (SEQ ID NO. 4) is cleaved stronger under normal conditions consistent with assembly deficiency of this hyperactive (GTB-bound) mutant. Of note, the addition of LPS induced the disappearance of the 40 kDa cleavage band. D) Quantification of the major cleavage fragment of dynamin at 40 kDa in cultured podocytes. E) Self assembly of dynamin induced by GTPgammaS protects from cathepsin L mediated cleavage even at acidic pH, demonstrating that cathepsin L cleavage is assembly dependent. F) Schematic depiction of the dynamin's GTPase cycle. E) Immunochemistry of dynaminWT and dynaminR275A without and with LPS treatment.

```
Dyn1,
5'CGACATTGAGCTGGCTTACA 3',   (For; SEQ ID NO. 18)

5'CATCGAGTGCATGAAGCTGT 3'.   (Rev; SEQ ID NO. 19)

Dyn2,
5'ACCCCACACTTGCAGAAAAC 3',   (For; SEQ ID NO. 20)

5'GGCTCTTTCAGCTTGACCAC 3'.   (Rev; SEQ ID NO. 21)

Dyn3,
5'CACTCTTCAACACCGAGCAA 3',   (For: SEQ ID NO. 22)

5'GGTTGCGTATGGTCTCCACT 3'.   (Rev; SEQ ID NO. 23)
```

B) Different amounts of recombinant dyn1 and dyn2 were probed in a Western blot using hudy1 or MAB 5402 antibodies. C) Urinary protein profiles over time following gene delivery of podocin-driven dynK44A, 40 kD GTPase and dynR725A (SEQ ID NO. 4) in mice. Please note that expression of dynR725A (SEQ ID NO. 4) lost its dominant negative phenotype at an earlier time point than expression of dynK44A or p40. D) Immunoblot analysis of CMV- and podocin-driven dynamin in liver (L) and kidney (K) using MAB5402 dynamin antibody. 60 µg of total protein was loaded per lane. Membrane was re-probed with anti-GAPDH antibody as a loading control. E) Immunogold electron micrographs of gene transferred CMV-driven dyn1K44A. F) Immunogold electron micrographs of gene-transferred podocin promoter-driven dyn1K44A. Pod=podocyte, GBM=glomerular basement membrane, END=endothelial cells.

Figure 26A:
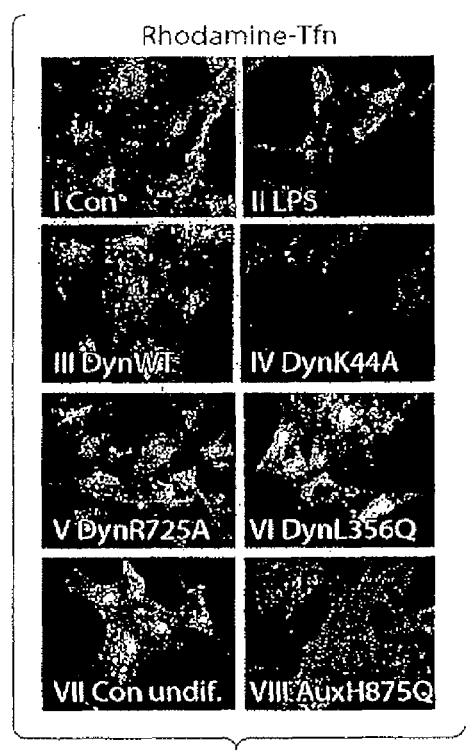
Figure 26B:
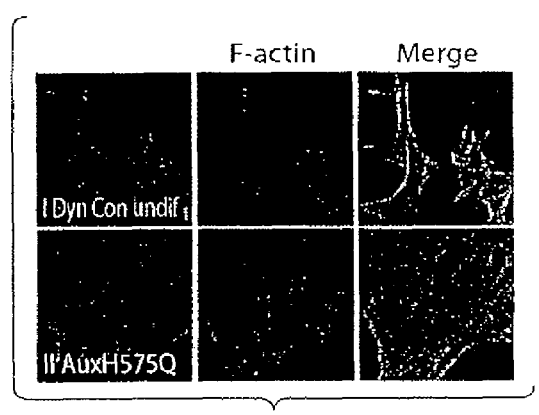
Figure 26C:
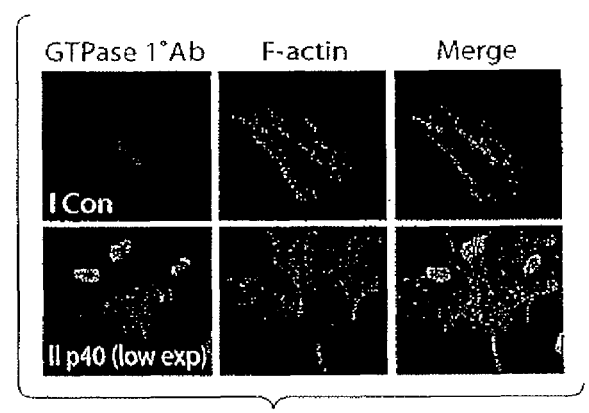

FIG. 26 is panel of immunostains (A-C) further illustrating the invention. A) Effects of dynamin mutants on rhodamine transferrin (R-Tfn) internalization in podocytes. Cells were incubated with 10 µg/ml R-Tfn for 10 min, and examined using confocal microscopy. B) Cultured podocytes were infected with adenoviruses expressing auxilin mutant, auxH875Q, and 18 h after infection, cells were stained with anti-auxilin or anti-dynamin (for non-infected undifferentiated control cells) antibody, and rhodamine phalloidin (red) to visualize F-actin. C) Cultured podocytes were transiently transfected with DNA encoding p40 under control of the podocine promoter. Efficiency of transfection was ~5%. Cells were stained using antidynamin GTPase antibody that recognizes N-terminal GTPase domain and thus p40 fragment, and rhodamine phalloidin to visualize F-actin. Note the background staining of nuclei in untransfected cells.

DETAILED DESCRIPTION

The present invention relates in some aspects to discoveries involving dynamin, recombinant dynamin, methods of use thereof and methods of delivery thereof. For instance, dynamin activity or expression can be manipulated for the therapeutic treatment of dynamin mediated disease. A dynamin mediated disease, as used herein, refers to a disease in which dynamin cleavage causes an undesirable biological effect, such as proteinuria, cancer, and cognitive disorders.

Accordingly, the methods of the present invention can be used to treat disorders characterized by proteinuria. As used herein "proteinuria" refers to any amount of protein passing through a podocyte that has suffered podocyte damage or through a podocyte mediated barrier that normally would not allow for any protein passage. For example, the processing of protein by cultured podocytes that have undergone actin-cytoskeleton rearrangement and FP effacement would result in proteinuria. As used herein "podocyte damage" refers to FP effacement and/or cortical actin rearrangement or any other reversible structural or functional change in podocytes that results in proteinuria. In an in vivo system the term "proteinuria" refers to the presence of excessive amounts of serum protein in the urine. Proteinuria is a characteristic symptom of either renal (kidney), urinary, pancreatic distress, nephrotic syndromes (i.e., proteinuria larger than 3.5 grams per day), eclampsia, toxic lesions of kidneys, and it is frequently a symptom of diabetes mellitus. With severe proteinuria general hypoproteinemia can develop and it results in diminished oncotic pressure (ascites, edema, hydrothorax).

As used herein a "disorder characterized by proteinuria" refers to, but it is not limited to: diabetes, hypertension, kidney disease, minimal change disease, membranous glomerulonephritis, focal segmental glomerulosclerosis, diabetic neuropathy, post-infectious glomerulonephritis, mesangioproliferative glomerulonephritis, HIV-associated nephropathy, IgA-nephropathy, and cardiovascular disease.

At the cellular level protein loss in the urine is accompanied by a structural rearrangement of podocyte cells. Renal ultrafiltration is located within the renal glomerulus, a combination of blood vessels and cells. Highly specialized podocyte cells perform the filtering work and are main target cells in kidney disease. Podocytes can reorganize their actin-based cytoskeleton in a highly dynamic fashion. Such a reorganization determines the integrity of the ultrafiltration barrier in the kidney. Reorganization of the actin cytoskeleton in podocyte foot processes from stress fibers into cortical actin leads to podocyte foot processes (FP) effacement and the development of urinary protein loss. Podocyte damage can be caused by many conditions and factors including LPS and purine aminonucleoside (PAN). These alterations lead to ongoing damage of the kidney and over time to a deterioration of the kidney function.

The invention is based in part on the surprising discovery that the large GTP-ase dynamin is expressed in podocytes and moreover that dynamin is an important regulator of actin cytoskeleton organization in podocytes. In normal podocytes, dynamin undergoes multimerization, which involves dimers, tetramers and high-order assemblies. Moreover dynamin regulates the formation of the actin-based cytoskeleton in podocytes, particularly stress fiber organization. As used herein "formation of stress fibers" refers to organization of the actin-cytoskeleton in stress fibers. The organization of actin in stress fibers in podocytes is associated with normal, physiological filtering function of podocytes that does not allow proteins in the urine. As used herein "formation of cortical actin" refers to organization of the actin-cytoskeleton in cortical actin. The organization of actin in cortical actin in podocytes is associated with impaired filtering function of podocytes and proteinuria. The invention is also based, at least in part, on the finding that GTP bound dynamin is an important component in the maintenance of a functional ultrafiltration barrier in the kidney.

Dynamin is a GTPase required for endocytosis of clathrin coated vesicles from the membrane. Dynamin's involvement in endocytosis was first discovered during the characterization of the temperature sensitive parylytic shibire mutation from *Drosophila melanogaster*. Three closely related isoforms have been identified in mammals. Dynamin1 is expressed exclusively in neurons, dynamin2 is ubiquitously expressed and dynamin3 is expressed primarily in the testes. The term dynamin as used herein refers to all isoforms of dynamin. Each of these isoforms of dynamin also has several splice variants. The protein and nucleotide sequences of the various splice variants and isoforms are readily available to the public, for example on the NCBI web site under accession numbers: Q05193 (SEQ ID NO. 5); L07807.1 (SEQ ID NO. 6), AAA02803.1 (SEQ ID NO. 7), L07808.1 (SEQ ID NO. 8), AAA02804.1 (SEQ ID NO. 9), L07809.1 (SEQ ID NO. 10), AAA02805.1 (SEQ ID NO. 11), L07810.1 (SEQ ID NO. 12), AAA02806.1 (SEQ ID NO. 13), 1DYNA (SEQ ID NO. 14), 1DYNB (SEQ ID NO. 15), 2DYNA (SEQ ID NO. 16), 2DYNB (SEQ ID NO. 17), etc. The amino acid and nucleotide sequences of dynamin 1 isoform 1 are reproduced in Tables A1 and A2 respectively. Common domain features of the dynamin proteins include an amino acid terminal GTPase domain, a central pleckstrin homology domain and a highly basic proline rich carboxyl terminus with several Src homology 3 (SH3) domains. These SH3 domains target the dynamin to the clathrin coated pit. Dynamin is known to interact with at least two proteins, AP2 adaptor protein complex and amphiphysin.

The invention is also based in part on the surprising discovery that cytoplasmic proteases, such as cathepsin L can cleave cellular targets such as dynamin. In certain embodiments the dynamin is active, GTP bound dynamin. The cytoplasmic proteases function as an alternative switch off mechanism to disrupt the normal life cycle of dynamin and thus the actin cytoskeleton organization in podocytes. It has now been discovered that during proteinuric kidney disease, induced extralysosomal cathepsin L cleaves dynamin which results in reorganization of the actin cytoskeleton. Surprisingly, dynamin self-assembly into higher order structures protects an evolutionary conserved cathepsin L cleavage site of dynamin and thus prevents cleavage.

In one aspect of the invention dynamin protease resistant agents (DPRA) are provided. As used herein the term "dynamin protease resistance agent" (DPRA) relates to any agent, including small molecules, nucleic acids, and peptides, that result in a dynamin that is resistant to protease activity. In some embodiments, DPRA also induce the formation of actin stress fibers. The dynamin molecules are resistant to a protease such as cathepsin or an endopeptidase.

As used herein the term "proteolytic-cleavage resistant dynamin" encompasses dynamin, recombinant dynamin, and dynamin multimeric molecules that are resistant to protease activity. For example, dynamin mutants that have altered proteolytic cleavage sites and/or produce multimeric dynamin, stabilized native or mutant dynamin and other agents that prevent dynamin cleavage.

Recombinant dynamin or dynamin mutant is a dynamin that differs from dynamin in primary structure, i.e., includes at least one mutation, deletion, or addition and that is resistant to proteolysis. As used and defined herein, the terms recombinant and mutant when referring to dynamin are interchangeable. Dynamin mutants include but are not limited to mutants having an altered proteolytic cleavage site and multimeric dynamin structures. In one aspect of the invention nucleic acids are provided that encode for recombinant dynamin.

As used herein "altered proteolytic cleavage site" refers to a proteolytic site of dynamin that has been altered such that the dynamin is no longer a target for proteolytic cleavage at that site. In one embodiment the proteolytic cleavage site of dynamin is altered by the introduction of mutations in the amino acid sequence of the dynamin peptide, in particular the amino acids that make up the cleavage site. The mutations can be produced directly in the peptide or through the use of nucleic acids that have been modified. The altered dynamin peptide no longer presents a substrate for protease recognition, binding and cleavage. Mutations can be introduced in the dynamin peptide sequence by any of the methods that are readily available in the art, for instance such as the recombinant techniques described herein. Alternatively, the proteolytic cleavage site can be altered by chemical modification of the amino acid residues that make up the cleavage site, by cross-linking of peptides or other molecules to residues that make up the cleavage site, or by truncating the cleavage site so that the altered dynamin peptide no longer presents a substrate for protease recognition, binding and cleavage.

Alternatively, an altered proteolytic cleavage site is a dynamin proteolytic cleavage site that is physically inaccessible to a protease, such as the proteolytic cleavage site of a multimer dynamin structure or higher order structure of dynamin. As used herein "multimeric dynamin structures" or "higher order structure of dynamin" refers to dynamin structures that are in higher order than dimers or tetramers, i.e., hexamers, octamers, decamers, ring-like structures, etc. Dynamin molecules with altered proteolytic site that form multimeric or higher order structures can be readily generated and detected by the methods and examples described herein.

As used herein, dynamin mutant includes isolated nucleic acids and proteins. As used herein with respect to polypeptides, proteins or active fragments thereof or nucleic acids, "isolated" means separated from its native environment and present in sufficient quantity to permit its identification or use. Isolated, when referring to a protein or polypeptide, means, for example: (i) selectively produced by expression cloning or (ii) purified as by chromatography or electrophoresis. Isolated proteins or polypeptides may be, but need not be, substantially pure. The term "substantially pure" means that the proteins or polypeptides are essentially free of other substances with which they may be found in nature or in vivo systems to an extent practical and appropriate for their intended use. Substantially pure polypeptides may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, i.e. isolated from other proteins.

With respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art. An isolated nucleic acid as used herein is not a naturally occurring chromosome.

Modifications to a dynamin polypeptide are typically made to the nucleic acid which encodes the dynamin polypeptide, and can include deletions, point mutations, truncations, amino acid substitutions and additions of amino acids or non-amino acid moieties. Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the dynamin amino acid sequence.

Mutations of a nucleic acid which encode a dynamin polypeptide preferably preserve the amino acid reading frame of the coding sequence, and preferably do not create regions in the nucleic acid which are likely to hybridize to form secondary structures, such a hairpins or loops, which can be deleterious to expression of the modified polypeptide.

Modifications can be made by selecting an amino acid substitution, or by random mutagenesis of a selected site in a nucleic acid which encodes the dynamin polypeptide. Modified dynamin polypeptides then can be expressed and tested for one or more activities (e.g., susceptibility to catalysis) to determine which mutation provides a modified polypeptide with the desired properties.

The skilled artisan will also realize that conservative amino acid substitutions may be made in dynamin polypeptides to provide dynamin polypeptides, that have the functional capabilities of dynamin mutants. As used herein, a "conservative amino acid substitution" refers to an amino acid substitution which does not alter the relative charge or size characteristics of the protein in which the amino acid substitution is made. Dynamin mutants can be prepared according to methods for altering polypeptide sequence known to one of ordinary skill in the art such as are found in references which compile such methods, e.g., *Molecular Cloning: A Laboratory Manual*, J. Sambrook et al., eds., Second Edition, Cold Spring Harbor Laboratory Press, Cold Spring Harbor, N.Y., 1989, or *Current Protocols in Molecular Biology*, F. M. Ausubel et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Dynamin mutants are based on and derived from the amino acid sequence of the dynamin protein. The GTP-hydrolysis impaired or cathepsin L resistant mutants described herein are preferred. The preferred DPRAs are soluble under physiological conditions. For example if the DPRAs are peptides, their termini can be shortened as desired, provided that their DPRA function as described herein remains intact. The preferred amino acid sequence of dynamin corresponds to the human protein dynamin. Suitable DPRA sequences can also be derived from the amino acid sequence of dynamin isolated from other mammals.

Various dynamin mutants are protected from proteolytic cleavage during pathophysiological events in the kidney resulting in the protection of podocyte structure or reversal of podocyte structure and function. In one aspect of the invention dynamin mutants are provided that are resistant to protease cleavage because of a mutated cleavage site. In one embodiment of the invention the protease cleavage site is determined using the dynamin sequence and bioinformatics tools, such as PEPS (Prediction of Endopeptidase Substrates) developed by Reinheckel et al. (Lohmuller et al., 2003). By using PEPS and the dynamin amino acid or nucleotide sequences three putative cathpesin L sites within dynamin can be identified. Together, these data are consistent with sequences ELSGGA (SEQ ID NO. 29) and FLRAG (SEQ ID NO. 30) as cathepsin L specific recognition sequences within dynamin. It would be appreciated by a person of ordinary skill in the art that mutations and substitutions with these consensus sequences could be used to generate dynamin mutants that are resistant to protease cleavage. In one embodiment of the invention the DPRA is dynamin mutant that is not recognized by cathepsin L. An example of such a mutant is dynL356Q, G358V (L356Q, G358V, DynL356Q, G358V, $Dyn^{L356Q,\ G358V}$, SEQ ID NO. 3). This mutant is described in more detail in the examples.

Another mutant is one that results in multimeric dynamin structures. For example dynR725A (R725A, DynR725A, $Dyn^{R725A}$, SEQ ID NO. 4). This mutant is described in more detail in the examples. Expression of dynR725A (SEQ ID NO. 4), a mutant with impaired GTP hydrolysis capacity, significantly induced stress fibers formation in podocytes.

It would be appreciated by one of ordinary skill in the art that other mutants of similar properties can be constructed by making substitutions in the dynamin sequence. As used herein "dominant-positive" or "dominant-activator" mutant refers to a mutant that has the capacity to bind GTP and exist longer in the GTP bound form, which in turn, as described herein promotes the formation actin stress fibers or increases resistance to proteases. Conversely, as used herein "dominant-negative" when referring to dynamin refers to a dynamin mutant that can not bind GTP and therefore can not induce the formation of actin stress fibers or is sensitive to proteases. Accordingly, overexpression of the dominant-negative dynamin, dynK44A, mutant that cannot bind GTP, resulted in the loss of stress fibers and their rearrangement into a cortical actin cytoskeleton. It will be appreciated by one of ordinary skill in the art that dynamin mutants with altered GTP binding and activity can be generated by mutations to the N-terminal GTP binding domain of dynamin.

DPRAs of the invention may be produced using any of the methods and techniques known to those skilled in the art. For example, DPRAs that are dynamin mutants can be purified from a source which naturally expresses the protein, can be isolated from a recombinant host which has been altered to express the desired mutant or fragment thereof, or can be synthesized using protein synthesis techniques known in the art. The skilled artisan can readily adapt a variety of techniques in order to obtain DPRA peptide agents.

The isolation of native DPRA proteins is known in the art. In order to generate DPRA peptides, isolated native protein may be converted by enzymatic and/or chemical cleavage to generate fragments of the whole protein, for example by reacting cell lines which express a DPRA protein with an enzyme such as papain or trypsin or a chemical such as cyanogen bromide. Alternatively, DPRA or a fragment thereof may be expressed in recombinant bacteria or yeast, each of which is well known in the art.

Other agents that prevent dynamin cleavage include but are not limited to small molecules, peptides and other drugs, including known drugs, that prevent (i.e. reduce or inhibit further increase) dynamin cleavage. Such agents can be identified using routine screening methods. For instance, DPRAs of the present invention can be identified using the methods described herein including FLIM, a fluorescence energy transfer (FRET) assay. This assay is described in more detail below. Briefly, one can identify modulators of dynamin-dynamin interactions by observing differences in FRET of the fluorescently labeled dynamin in the presence and absence of putative modulators. The screening may be a random screen or it may be rationally designed.

For random screening, putative modulators are selected at random and assayed for their ability to produce the desired physiological effect. For instance, the putative modulators may be assayed for the ability to reduce selectively or specifically the amount or rate of dynamin cleavage by proteases, particularly cathepsin L. Any suitable method or technique known to those skilled in the art may be employed to assay putative modulators.

Methods for screening using rational design employ the same types of screening methods but begin with a set of compounds that has been designed to specifically maximize function. For rational selection or design, the DPRA may be selected based on the dynamin GTP binding domain or the dynamin protease cleavage site. Any of the suitable methods and techniques known to those skilled in the art may be employed for rational selection or design. For example, one skilled in the art can readily adapt currently available procedures to generate pharmaceutical agents capable of binding to a specific peptide sequence of dynamin or cathepsin L, thereby promoting dynamin oligomerization or inhibition of cathepsin L activity. Illustrative examples of such available procedures are described, for example, in Hurby et al., "Application of Synthetic Peptides Antisense Peptides," in Synthetic Peptides, A User's Guide, W.H. Freeman, N.Y., pp. 289-307 (1992); Kaspczak et al., Biochemistry 28:9230 (1989); and Harlow, Antibodies, Cold Spring Harbor Press, N.Y. (1990).

In one aspect of the invention DPRAs include antibodies and antibody fragments which are capable of binding to a dynamin, dynamin mutant peptide or a protease, such as cathepsin L and consequently acting as a competitive inhibitor for protease binding to dynamin cleavage site. The antibodies of the present invention include polyclonal and monoclonal antibodies, as well as antibody fragments and derivatives that contain the relevant antigen binding domain of the antibodies. Such antibodies or antibody fragments are preferably used in the diagnostic and therapeutic embodiments of the present invention.

Another type of the DPRAs of the present invention are protease inhibitors such as cathepsin inhibitors. Cathepsins include but are not limited to cathepsin L, B and D. Inhibitors of cathepsins include cathepsin L, B, and D inhibitors, antisense to cathepsin, siRNA, and antisense-peptide sequences.

Examples of cathepsin inhibitors include but are not limited to the group consisting of epoxysuccinyl peptide derivatives [E-64, E-64a, E-64b, E-64c, E-64d, CA-074, CA-074 Me, CA-030, CA-028, etc.], peptidyl aldehyde derivatives [leupeptin, antipain, chymostatin, Ac-LVK-CHO, Z-Phe-Tyr-CHO, Z-Phe-Tyr(OtBu)-COCHO.$H_2O$, 1-Naphthalenesulfonyl-Ile-Trp-CHO, Z-Phe-Leu-COCHO.$H_2O$, etc.], peptidyl semicarbazone derivatives, peptidyl methylketone derivatives, peptidyl trifluoromethylketone derivatives [Biotin-Phe-Ala-fluoromethyl ketone, Z-Leu-Leu-Leu-fluoromethyl ketone minimum, Z-Phe-Phe-fluoromethyl ketone, N-Methoxysuccinyl-Phe-HOMO-Phe-fluoromethyl ketone, Z-Leu-Leu-Tyr-fluoromethyl ketone, Leupeptin trifluoroacetate, ketone, etc.], peptidyl halomethylketone derivatives [TLCK, etc.], bis(acylamino)ketone [1,3-Bis(CBZ-Leu-NH)-2-propanone, etc.], peptidyl diazomethanes [Z-Phe-Ala-CHN2, Z-Phe-Thr(OBzl)-CHN2, Z-Phe-Tyr (O-t-But)-CHN2, Z-Leu-Leu-Tyr-CHN2, etc.], peptidyl acyloxymethyl ketones, peptidyl methylsulfonium salts, peptidyl vinyl sulfones [LHVS, etc.], peptidyl nitriles, disulfides[5,5'-dithiobis [2-nitrobenzoic acid], cysteamines, 2,2'-dipyridyl disulfide, etc.], non-covalent inhibitors [N-(4-Biphenylacetyl)-S-methylcysteine-(D)-Arg-Phe-b-phenethylamide, etc.], thiol alkylating agents [maleimides, etc,], azapeptides, azobenzenes, O-acylhydroxamates [Z-Phe-Gly-NHO-Bz, Z-FG-NHO-BzOME, etc.], lysosomotropic agents [chloroquine, ammonium chloride, etc.], and inhibitors based on Cystatins [Cystatins A, B, C, stefins, kininogens, Procathepsin B Fragment 26-50, Procathepsin B Fragment 36-50, etc.]. In one embodiment CA-074 is preferred.

In one embodiment, the invention provides methods for inhibiting at least one enzymatic activity of cathepsin L. In one embodiment the DPRAs are cathepsin L inhibitors such as Z-Phe-Phe-FMK, H-Arg-Lys-Leu-Trp-NH2, N-(1-Naphthalenylsulfonyl)-Ile-Trp-aldehyde, Z-Phe-Tyr(tBu)-diazomethylketone, and Z-Phe-Tyr-aldehyde.

Antisense-peptide sequences are short peptides which are specifically designed to bind to a particular amino acid sequence. In general, such antisense peptide agents may be generated using methods known in the art, such as those described, for example, in Hurby et al., "Application of Synthetic Peptides: Antisense Peptides," in Synthetic Peptides, A User's Guide, W.H. Freeman, N.Y., pp. 289-307 (1992) and Kaspczak et al., Biochemistry 28:9230-8 (1989).

An additional class of DPRAs of the invention are natural ligands of cathepsin L that reduce or block the binding of the protease to dynamin. As used herein, a natural ligand of cathepsin L is defined as any substance which binds to cathepsin L, such as soluble fragments of dynamin containing the protease recognition site, e.g., the ELSGGA (SEQ ID NO. 29) and FLRAG (SEQ ID NO. 30) motifs. Such soluble fragments may be prepared by any suitable method known to those skilled in the art, such as the method of Davis et al., Nature 326:760-765 (1987). Moreover, soluble forms of the receptor may be formed by inserting a stop codon in front of the region of DNA encoding the cytoplasmic or transmembrane domain (Yokade et al., J. Cell. Biol. 117:39 (1992)).

In other aspects the invention also includes DPRAs that are non-hydrolysable analogs of GTP, such as GTPγS and short actin filaments.

In one aspect of the invention alternative therapeutic methods are provided for the treatment of other disorders that involve dynamin such as cancer, prevention of metastasis. In light of these novel findings, an early effect of nm23-mediated metastatic processes is due to slowing down dynamin-dependant endocytosis by lowering the levels of GTP inside the cell. Point mutations in dynamin's GAP domain, have been generated which slow down GTP-hydrolysis by dynamin, and thus prolong the lifetime of dynamin: GTP.

As used herein, "treating cancer" includes preventing the development of a cancer, reducing the symptoms of cancer, inhibiting the growth of an established cancer, slowing the progression, reducing the symptoms, preventing metastasis and/or any other desired effect on cancer. DPRAs of the invention can be administered prior to a cancer surgery, after a cancer surgery, or as part of any cancer therapeutic regimen including cancer medicaments. As used herein, a "cancer medicament" refers to an agent which is administered to a subject for the purpose of treating a cancer.

Cancers, include but are not limited to: biliary tract cancer; bladder cancer; breast cancer; brain cancer including glioblastomas and medulloblastomas; cervical cancer; choriocarcinoma; colon cancer including colorectal carcinomas; endometrial cancer; esophageal cancer; gastric cancer; head and neck cancer; hematological neoplasms including acute lymphocytic and myelogenous leukemia, multiple myeloma, AIDS-associated leukemias and adult T-cell leukemia lymphoma; intraepithelial neoplasms including Bowen's disease and Paget's disease; liver cancer; lung cancer including small cell lung cancer and non-small cell lung cancer; lymphomas including Hodgkin's disease and lymphocytic lymphomas; neuroblastomas; oral cancer including squamous cell carcinoma; esophageal cancer; osteosarcomas; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, synovial sarcoma and osteosarcoma; skin cancer including melanomas, Kaposi's sarcoma, basocellular cancer, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; transitional cancer and renal cancer including adenocarcinoma and Wilms tumor.

A subject or patient is preferably a patient diagnosed with cancer. A patient can be diagnosed with cancer using any recognized diagnostic indicator including, but not limited to, physical symptoms, molecular markers, or imaging methods. A subject can also be a subject at risk of developing cancer (e.g. a subject that has been exposed to a carcinogen or other toxin, a subject with one or more genetic predispositions for cancer, a subject with symptoms of early cancer, or a subject that has been treated for cancer and is at risk of cancer recurrence or metastasis).

The DPRA may be administered in conjunction with an anti-cancer therapy. Anti-cancer therapies include cancer medicaments, radiation and surgical procedures. For the purpose of this specification, cancer medicaments are classified as chemotherapeutic agents, immunotherapeutic agents, and cancer vaccines.

Additionally, the methods of the invention are intended to embrace the use of more than one cancer medicament along with the DPRAs. As an example, where appropriate, the DPRAs may be administered with both a chemotherapeutic agent and an immunotherapeutic agent. Alternatively, the cancer medicament may embrace an immunotherapeutic agent and a cancer vaccine, or a chemotherapeutic agent and a cancer vaccine, or a chemotherapeutic agent, an immunotherapeutic agent and a cancer vaccine all administered to one subject for the purpose of treating a subject having a cancer or at risk of developing a cancer.

The chemotherapeutic agent may be selected from the group consisting of methotrexate, vincristine, adriamycin, cisplatin, non-sugar containing chloroethylnitrosoureas, 5-fluorouracil, mitomycin C, bleomycin, doxorubicin, dacarbazine, taxol, FRAGYLINE, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/LOMETEXOL, GLAMOLEC, CI-994, TNP-470, HYCAMTIN/TOPOTECAN, PKC412, VALSPODAR/PSC833, NOVANTRONE/MITROXANTRONE, METARET/SURAMIN, BATIMASTAT, E7070, BCH-4556, CS-682, 9-AC, AG3340, AG3433, Incel/VX-710, VX-853, ZD0101, ISI641, ODN 698, TA 2516/MARMISTAT, BB2516/MARMISTAT, CDP 845, D2163, PD183805, DX8951f, LEMONAL DP 2202, FK 317, PICIBANIL/OK-432, AD 32/VALRUBICIN, METASTRON/strontium derivative, TEMODAL/TEMOZOLOMIDE, EVACET/liposomal doxorubicin, YEWTAXAN/PACLITAXEL, TAXOL/PACLITAXEL, XELOAD/CAPECITABINE, FURTULON/DOXIFLURIDINE, CYCLOPAX/oral paclitaxel, Oral Taxoid, SPU-077/Cisplatin, HMR 1275/FLAVOPIRIDOL, CP-358 (774)/EGFR, CP-609 (754)/RAS oncogene inhibitor, BMS-182751/oral platinum, UFT(TEGAFUR/Uracil), ERGAMISOL/LEVAMISOLE, ENILURACIL/776C85/5FU enhancer, CAMPTO/LEVAMISOLE, CAMPTOSAR/IRINOTECAN, TUMODEX/RALITREXED, LEUSTATIN/CLADRIBINE, PAXEX/PACLITAXEL, DOXIL/liposomal doxorubicin, CAELYX/liposomal doxorubicin, FLUDARA/FLUDARABINE, PHARMARUBICIN/EPIRUBICIN, DEPOCYT, ZD1839, LU 79553/BIS-NAPHTALIMIDE, LU 103793/DOLASTAIN, CAETYX/liposomal doxorubicin, GEMZAR/GEMCITABINE, ZD 0473/ANORMED, YM 116, iodine seeds, CDK4 and CDK2 inhibitors, PARP inhibitors, D4809/DEXIFOSAMIDE, IFES/MESNEX/IFOSAMIDE, VUMON/TENIPOSIDE, PARAPLATIN/Carboplatin, PLANTINOL/cisplatin, VEPESIDE/ETOPOSIDE, ZD 9331, TAXOTERE/DOCETAXEL, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, CYTARABINE HCl, DACTINOMYCIN, DAUNORUBICIN HCl, Estramustine phosphate sodium, ETOPOSIDE (VP16-213), FLOXURIDINE, Fluorouracil (5-FU), FLUTAMIDE, Hydroxyurea (hydroxycarbamide), IFOSFAMIDE, Interferon Alfa-2a, Alfa-2b, LEUPROLIDE acetate (LHRH-releasing factor analogue), LOMUSTINE (CCNU), MECHLORETHAMINE HCl (nitrogen mustard), MERCAPTOPURINE, MESNA, MITOTANE (o.p'-DDD), MITOXANTRONE HCl, OCTREOTIDE, PLICAMYCIN, PROCARBAZINE HCL, STREPTOZOCIN, TAMOXIFEN CITRATE, Thioguanine, THIOTEPA, Vinblastine sulfate, Amsacrine (m-AMSA), Azacitidine, Erthropoietin, Hexamethylmelamine (HMM), Interleukin 2, MITOGUAZONE (methyl-GAG; methyl glyoxal bis-guanylhydrazone; MGBG), PENTOSTATIN (2' deoxycoformycin), SEMUSTINE (methyl-CCNU), TENIPOSIDE (VM-26) and VINDESINE sulfate, but it is not so limited.

The immunotherapeutic agent may be selected from the group consisting of RIBUTAXIN, HERCEPTIN, QUADRAMET, PANOREX, IDEC-Y2B8, BEC2, C225, ONCOLYM, SMART M195, ATRAGEN, OVAREX, BEXXAR, LDP-03, ior t6, MDX-210, MDX-11, MDX-22, OV103, 3622W94, anti-VEGF, ZENAPAX, MDX-220, MDX-447, MELIMMUNE-2, MELIMMUNE-1, CEACIDE, PRETARGET, NOVOMAb-G2, TNT, GLIOMAB-H, GNI-250, EMD-72000, LYMPHOCIDE, CMA 676, MONOPHARM-C, 4B5, IOR EGF.R3, IOR C5, BABS, ANTI-FLK-2, MDX-260, ANA Ab, SMART 1D10 Ab, SMART ABL 364 Ab and IMMURAIT-CEA, but it is not so limited.

The cancer vaccine may be selected from the group consisting of EGF, Anti-idiotypic cancer vaccines, Gp75 antigen, GMK melanoma vaccine, MGV ganglioside conjugate vaccine, Her2/neu, OVAREX, M-VAX, O-VAX, L-VAX, STN-KHL THERATOPE, BLP25 (MUC-1), liposomal idiotypic vaccine, MELACINE, peptide antigen vaccines, toxin/antigen vaccines, MVA-based vaccine, PACIS, BCG vaccine, TA-HPV, TA-CIN, DISC-virus and IMMUCYST/THERACYS, but it is not so limited.

In one aspect of the invention therapeutic methods are provided for disorders mediated by cortical actin, such as cognitive impairment. Cognitive impairment refers to a disorder in which their is some cognitive diminution. Cognitive disorders include but are not limited to Alzheimer's and dementia.

In one aspect of the invention methods for treating proteinuria are provided by inhibiting uPAR. The invention is based at least in part on the scientific discovery that uPAR is induced during proteinuria and that uPAR−/− mice are protected from the development of proteinurea. In one aspect of the invention the compounds of the invention are uPAR inhibitors, including small molecules, peptides and antibodies.

The invention also encompasses diagnostic assays for determining the presence of a disorder characterized by proteinuria in a subject. This aspect of the invention is based, at least in part, on the discovery that dynamin expression is reduced in damaged or proteinuric podocytes. In the method an amount of dynamin in a podocyte cell is determined. That amount is compared to a pre-determined threshold or to a control level. A disorder characterized by proteinuria is determined when the amount of dynamin is below the pre-determined threshold. As used here in "pre-determined threshold or a control level" refers to dynamin levels in normal, healthy podocytes, i.e. podocytes not affected by podocyte damage or proteinuria. The podocyte cells may be within a biological sample. The biological sample may be, for instance, a biopsy sample of proteinuric tissue.

The detection of dynamin in podocyte cells can be readily carried out by standard immunostaining or immunocytometric methods, readily known by persons of ordinary skill in the art. As used herein "immunostaining" refers to a technique of applying coloured or fluorescent dyes to tissues in preparation for microscopic examination. The assay may be performed using immunogold electron microscopy.

In one embodiment the diagnostic assays are performed on cells and/or tissue samples wherein morphological changes of the actin-cytoskeleton can not be readily detected by any other immunocytometric methods. For example one such disorder would be minimal change disease. The term minimal change disease comes from the notion that morphological podocyte changes are only visible by electron microscopy. Detection of proteinuria in patients with minimal change disease by immunocytometric methods would be advantageous because it provide ease and speed of detection.

The immunocytometric methods may be performed using labeled antibodies. An antibody is said to be "detectably labeled" if the antibody, or fragment thereof, is attached to a molecule which is capable of identification, visualization, or localization using known methods. Suitable detectable labels include radioisotopic labels, enzyme labels, non-radioactive isotopic labels, fluorescent labels, affinity labels, chemiluminescent labels and nuclear magnetic resonance contrast agents.

Illustrative examples of suitable enzyme labels include, but are not limited to, luciferase, malate dehydrogenase, staphylococcal nuclease, delta-5-steroid isomerase, yeast-alcohol dehydrogenase, alpha-glycerol phosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase, and acetylcholine esterase.

Examples of suitable radioisotopic labels include, but are not limited to, $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled monoclonal antibody by the liver. In addition, this radionucleotide has a more favorable gamma emission energy for imaging (Perkins et al., Eur. J. Nucl. Med. 10:296-301 (1985); Carasquillo et al., J. Nucl. Med. 28:281-287 (1987)). For example, $^{111}$In coupled to monoclonal antibodies with 1-(p-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Illustrative examples of suitable non-radioactive isotopic labels include, but are not limited to $^{157}$Gd, $^{55}$Mn, $^{162}$Dy, $^{52}$Tr, and $^{56}$Fe.

Illustrative examples of suitable fluorescent labels include, but are not limited to, an $^{152}$Eu label, a fluorescent protein (including green fluorescent protein (GFP), enhanced green fluorescent protein (EGFP), enhanced yellow fluorescent protein (YFP) and enhanced cyan fluorescent protein (ECFP), a fluorescein label, an isothiocyanate label, a rhodamine label, a phycoerythrin label, a phycocyanin label, an allophycocyanin label, an o-phthaldehyde label, and a fluorescamine label.

Illustrative examples of chemiluminescent labels include a luminal label, an isoluminal label, an aromatic acridinium ester label, an imidazole label, an acridinium salt label, an oxalate ester label, a luciferin label, a luciferase label, and an aequorin label.

Illustrative examples of nuclear magnetic resonance contrasting agents include paramagnetic heavy metal nuclei such as Gd, Mn, and Fe.

The coupling of one or more molecules to antibodies is envisioned to include many chemical mechanisms, for instance covalent binding, affinity binding, intercalation, coordinate binding, and complexation.

The covalent binding can be achieved either by direct condensation of existing side chains or by the incorporation of external bridging molecules. Many bivalent or polyvalent agents are useful in coupling protein molecules to other proteins, peptides or amine functions, etc. For example, the literature is replete with coupling agents such as carbodiimides, diisocyanates, glutaraldehyde, diazobenzenes, and hexamethylene diamines. This list is not intended to be exhaustive of the various coupling agents known in the art but, rather, is exemplary of the more common coupling agents.

In another aspect the invention includes development of a cell-based assay to detect dynamin-dynamin interactions. In one embodiment the dynamin-dynamin interactions are screened within podocytes. In another embodiment the dynamin-dynamin interactions are screened within COS cells. In yet another embodiment the dynamin-dynamin interactions are screened within any other cell capable of expressing dynamin or mutant dynamin. The assay can be used to screen for small molecules and/or drugs affecting the dynamin-dynamin interactions and thus represent potential pharmacotherapeutics for kidney diseases, cancer and cognitive diseases.

In one embodiment the cell-based assay to monitor dynamin-dynamin interactions is performed on a cultured mouse podocyte cell line and the readout of dynamin self-assembly using fluorescence lifetime imaging microscopy (FLIM). FLIM is based on the fluorescence resonance energy transfer (FRET) between the donor and acceptor that shortens the lifetime of the donor if the acceptor distance is within ≈100 Å (10 nm). Therefore, the detection of shortened lifetimes demonstrates FRET and indicates spatial proximity of the two labeled molecules. The assay is based on overexpressing dynamin in podocytes, and subsequently staining fixed cells with monoclonal anti-dynamin antibodies that have been conjugated with donor or acceptor florophores. In one embodiment of the invention, Alexa-488 is used as the donor florophore and Alexa-568 is used as the acceptor florophore. In yet another embodiment the donor florophore is dynamin conjugated enhanced-cyan fluorescence protein (ECFP) and the acceptor is dynamin conjugated enhanced yellow-fluorescence protein (EYFP). It will be appreciated by the person of ordinary skill in the art that numerous combinations of FRET donor and acceptors can be used, which are readily available and known. In one embodiment, the FLIM assay is carried out in COS cells and the donor can be selected from the list consisting of: ECFP-WT, ECFP-I690K, ECFP-K44A, ECFP-K694A, and the acceptor can be selected from the list consisting of: EYFP, EYFP-WT, EYFP-K44A, EYFP-I690K, EYFP-K694A. In yet another embodiment the FLIM assay is performed in podocytes and the donor is GTPase-Alexa488 and the acceptor is selected from the list consisting of: DAM-Alexa568, GTPase-Alexa568, and Hudy1-Alexa568. Cells are stained by mixing both donor and acceptor florophores in equal amounts, and examining the spatially-restricted lifetime shortening in cells detects the localization of dynamin-dynamin interactions in cells. Since dynamin-dynamin interactions are vital for the function of the podocyte, it will be appreciated by the person of ordinary skill in the art that this assay can now be used to screen peptides, small molecules or drugs which can affect these molecular interactions. For example such molecules are cytocholasin D, jasplakinolide, colchisine, dynK44A, dynK694A, dynWT, dynI690K, dynR725A (SEQ ID NO. 4), dynL356Q, G358V, (SEQ ID NO. 3) any combination thereof, etc.

In one embodiment of the invention a FLIM-assay is provided that specifically detects dynamin self-assembly into the higher order structures in podocytes. As used herein "dynamin higher order structures" refers to dynamin oligomerized in structures higher than dimer or tetramer.

The DPRAs of the present invention may be used in vitro and/or in vivo to study interaction and binding of dynamin and cathepsin L, and to reduce the rate of onset and/or ameliorate the duration and severity of proteinuria (i.e., to treat or prevent proteinuria). In addition, the agents of the present invention may be used in qualitative, quantitative and preparative assays and purification procedures to isolate, identify and facilitate the purification of dynamin or cathepsin L.

A gene transfer system for transferring genes to podocyte cells in the kidney is also part of the invention. The method is performed via recombinant vectors formulated in liposomes. The expressed genes may be able to directly affect kidney structure and function. The recombinant vector includes a promoter such as a podocyte specific promoter.

The method for gene transfer described herein may be used to deliver a dynamin mutant to podocytes in vivo. In this instance the recombinant vector may be used in a method for treating a disorder characterized by proteinuria by providing transient intravenous gene delivery system of dynamin mutants with either a mutated cathepsin L cleavage site or by the dominant active GTP-hydrolysis impaired dynamin mutant, such as R725A (SEQ ID NO. 4). Both categories of mutants are capable of escaping induced cathepsin L cleavage in diseased podocytes with rearranged actin cytoskeleton. For example, dynL356Q, G358V (SEQ ID NO. 3) by amino acid exchanges at a highly conserved cathepsin L cleavage site and dynamin dynR725A (SEQ ID NO. 4) by the formation of cathepsin L inaccessible high-order assemblies. An example of such a method is presented in the Examples.

In the gene transfer method it may be preferable to use a dynamin isoform 1 mutant unless specified otherwise. Podocytes normally express dynamin 2 and little dynamin 3, but not dynamin 1. It will be appreciated by one of ordinary skill in the art that because the isoform 1 is not naturally expressed in podocytes, its vector expression can be easily tracked and quantified by standard biochemical and/or immunostaining methods, e.g. specific monoclonal dynamin 1 antibody.

The gene transfer method may also be used to transfer other genes for other purposes of podoytes. For instance, as presented in the examples herein, endogenous genes, such as urokinase receptor, may be delivered to the podocyte.

Preferably the gene is delivered to a non-immunocompromised host. A non-immunocompromised host is a host have a normal immune system. A host may be immunocompromised by virtue of experimental manipulation (research animals), genetic disorders or external influences, such as viral infection.

In one embodiment the transient mutant dynamin expression from the DPRA recombinant vector can be detected for 24 hrs, 48 hrs, 72 hrs, or 96 hrs post administration. In one embodiment of the invention the peak transient mutant dynamin expression from the DPRA recombinant vector is detected at 6, 8, 10, or 12 hrs post administration. The peak transient mutant dynamin expression from the DPRA recombinant vector may decrease or abolish proteinuria 12, 24 or 48 hrs post administration. In one embodiment of the invention the peak transient mutant dynamin expression from the DPRA recombinant vector decreases or abolishes podocyte FP effacement and/or cortical actin fibers 12, 24 or 48 hrs post administration.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention.

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., DPRA may be coated in a material to protect the compound from the action of acids and other natural conditions that may inactivate the compound. Preferably the carrier is sterile.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of the compounds, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The present invention therefore provides pharmaceutical compositions comprising one or more DPRAs. These pharmaceutical compositions may be administered orally, rectally, parenterally, intrathecally, intracisternally, intravaginally, intraperitoneally, topically (as by powders, ointments, drops or transdermal patch), bucally, or as an oral or nasal spray. The term "parenteral" as used herein refers to modes of administration which include intravenous, intramuscular, intrathecal, intraperitoneal, intrasternal, subcutaneous and intraarticular injection and infusion. One of ordinary skill will recognize that the choice of a particular mode of administration can be made empirically based upon considerations such as the particular disease state being treated; the type and degree of the response to be achieved; the specific agent or composition employed; the age, body weight, general health, sex and diet of the patient; the time of administration and rate of excretion of the agent or composition; the duration of the treatment; drugs used in combination or coincidental with the specific composition; and like factors well known in the medical arts.

Pharmaceutical compositions of the present invention for parenteral injection may comprise pharmaceutically acceptable sterile aqueous or nonaqueous solutions, dispersions, suspensions or emulsions as well as sterile powders for reconstitution into sterile injectable solutions or dispersions just prior to use. Illustrative examples of suitable aqueous and nonaqueous carriers, diluents, solvents or vehicles include, but are not limited to, water, ethanol, polyols (such as glycerol, propylene glycol, polyethylene glycol, and the like), carboxymethylceuulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention may also contain preservatives, wetting agents, emulsifying agents, and dispersing agents. Prevention of the action of microorganisms may be ensured by the inclusion of various antibacterial and antifungal agents, for example, parabens, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the therapeutic agent, it is desirable to slow the absorption from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Solid dosage forms for oral administration include, but are not limited to, capsules, tablets, pills, powders, and granules. In such solid dosage forms, the active compounds are preferably mixed with at least one pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents as appropriate.

Solid compositions of a similar type may also be employed as fillers in soft and hard filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Illustrative examples of embedding compositions which can be used include polymeric substances and waxes.

The active DPRAs can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions may also contain adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

In some embodiments of the invention the DPRA is administered in the form of liposomes. As is known to those skilled in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the DPRA, stabilizers, preservatives, excipients, and the like. Preferred lipids are phospholipids and phosphatidyl cholines (lecithins), both natural and synthetic. Methods to form liposomes are known in the art. See, e.g., Prescott, ed., METHODS IN CELL BIOLOGY, Volume XIV, Academic Press, New York, N.Y. (1976), p. 33 et seq.

One of ordinary skill will appreciate that effective amounts of the therapeutic agents used in the methods of the invention can be determined empirically and may be employed in pure form or, where such forms exist, in pharmaceutically acceptable salt, ester or prodrug form. The therapeutic agents may be administered in compositions in combination with one or more pharmaceutically acceptable excipients. It will be understood that, when administered to a human patient, the total daily usage of the agents and compositions of the present invention will be decided by the attending physician within the scope of sound medical judgment. The specific therapeutically effective dose level for any particular patient will depend upon a variety of factors including the type and degree of the response to be achieved; the specific agent or composition employed; the age, body weight, general health, sex and diet of the patient; the time of administration, route of administration, and rate of excretion of the agent or composition; the duration of the treatment; drugs (such as a chemotherapeutic agent) used in combination or coincidental with the specific composition; and like factors well known in the medical arts.

Techniques of dosage determination are well known in the art. For example, satisfactory results are obtained by oral administration of therapeutic dosages on the order of from 0.05 to 10 m g/kg/day, preferably 0.1 to 7.5 m g/kg/day, more preferably 0.1 to 2 m g/kg/day, administered once or, in divided doses, 2 to 4 times per day. On administration parenterally, for example by i.v. drip or infusion, dosages on the order of from 0.01 to 5 m g/kg/day, preferably 0.05 to 1.0 m g/kg/day and more preferably 0.1 to 1.0 m g/kg/day can be used. Suitable daily dosages for patients are thus on the order of from 2.5 to 500 m g p.o., preferably 5 to 250 mg per oral (p.o.), more preferably 5 to 100 mg p.o., or on the order of from 0.5 to 250 mg i.v., preferably 2.5 to 125 mg i.v. and more preferably 2.5 to 50 mg i.v.

The administration of the agents of the present invention may be for either prophylactic or therapeutic purpose. When provided prophylactically, the agent is provided in advance of any damage i.e., proteinuria or podocyte damage. The prophylactic administration of the agent serves to prevent or reduce the rate of onset of symptoms. When provided therapeutically, the agent is provided at (or after) the onset of the appearance of symptoms of actual disease. The therapeutic administration of the agent serves to reduce the severity and duration of proteinuria.

The compositions of the invention are administered in effective amounts. An "effective amount" is that amount of any of the compositions provided herein that alone, or together with further doses, results in the desired response, e.g. reduces proteinuria or treats a malignancy in a subject. This may involve only slowing the progression of the disease temporarily, although more preferably, it involves halting the progression of the disease permanently. This can be monitored by routine methods. The desired response to treatment of the disease or condition also can be delaying the onset or even preventing the onset of the disease or condition. An amount that is effective can be the amount of a DPRA alone which results in the desired therapeutic endpoint. An amount that is effective is also the amount of a DPRA in combination with another agent that results in the desired result.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

The doses of DPRAs administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Based upon the composition, the dose can be delivered continuously, such as by continuous pump, or at periodic intervals. Desired time intervals of multiple doses of a particular composition can be determined without undue experimentation by one skilled in the art. Other protocols for the administration of the compositions provided will be known to one of ordinary skill in the art, in which the dose amount, schedule of administration, sites of administration, mode of administration and the like vary from the foregoing.

Administration of DPRAs compositions to mammals other than humans, e.g. for testing purposes or veterinary therapeutic purposes, is carried out under substantially the same conditions as described above.

The compositions of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders. As used herein, the term "subject" is used interchangeably with the term "patient" and is intended to include humans and non-human animals including but not limited to a dog, cat, horse, cow, pig, sheep, goat, or primate, e.g., monkey. Preferred patients include a human patient having a disorder characterized by proteinuria, cortical actin, cancer etc. such disorders are included in the definition of "disorders characterized by proteinuria."

As used herein "a patient in need thereof" refers to any patient that is affected with a disorder characterized by proteinuria. In one aspect of the invention "a patient in need thereof" refers to any patient that may have, or is at risk of having a disorder characterized by proteinuria. In one embodiment of the invention "a patient in need thereof" is a patient that has, may have or is at risk at having cancer, precancer, refractory cancer or metastatic cancer. In yet another embodiment of the invention "a patient in need thereof" is a patient that has, may have, or is at risk of having a cognitive disorder, such as Alzheimer's disease or dementia.

The compositions provided of the present invention can be used in conjunction with other therapeutic treatment modalities. Such other treatments include surgery, radiation, cryosurgery, thermotherapy, hormone treatment, chemotherapy, vaccines, and immunotherapy.

The invention also relates in some aspects to the identification and testing of candidate agents and molecules that can modulate the dynamin-dynamin interaction. These molecules are referred to as putative modulators of dynamin-dynamin interactions. The putative modulators can be screened for DPRA type activity using the same type of assays as described herein (e.g., the FLIM assays described in the Examples section). Using such assays, additional DPRA can be can be identified.

Putative modulators include small molecules, nucleic acids, peptides and/or chemicals that modulate dynamin-dynamin interactions. The putative modulators may be identified using the assays provided herein, including those in the Examples section. For example, a putative modulator may be tested for its ability to induce dynamin-dynamin multimerization. To test the ability of a putative modulator to induce dynamin-dynamin multimerization, dynamin peptides may be contacted with the putative modulator and the level of multimerization of dynamin can be compared to the level of multimerization in the absence of the putative modulator.

The invention further provides efficient methods of identifying pharmacological agents or lead compounds for DPRAs. Generally, the screening methods involve assaying for compounds which modulate (up- or down-regulate) the level of dynamin protease resistance. As will be understood by one of ordinary skill in the art, the screening methods may measure the level of binding between the molecules directly, such as by using the methods employed in the Examples. In addition, screening methods may be utilized that measure a secondary effect of the DPRA, for example the level of proteinuria in a cell or tissue sample or even assays that directly detect cleavage of dynamin when exposed to a protease.

A wide variety of assays for pharmacological agents can be used in accordance with this aspect of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Putative modulators useful in accordance with the invention encompass numerous chemical classes, although typically they are organic compounds. Preferably, the putative modulators are small organic compounds, i.e., those having a molecular weight of more than 50 yet less than about 2500, preferably less than about 1000 and, more preferably, less than about 500. Putative modulators comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The putative modulators can comprise cyclic carbon or heterocyclic structure and/or aromatic or polyaromatic structures substituted with one or more of the above-identified functional groups. Putative modulators also can be biomolecules such as peptides, saccharides, fatty acids, sterols, isoprenoids, purines, pyrimidines, derivatives or structural analogs of the above, or combinations thereof and the like. Where the putative modulator is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Biopsy cells and tissues as well as cell lines grown in culture are useful in the methods of the invention.

Putative modulators are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as antimicrobial agents, and the like may also be used.

The present invention further includes DNA vectors which contain the DNA sequences described above and below. In particular, these may be vectors in which the DNA molecules described are functionally linked to control sequences which allows expression of the corresponding polypeptides. These are preferably plasmids.

The invention also includes host organisms transformed with the above vectors. Expression in prokaryotes and eukaryotes may be carried out using techniques known in the art. The DNA sequences according to the invention may be expressed as fusion polypeptides or as intact, native polypeptides. Fusion proteins may advantageously be produced in large quantities. They are generally more stable than the native polypeptide and are easy to purify. The expression of these fusion proteins can be controlled by normal host DNA sequences.

The prerequisite for producing intact native polypeptides using $E.$ $coli$ is the use of a strong, regulatable promoter and an effective ribosome binding site. Promoters which may be used for this purpose include the temperature sensitive bacteriophage $\lambda p_L$-promoter, the tac-promoter inducible with IPTG or the T7-promoter. Numerous plasmids with suitable promoter structures and efficient ribosome binding sites have been described, such as for example pKC30 ($\lambda p_L$; Shimatake and Rosenberg, Nature 292:128 (1981), pKK173-3 (tac, Amann and Brosius, Gene 40:183 (1985)) or pET-3 (T7-promoter (Studier and Moffat, J. Mol. Biol. 189:113 (1986)).

A number of other suitable vector systems for expressing the DNA according to the invention in $E.$ $coli$ are known from the prior art and are described, for example, in Sambrook et al., Molecular Cloning: A Laboratory Manual, Cold Spring Harbor Laboratory Press (1989)).

Suitable $E.$ $coli$ strains which are specifically tailored to a particular expression vector are known to those skilled in the art (Sambrook et al., Molecular Cloning: A Laboratory Manual, Cold Spring Harbor Laboratory Press (1989)). The experimental performance of the cloning experiments, the expression of the polypeptides in $E.$ $coli$ and the working up and purification of the polypeptides are known and are described, for example, in Sambrook et al., Molecular Cloning: A Laboratory Manual, Cold Spring Harbor Laboratory Press (1989). In addition to prokaryotes, eukaryotic microorganisms such as yeast may also be used.

For expression in yeast, the plasmid YRp7 (Stinchcomb et al. Nature 282:39 (1979); Kingsman et al., Gene 7:141 (1979); Tschumper et al., Gene 10:157 (1980)) and the plasmid YEp13 (Bwach et al., Gene 8:121-133 (1979)) are used, for example. The plasmid YRp7 contains the TRP1-gene which provides a selection marker for a yeast mutant (e.g., ATCC No. 44076) which is incapable of growing in tryptophan-free medium. The presence of the TRP1 defect as a characteristic of the yeast strain used then constitutes an effective aid to detecting transformation when cultivation is carried out without tryptophan. The same is true with the plasmid YEp13, which contains the yeast gene LEU-2, which can be used to complete a LEU-2-minus mutant.

Other suitable marker genes for yeast include, for example, the URA3- and HIS3-gene. Preferably, yeast hybrid vectors also contain a replication start and a marker gene for a bacterial host, particularly $E.$ $coli$, so that the construction and cloning of the hybrid vectors and their precursors can be carried out in a bacterial host. Other expression control sequences suitable for expression in yeast include, for example, those of PHO3- or PHO5-gene.

Other suitable promoter sequences for yeast vectors contain the 5'-flanking region of the genes of ADH I (Ammerer, Methods of Enzymology 101:192-210 (1983)), 3-phosphoglycerate kinase (Hitzeman et al., J Biol. Chem. 255:2073 (1980)) or other glycolytic enzymes (Kawaski and Fraenkel, BBRC 108:1107-1112 (1982)) such as enolase, glycerinaldehyde-3-phosphate-dehydrogenase, hexokinase, pyruvate-decarboxylase, phosphofructokinase, glucose-6-phosphate isomerase, phosphoglucose-isomerase and glucokinase. When constructing suitable expression plasmids, the termination sequences associated with these genes may also be inserted in the expression vector at the 3'-end of the sequence to be expressed, in order to enable polyadenylation and termination of the mRNA.

Generally, any vector which contains a yeast-compatible promoter and origin replication and termination sequences is suitable. Thus, hybrid vectors which contain sequences homologous to the yeast $2\mu$ plasmid DNA may also be used. Such hybrid vectors are incorporated by recombination within the cells of existing $2\mu$-plasmids or replicate autonomously.

In addition to yeasts, other eukaryotic systems may, of course, be used to express the polypeptides according to the invention. Since post-translational modifications such as disulphide bridge formation, glycosylation, phosphorylation and/or oligomerization are frequently necessary for the expression of biologically active eukaryotic proteins by means of recombinant DNA, it may be desirable to express the DNA according to the invention not only in mammalian cell lines but also insect cell lines.

Functional prerequisites of the corresponding vector systems comprise, in particular, suitable promoter, termination and polyadenylation signals as well as elements which make it possible to carry out replication and selection in mammalian cell lines.

In a preferred embodiment of the invention particularly suitable promoters are podocyte specific promoters. A podocyte specific promoter is one that is expressed exclusively in podocytes, such as the podocin promoter.

For expression of the DNA molecules according to the invention it is particularly desirable to use vectors which are replicable both in mammalian cells and also in prokaryotes such as $E.$ $coli$. Vectors derived from viral systems such as SV40, Epstein-Barr-virus, etc., include, for example, pTK2, pSV2-dhfv, pRSV-neo, pKO-neo, pHyg, p205, pHEBo, etc. (Sambrook et al., Molecular Cloning: A Laboratory Manual, Cold Spring Harbor Press, N.Y. (1989)).

After transformation in suitable host cells, e.g. CHO cells, corresponding transformed cells may be obtained with the aid of selectable markers (thymidine-kinase, dihydrofolate-reductase, green fluorescent protein, etc.) and the corresponding polypeptides are isolated after expression. The host cells suitable for the vectors are known, as are the techniques for transformation (micro-injection, electroporation, calcium phosphate method, etc.) as described, for example, in Sambrook et al., Molecular Cloning: A Laboratory Manual, Cold Spring Harbor Press, N.Y. (1989).

For cloning corresponding DNA fragments in prokaryotic or eukaryotic systems, the selected vector may be cut, for example, with a restriction endonuclease and, optionally after modification of the linearized vector thus formed, an expression control sequence equipped with corresponding restriction ends is inserted. At the 3'-end (in the direction of translation) the expression control sequence contains the recognition sequence of a restriction endonuclease, so that the vector already containing the expression control sequence is digested with the said restriction enzyme and the DNA molecule according to the invention, provided with ends which fit, can be inserted. It is advantageous to cleave the vector which already contains the expression control sequence with a second restriction endonuclease inside the vector DNA and to insert the DNA molecule provided with the correct ends into the vector fragment produced. The techniques required are described, for example, by Sambrook et al. Molecular Cloning: A Laboratory Manual Cold Spring Harbor Press. N.Y. (1989).

Apart from the DNA molecules specified, the invention also relates to processes for preparing the vectors described herein, particularly expression vectors. These vectors are characterized in that a DNA provided with corresponding ends and coding for a functional derivative or a fragment of the DPRA protein is inserted into a vector DNA cut with restriction endonucleases and containing the expression control sequences described by way of example, in such a way that the expression control sequences regulate the expression of the DNA inserted. The peptides and antibody agents of the present invention which are obtained by the expression of recombinant DNA or from the native receptor molecule may, of course, also be derivatized by chemical or enzymatic processes.

A further aspect of the present invention relates to the screening of combinatorial libraries of compounds comprising small molecules for biological activity related to aspects of the invention, e.g. in assays based on inhibition of cytoplasmic cathepsin L activity and in animal models of disease associated with kidney disease, podocyte pathology etc. Such combinatorial libraries are readily available to the skilled artisan and can be obtained either from commercial vendors or by synthetic methods.

Also within the scope of the invention are kits comprising the compositions of the invention and instructions for use. The kits can further contain at least one additional reagent, such as a chemotherapeutic agent. Other kits can include the dynamin multimers.

A kit may comprise a carrier being compartmentalized to receive in close confinement therein one or more container means or series of container means such as test tubes, vials, flasks, bottles, syringes, or the like. A first of said container means or series of container means may contain one or more dynamin mutants or recombinant vectors for the expression thereof. A second container means or series of container means may contain a second therapeutic, such as, cytotoxic drug or dynamin antibodies (or fragment thereof).

Kits for use in the therapeutic methods of the invention containing the dynamin conjugated to other compounds or substances can be prepared. The components of the kits can be packaged either in aqueous medium or in lyophilized form. When the dynamin or fragments thereof are used in the kits in the form of conjugates in which a label or a therapeutic moiety is attached, such as a radioactive metal ion or a therapeutic drug moiety, the components of such conjugates can be supplied either in fully conjugated form, in the form of intermediates or as separate moieties to be conjugated by the user of the kit.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Active Dynamin is Required for Kidney Ultrafiltration and can be Alternatively Switched Off by Extralysosomal Cathepsin L in Renal Disease Dynamin:GTP is Required for Maintenance of Actin Stress Fibers in Podocytes.

Figure 1A:
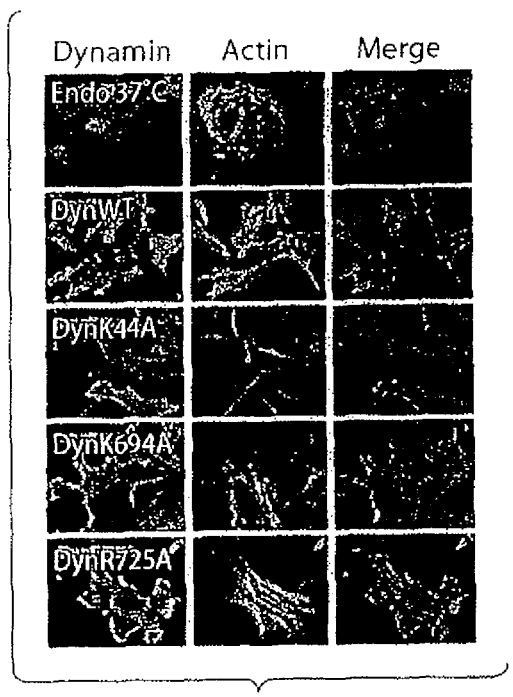
FIG. 1 is a panel of immunostaining images (A, C, D) and a bar graph (B), showing that GTP-bound dynamin regulates podocyte actin cytoskeleton organization and motility independent from endocytosis. A) Endogenous dynamin is located in punctuated pattern throughout the cytoplasm of differentiated podocytes which have thick stress fibers that do not co localize with dynamin. Adenoviral overexpression of wild type dynamin is distributed throughout the cells and does not change stress fiber organization of actin. Dominant negative dynamin K44A leads to loss of stress fibers and formation of a predominantly cortical actin cytoskeleton which co localizes with dynamin. Dynamin K694A displays actin stress fibers which do not overlap with dynamin. Expression of dynamin R725A activator is strongly associated with podocyte membranes and induces stress fibers. B) Treatment of cultured podocytes with lipopolysaccharide (LPS) or puromycin aminonucleoside (PAN) is associated with disruption of actin stress fibers. Dynamin R725A (SEQ ID NO. 4) can prevent the loss of stress fibers after LPS or purine aminonucleoside (PAN) administration. C) Differentiated podocytes heavily endocytose under control conditions which is unchanged after overexpression of wild type dynamin. K44A disrupts endocytosis. K694A, R725A but also LPS treated podocytes have no evident impairment in endocytosis suggesting that the presence of stress fibers in podocytes is not necessary to maintain endocytosis. D) Podocyte motility is increased from baseline in control podocytes, wild type dynamin overexpressing as well as podocytes expression the endocytosis-activating dynamin mutant K694A. Of note, expression of dynamin K44A is associated with a significant increase in baseline podocyte motility. The expression of R725A (SEQ ID NO. 4) reduces baseline podocyte migration and abrogates the migratory response as response to PAN.
Figure 1B:
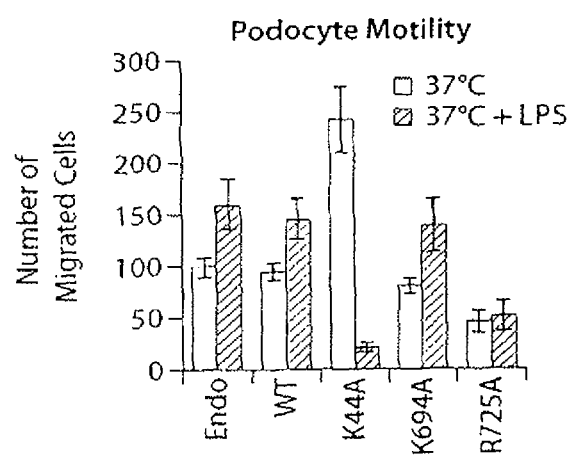
Figure 1C:
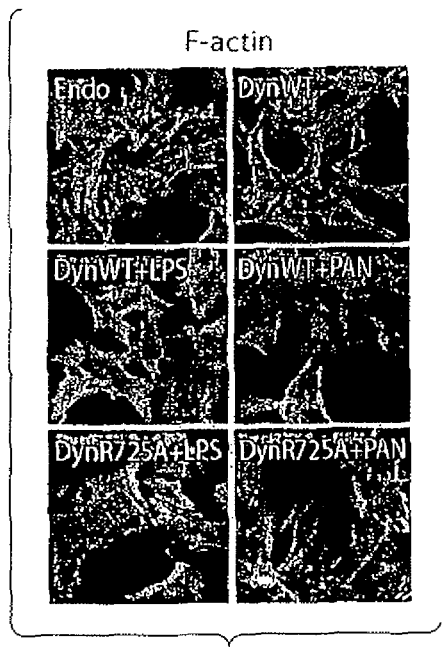
Figure 1D:
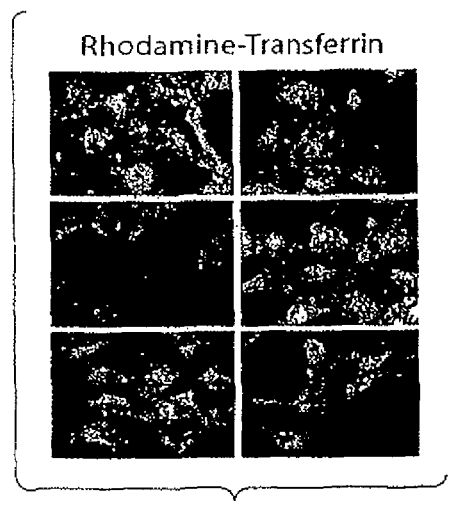
Figure 2A:
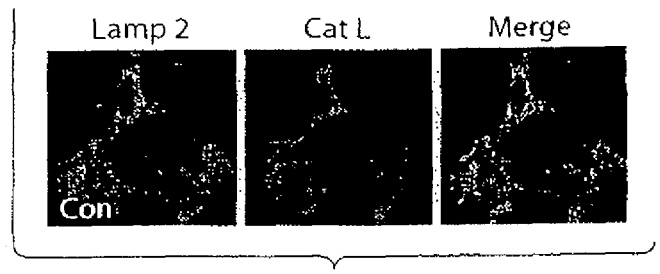
FIG. 2 is a panel of immunostaining images (A-L, N) and a bar graph (M), showing that active extralysosomal cathepsin L is induced in podocytes during proteinuric kidney disease and co localizes with dynamin. A) Cultured podocytes express the lysosomal marker Lamp 2 and most of the cathepsin L is confined to Lamp 2 positive compartments resulting in a yellow overlap. B) LPS treatment of cultured podocytes does not change Lamp 2 expression (left panel) but induces cathepsin L which is now also present outside Lamp 2 positive compartments. C) Cathepsin L activity is low in untreated cultured podocytes and found inside Lamp 2 positive lysosomes. D) LPS treatment induces cathepsin L activity which is now mainly localized outside Lamp 2 positive lysosomes (white arrows). E) Cathepsin L activity does not colocalize with dynamin in control podocytes. F) LPS treatment of cultured podocytes results in active extralysosomal cathepsin L which can partially colocalize with dynamin preferentially at the cell membrane (white arrows). G) Control mice express low levels of glomerular cathepsin L. H) The induction of proteinuria by LPS injection induces cathepsin L within the glomerulus. I) Immunogold labeling of cathepsin L localizes the enzyme in the cell body of podocytes but also in podocyte foot processes. J) Cathepsin L expression is induced after LPS injection and concentrated in effaced podocyte foot processes. K) Mice lacking cathepsin L have normal podocyte foot process architecture. L) Cathepsin L-/- are protected from LPS induced podocyte foot process effacement. M) Taqman Real-time PCR shows that glomerular cathepsin L mRNA was upregulated in human proteinuric kidney diseases. MCD=Minimal Change Disease, MGN=Membranous Glomerulonephritis, FSGS=Focal Segmental Glomerulosclerosis, and DN=diabetic nephropathy. Values were presented as Mean±SEM. * $p<0.05$ for MCD, MGN, FSGS or DN versus control patients. N) Cathepsin L can colocalize in podocyte foot processes with dynamin.
Figure 2B:
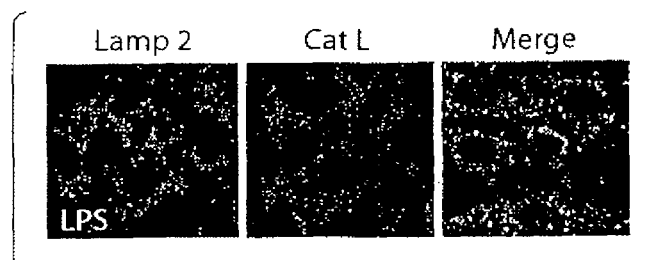

This study examined the role of dynamin in actin dynamics of podocytes. An adenoviral expression system was utilized to obtain expression of various dynamin mutants with more than 90% infection efficiency in cultured differentiated mouse podocytes and analyzed the organization of the actin cytoskeleton, their migratory and endocytotic behavior (FIG. 1). In fully differentiated podocytes actin is organized in parallel bundles of stress fibers (FIG. 1A, panel Endo), which do not co localize with endogenous dynamin. Overexpression of dynWT did not dramatically alter stress fiber pattern in podocytes (FIG. 1A, panel dynWT). In contrast, overexpression of the dominant-negative dynamin, dynK44A, mutant that cannot bind GTP, resulted in the loss of stress fibers and their rearrangement into a cortical actin cytoskeleton (FIG. 1A, dynK44A). This type of actin rearrangement in cultured podocytes is resembling actin rearrangement in damaged podocytes during proteinuria in situ (Smoyer and Mundel, 1998). These data suggest that membrane remodeling by actin in podocytes requires GTP-bound dynamin. Thus, the consequence on actin dynamics in podocytes was examined when dynamin is hyperactive by expressing known dominant activators, dynK694A and dynR725A (SEQ ID NO. 4). Both mutants are predicted to live longer in the GTP-bound form. Overexpression of dynK694A did not dramatically change actin stress fibers in podocytes (FIG. 1A, panel dynK694A). In contrast, expression of dynR725A (SEQ ID NO. 4), significantly induced stress fibers formation (FIG. 1, panel dynR725A). To further examine this surprising phenotype in a biological context, motility assays were performed next using a modified Boyden Chamber assay. As shown in FIG. 2B, overexpression of dynWT or dynK694A did not change podocyte motility when compared to control cells. In contrast, overexpression of dynR725A (SEQ ID NO. 4) significantly decreased podocyte motility, whereas overexpression of dynK44A dramatically increased cell motility. Thus, loss of stress fibers (dynK44A phenotype) lead to increase in cellular motility, whereas increase in stress fibers had an opposite effect (dynR725A phenotype). Cells overexpressing dynK44A have a similar phenotype and exhibit a migratory response as described in other in vitro models of podocyte injury.

Figure 2C:
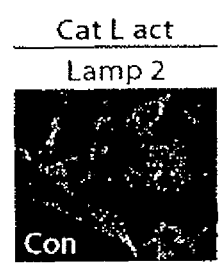

Next the it was examined if LPS treatment which causes proteinuria and podocyte FP effacement in mice would also increase motility of cultured podocytes. Indeed, LPS treatment of podocytes lead to an increase in podocyte motility. However, LPS treatment did not increase cell motility if cells were expressing dynR725A. Therefore it was explored if increased podocyte motility is associated with a decrease in podocyte stress fibers and treated dynWT expressing podocytes with LPS or PAN (FIG. 2C). Under both conditions a marked decline of stress fibers was observed and the disappearance of a cortical actin cytoskeleton when compared to untreated control podocytes (FIG. 2C, panels endo, dynWT). The expression of dynR725A during LPS and PAN treatment prevented the loss of actin stress fibers which appeared increased to the levels in untreated cells expressing endogenous dynamin or dynWT (compared to phalloidin labeling in FIG. 1C, panel dynWT with FIG. 1C). Functionally, cell motility directly correlated with the organization of the actin cytoskeleton in podocytes; fast motility equaled reorganization from stress fibers into cortical actin, slow motility equaled formation of stress fibers. DynR725A can prevent loss of stress fibers under podocyte damage conditions (LPS, PAN) but it can also increase their formation, which has a functional consequence in reduction of podocyte motility.

The Effect of Dynamin on the Actin Cytoskeleton is Independent from Endocytosis.

Since dynamin is known to play a major role in regulation of clathrin-mediated endocytosis, it appeared possible that the observed actin phenotypes as described above were indirect consequence of changes in endocytosis. As shown in FIG. 1D, overexpression of dynWT did not enhance the overall transferring uptake compared to the control podocytes. Overexpression of dynK44A completely inhibited transferring uptake (in FIG. 2B, panel K44A, notice lack of rhodamine staining within recycling endosomes). Overexpression of dynK694A lead to increase in transferring uptake, whereas overexpression of dynR725A exhibited the wild-type levels of endocytosis (Sever et al., 2000a). While LPS treatment of cells overexpressing dynWT had no effect on endocytosis of rhodamine-transferrin (FIG. 1D), it did induce cell motility and changes in actin cytoskeleton. Therefore, loss of stress fibers was not necessarily associated with reduction in endocytosis (dynK44a vs. dynWT+LPS). Taken together, the effects of dynamin mutants on the actin cytoskeleton were independent from changes in endocytosis, and suggested that dynamin directly regulates actin dynamics in podocytes.

LPS Increases Cathpesin L Expression and Activity in Cultured Podocytes, Mice and in Patients with Glomerular Disease.

Figure 2D:
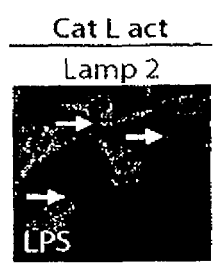
Figure 2E:
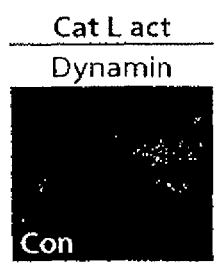
Figure 2F:
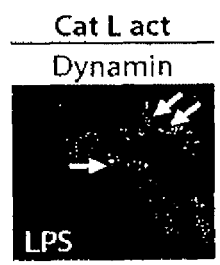

In this study the expression and activity of cathepsin L in cultured podocytes was examined. As shown in FIG. 2A, cathepsin L predominantly co-localizes with the lysosomal associated membrane protein, Lamp 2 in lysosomes. Treatment of cultured podocytes with LPS for 24 hours did not change Lamp 2 expression, but strongly induced the expression of cathepsin L, which was also found outside lysosomes (FIG. 2B, arrows). To visualize the subcellular sites of cathepsin L activity, a fluorogenic substrate was used CV-(FR)2, which emits fluorescence light upon cleavage by cathepsin L (Almeida et al., 2001). In non-treated podocytes, cathepsin L activity was confined within lysosome whose presence is marked by staining for Lamp 2 (FIG. 2C). LPS treatment increased overall cathepsin L activity, which now extended far into podocyte processes (FIG. 2D, arrows). Next it was analyzed if active cathepsin L can colocalize with dynamin. Untreated control cells which overexpressed dynWT showed no detectable colocalization between dynamin and cathepsin L (FIG. 2E). Upon LPS treatment, there was a partial overlap of cathepsin L activity with dynamin (FIG. 2F, arrows), a finding that was an indication that dynamin may be processed by cathepsin L under disease conditions.

Figure 2G:
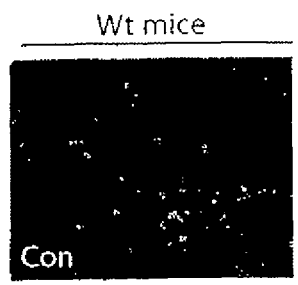
Figure 2H:
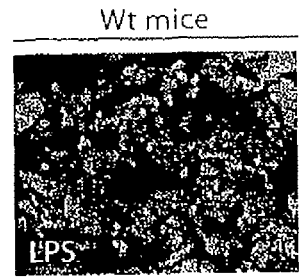
Figure 2I:
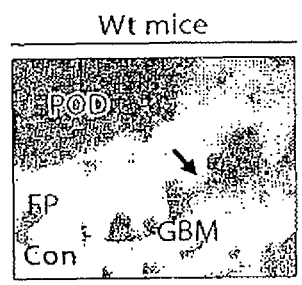
Figure 2J:
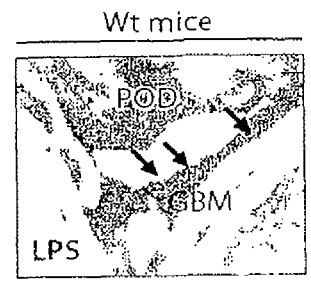
Figure 2K:
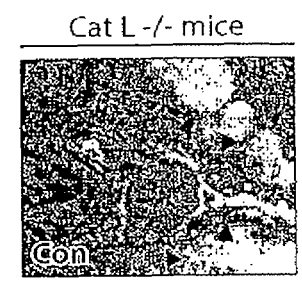
Figure 2L:
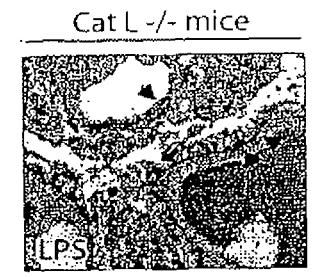
Figure 2M:
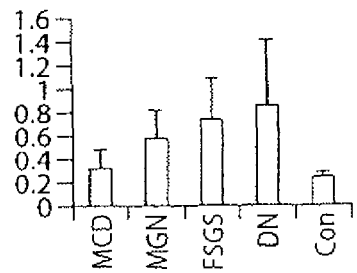

Immunocytochemistry of cathepsin L in frozen mouse kidney sections was also performed. While control kidneys showed only minimal glomerular cathepsin L expression (FIG. 2G), the injection of a single dose of LPS induced glomerular cathepsin L expression (FIG. 2H). LPS treatment resulted in severe FP effacement (FP morphology between FIGS. 2I and 2J). Subcellular localization of cathepsin L in podocytes using immunogold electron microscopy identified cathepsin L antigenic sites within the cell body of the control podocytes (FIG. 2I, arrow), as well as in low abundancy in podocyte FPs. LPS treatment of wt mice induced FP effacement and cathepsin L which was strongly found within effaced podocyte FP (FIG. 2J). Next it was examined if the presence of cathepsin L was essential for FP effacement seen in wt mice after LPS injection. Cathepsin L knockout mice exhibit normal podocyte morphology and have no overt functional defect in the kidney (FIG. 2K), (Roth et al., 2000). LPS treatment of cathepsin L−/− mice failed to induce FP effacement (FIG. 2L) as well as proteinuria (0.25±0.11 mg/ml), demonstrating requirement of cathepsin L in mediating this event.

Figure 2N:
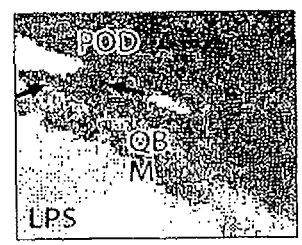

Next the role of cathepsin L in human proteinuric kidney disease with podocyte damage was studied. To this end, quantitative PCR was performed of mRNA from isolated glomeruli (Cohen et al., 2002) encoding for cathepsin L from patients with different etiologies of proteinuric kidney disease. Surprisingly, four types of proteinuric kidney disease all involving podocyte FP effacement (minimal change disease (MCD), membranous glomerulonephritis (MGN), focal segmental glomerulosclerosis (FSGS) and diabetic nephropathy (DN)) had an increase in the mRNA encoding for cathepsin L. Together, these data show that proteolytic activity of cathepsin L outside lysosomes plays a major role in glomerular disease, and that maybe dynamin is its primary target. To determine whether dynamin could localize together with cathepsin L in podocytes during kidney disease, double immunogold labeling was performed using 10 nm gold particles recognizing a monoclonal anti-dynamin antibody and 15 nm gold particles to bind to polyclonal anti-cathepsin L antibody. As shown in FIG. 2N, both antigenic sites are present within podocyte FPs during LPS induced podocyte FP effacement. Of note, cathpesin L antigenic sites are also present within GBM, in endothelial cells and cell body. Together, these data demonstrated that cathepsin L can come in the close vicinity with dynamin in podocytes in vivo supporting the idea that cathepsin L can cleave dynamin.

Loss of Dynamin in Podocytes is a Hallmark During the Development of Proteinuria.

Figure 3A:
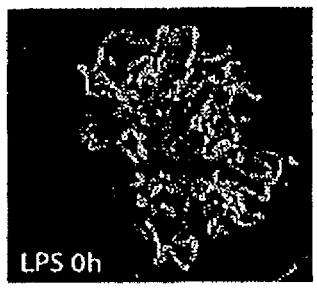
FIG. 3 is a panel of immunostaining images depicting the expression of dynamin in kidney glomerulus under normal and proteinuric conditions.
A) Dynamin is strongly expressed in normal mouse glomerulus in a pattern characteristic for podocytes. B) LPS treatment leads to a strong reduction in glomerular dynamin after 24 hours. C) Dynamin expression is recovered after the resolution of proteinuria 72 hours after LPS injection. D) Immunogold analysis of frozen mouse kidney reveals localization of dynamin in podocyte foot processes in close vicinity to the slit diaphragm. Few gold particles are also found in glomerular endothelial cells. E) Control rats express dynamin in the glomerulus. F) 4 days after PAN injection, there is a significant decline in dynamin staining. G) 8 days after PAN injection, glomerular dynamin expression starts to recover. H) Dynamin expression is recovered after resolution of proteinuria and reformation of podocyte foot processes on day 28. I) Immunoperoxidase labeling of human kidneys show strong dynamin labeling in proximal tubular cells as well as in podocytes within the glomerulus (black arrows). J) In kidneys with Minimal Change Disease, there is a selective reduction of dynamin staining within glomerular podocytes, whereas expression in proximal tubular cells is still preserved (stars). K) The lack of cathepsin L in mice is associated with strong dynamin staining in podocytes L) Cathepsin L deficient mice are protected from LPS induced downregulation of dynamin in podocytes (red arrows).
Figure 3B:
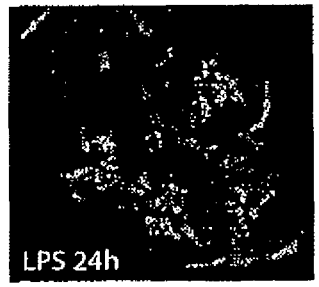
Figure 3C:
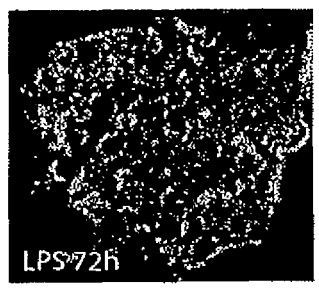
Figure 3D:
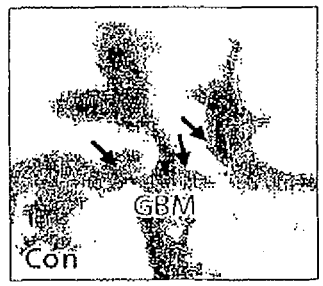

This experiment examined if dynamin staining in the glomerulus is changing during kidney disease. Thus, wt mice were injected with LPS and the presence of dynamin was analyzed during the course of the reversible podocyte FP effacement and proteinuria by immunocytochemistry using the monoclonal anti-dynamin antibody (hudy1). As shown in FIG. 3A, dynamin staining was present within glomeruli in a pattern suggestive of podocytes. LPS treatment for 24 hours, which is known to cause podocyte foot processes (FP) effacement and proteinuria (Reiser et al., 2004b) led to a strong reduction of dynamin staining (FIG. 3B). Dynamin reappeared in glomeruli of mice recovering from LPS induced proteinuria (FIG. 3C). LPS treatment does not change staining pattern for the podocyte protein, synaptopodin (Mundel et al., 1997a) suggesting that loss of dynamin staining might be one of the first markers for podocyte FP effacement in this model. To analyze the subcellular localization of dynamin in normal podocytes, immunogold electron microscopy was performed. Mice kidney cortex was incubated with monoclonal anti-dynamin antibodies and then labeled with 10 nm gold particles. As shown in FIG. 3D, dynamin antigenic sties are concentrated in podocyte FP, sometimes in close vicinity to the cytoplasmic site of the slit diaphragm. This site has been implicated in hosting proteins that drive actin rearrangement in FP (Shih et al., 2001). Thus, endogenous dynamin localization is in agreement with its major role in organizing actin in podocyte FP.

Figure 3E:
Figure 3F:
Figure 3G:
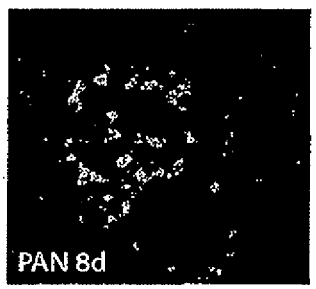
Figure 3H:
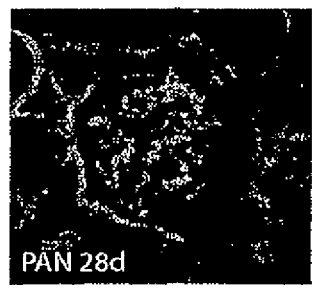
Figure 3I:
Figure 3J:
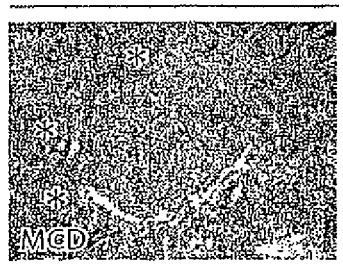
Figure 3K:
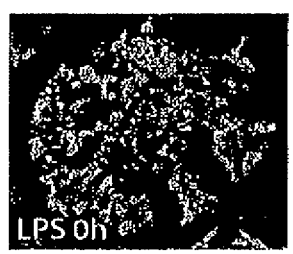
Figure 3L:

Next, dynamin expression in the PAN model of reversible FP effacement and proteinuria was explored (Shirato I et al., 1996). Control rats have a strong glomerular dynamin labeling (FIG. 3E). Proteinuria was induced in rats by the single injection of PAN. In the induction of proteinuria and FP effacement on day 4 there was a significant decline in podocyte glomerular dynamin staining (FIG. 3F). This expression was still decreased on day 8 (peak phase of proteinuria), (FIG. 3G), and was recovering on day 28, which constitutes the resolution phase of proteinuria and FP effacement in this model (FIG. 3H). Thus, both rodent models for glomerular disease showed reversible loss of dynamin staining that correlated with maximal proteinuria. These animal models most closely resemble Minimal Change Disease (MCD) in humans. The term minimal change disease comes from the notion that morphological podocyte changes are only visible by electron microscopy. Functionally, MCD is a glomerular disorder characterized by reversible podocyte FP effacement and proteinuria. Thus, the expression of dynamin by staining human biopsy samples with anti-dynamin antibodies was next examined. As shown in FIG. 3I, healthy kidneys show strong labeling for dynamin in glomeruli, which correlates with observed dynamin staining in rodents (podocytes are indicated by arrows in FIGS. 3I and 3J). In striking contrast, there was no detectable dynamin staining in glomeruli from patients diagnosed with MCD (FIG. 3J). Importantly, staining pattern for dynamin in proximal tubules is unchanged (compare the regions in FIGS. 2D and 2D' indicated by asterix), showing specificity for dynamin loss in glomeruli. Thus, loss of dynamin staining in MCD correlates with loss of dynamin staining in animal models for podocyte injury/effacement. Having established the oppositional expression pattern of high cathepsin L with reduced dynamin in podocytes, the presence of dynamin is stable in cathepsin L−/− mice after LPS injection was examined Control mice and mice lacking cathepsin L were injected with LPS. 24 h after injection, we performed immunocytochemistry of frozen kidney sections to study dynamin labeling. As shown in FIG. 3K, red arrows, cathepsin L−/− mice were protected for dynamin loss in podocytes upon LPS treatment, and the animals did not develop proteinuria. Together, these data suggested a possible role of cathepsin L in processing of dynamin during the development of podocyte FP effacement and proteinuria.

Cathepsin L Cleaves Dynamin:GTP In Vitro.

Reinheckel and colleges have developed the bioinformatics tool 'PEPS' (Prediction of Endopeptidase Substrates) to predict endopeptidase cleavage sites. By using PEPS, three putative cathepsin L sites within dynamin were identified (FIG. 4A). To assess whether cathepsin L could cleave dynamin at neutral pH 7.0, recombinant dynamin 1 was incubated with purified cathepsin L (Stressgene) and respective proteolytic fragments were determined using anti-dynamin antibodies that recognize N-terminal GTPase domain (Stressgene). As expected, cathepsin L was not highly active protease at pH 7.0 (FIG. 4). Strikingly, addition of GTP in the assay resulted in significant cleavage of dynamin by cathepsin L (FIG. 4). The most prominent proteolytic fragment traveled with molecular weight of approximately 40 kD. These data suggested that the amino acid sequence situated within the middle domain, was indeed specifically recognized by cathepsin L at neutral pH, but only if dynamin was in its GTP-bound conformation. Addition of GTPγS, non-hydrolyzable GTP homolog abolished dynamin cleavage by cathepsin L. GTPγS has been shown to promote oligomerization of dynamin into higher order structures such as rings or spirals in solution. Thus, self-assembly of dynamin:GTPγS protected from cathepsin L cleavage. The middle domain and the GAP domain mediate dynamin self-assembly into higher order structures. Based on the 3D-structure of self-assembled dynamin determined by cry-EM, the middle and the GAP domains are localized within self-assembled dynamin and thus amino acid sequences situated within either of these domains are predicted to be inaccessible for cathepsin L. Since activity of cathepsin L at pH 7.0 was marginal if GTP was not added in the assay, in order to examine whether GTPγS and thus self-assembly can protect from cathepsin L cleavage in general, assays were performed at lower pHs. As expected, at pH 5.0 and 6.0 cathepsin L potently proteolyzed recombinant dynamin (FIG. 4E). In contrast, in vitro processing of dynamin by cathepsin L was completely inhibited by addition of GTPγS (FIG. 4E), even at pH 5.0, when cathepsin L is at its most active state. Thus, generation of 40 kD fragment upon addition of GTP in the assay and protection of the cleavage by GTPγS are consistent with primary cleavage site for cathepsin L to be present within the middle domain. Furthermore, the data demonstrate that in order to be processed by cathepsin L at the neutral pH dynamin should be in the GTP-bound conformation. These data suggest that cathepsin L might negatively regulate dynamin activity in the cytoplasm.

Cathepsin L Processes Dynamin:GTP In Vivo.

Next, it was examined whether cathepsin L could process dynamin in vivo, and whether this processing required GTP binding by dynamin. To this end, cultured podocytes were infected with adenoviruses expressing dynWT as well as different dynamin mutants. Infected podocytes were subsequently treated with LPS. LPS treatment increases cathepsin L presence and the activity in the cytosol (FIG. 3), and thus is expected to induce generation of the 40 kD proteolytic fragment. Respective cytosols were probed using the GTPase antibodies in order to detect N-terminal 40 kD proteolytic fragment. Expression of dynWT in podocytes treated with LPS identified proteolytic fragments that traveled with the same mobility as fragments observed in vitro. Addition of specific cathepsin L inhibitor (Z-FF-FMK, Calbiochem), to the tissue cultured podocytes treated with LPS resulted specifically in the loss of p40. Importantly, LPS treatment of podocytes expressing dynK44A, enzyme that cannot bind GTP, did not result in detectable levels of p40. Furthermore, significant amount of p40 was present in cells expressing dynR725A prior to LPS treatment. DynR725A is predicted to live longer in the GTP-bound conformation, which can account for increased processivity by cathepsin L. Together, these data are in agreement with requirement for GTP-binding by dynamin to be processed by cathepsin L at neutral pH in vivo. Importantly, LPS treatment of podocytes expressing dynR725A completely abolished presence of the p40. Given complete protection of cathepsin L cleavage by GTPγS, it was reasoned that LPS treatment was somehow inducing dynR725A self-assembly, which in turn was protecting dynR725A from cathepsin L cleavage. This in turn would explain ability of dynR725A to counteract LPS and PAN treatment (FIG. 1D). If this rational was correct, then it suggested that self-assembly of dynWT or dynK694A could not protect dynamin from cathepsin L cleavage and thus counteract LPS treatment. Biochemical difference between dynWT, dynK694A and dynR725A is that only dynR725A is impaired in the rate of GTP-hydrolysis of assembled dynamin. This is important because GTP-hydrolysis drives disassemble of dynamin. Thus, while all three dynamins are predicted to self-assemble by LPS treatment, only dynR725A will stay assembled due to its inability to hydrolyze GTP. Once assembled dynWT and dynK694A hydrolyze GTP they will fall apart and thus become accessible for cathepsin L cleavage.

In order to examine where dynamin processing by cathepsin L was taking place, subcellular fractionation of podocytes in isotonic sucrose was performed. Podocytes expressing dynWT were treated with LPS, and lysates were resolved into particulate and soluble fractions by high speed centrifugation. Total proteins from both fractions were loaded onto SDS-PAGE and Western blot analysis was performed using anti-GTPase antibodies. Overexpressed full-length dynamin was approximately equally distributed between the particulate and the soluble fraction, in agreement with its endogenous distribution. This distribution has been interpreted as dynamin existing in two pools; cytosolic and membrane associated. Tubuline detected with a monoclonal anti-tubuline antibody (Sigma) was used as a control to monitor release of soluble proteins. Importantly, p40 was detected only in the soluble fraction. In contrast, lysosomal protein Lamp 2 as well as cathepsin L, were detected exclusively in the particulate fractions. These data strongly suggest that only dynamin:GTP in the cytoplasm was a target for processing by cathepsin L. There was a significant amount of full-length dynamin present in the both fractions. This can explain normal endocytosis of transferrin receptor in cells treated with LPS. Together, these data suggest that dynamin:GTP is processed by extralysosomal cathepsin L in cultured podocytes. They also suggest that dynamin self-assembly into higher order structures can protect from cathepsin L processing in the cytosol.

Detection of Dynamin Self-Assembly by FLIM.

In order to test the hypothesis that self-assembly of dynamin was protecting its cathepsin L processing in cultured podocytes, dynamin self-assembly in live cells was examined using fluorescence lifetime imaging microscopy (FLIM). FLIM is based on the fluorescence resonance energy transfer (FRET) between the donor and the acceptor that shortens the lifetime of the donor if the acceptor distance is within ≈100 Å (10 nm). Therefore, the detection of shortened lifetimes demonstrates FRET and indicates spatial proximity of the two labeled molecules. A FLIM-assay was developed that specifically detects dynamin self-assembly into the higher order structures in podocytes. The assay is based on overexpressing dynamin in podocytes, and subsequently staining fixed cells with monoclonal anti-dynamin antibodies that have been conjugated with either Alexa-488 (donor florophore) or Alexa-568 (acceptor florophore). Cells are stained by mixing both florophores in equal amounts, and examining lifetime of Alexa-488. As shown in Table 1, when staining is performed using combination of mice monoclonal GTPase-alexa488 antibodies and goat anti-rabbit-alexa568 (GARalexa568) no FRET signal was detected (t1=2417±69). In contrast, labeling cells with GTPase-alexa488 and hudy1-alexa568 resulted in statistically significant shortening of the lifetime of alexa488, demonstrating presence of the FRET (t1=2267±95). Importantly, FRET only occurred in the vicinity of the membrane. This spatially-restricted lifetime shortening in cells suggested that the majority of dynamin oligomerization were occurring at the membrane at the sites of actin dynamics and focal adhesions. Overexpression of an assembly impaired mutant, dynK694A exhibited no detectable FRET measured by FLIM, as well as overexpression of dynR725A (Table 1). Thus, both dominant activating mutants, dynK694A and dynR725A, are impaired for assembly into a supramolecular structures in podocytes under normal conditions. Treating cells with LPS resulted in the loss of FLIM measured FRET, in cells that were overexpressing dynWT (FIG. 4G, panel dynWT+LPS). In contrast, LPS treatment induced dynamin self-assembly for the dominant active dynamin mutant, dynR725A (FIG. 4G, panel dynR725A+LPS). It was noted that self-assembly of dynR725A upon LPS is distributed within the cytosol and does not localize on the junctions between the cells. Loss of FRET measured FLIM correlates with the loss of p40 proteolytic fragment in cultured podocytes. And presence of p40 in cells expressing dynR725A under normal conditions correlates with the lack of dynR725A assembly detected by FLIM. The opposite is true for the dynWT; lack of p40 under control conditions when FLIM is present, and appearance of the p40 upon LPS treatment with no measurable FRET. Together, these data strongly suggest that sequences ELSGGA is cathepsin L recognition sequences in vivo. Since experiments in podocytes suggested specific protection and accessibility of ELSGGA sequences, we have generated dynamin mutant that should not be recognized by cathepsin L; dynL356Q, G358V. Finally, proteolytic processing of dynamin after LPS treatment is also observed in vivo. Homogenates from kidney cytosols before and after LPS treatment of mice, resulted in two major fragments that exhibit the same mobility as in vitro generated fragments.

Transient In Vivo Expression of Dynamin Mutants Affect Podocyte Structure and the Level of Proteinuria.

Figure 5A:
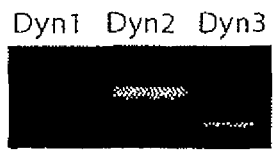
FIG. 5 is a set of gel shifts (A, B), a panel of immunostaining images (C-I), and a bar graph (J) illustrating intravenous gene delivery of dynamin mutants into mice to target podocytes in vivo. A) Podocytes express dynamin 2 and little dynamin 3 mRNA but no neuronal dynamin 1. B) MAB5402 antibody can selectively recognize dynamin 1 used for i.v. gene delivery. C) Immunostaining using MAB5402 reveals dynamin 2 (crossreactivity from antibody). D) 10 hours after gene delivery of dynamin 1 cDNA, there is a strong expression of dynamin 1 protein within the glomerulus and as Bowman's capsule. E) Some of the expressed glomerular dynamin 1 (red) is located in podocytes as shown by double labeling with the podocyte marker synaptopodin (green), resulting in a yellow overlap at podocytes. F) Expression of wild type dynamin gene in podocytes does not affect foot process morphology. G) K44A expression in vivo induces podocyte foot process effacement. H) R725A (SEQ ID NO. 4) expression leads to partial foot process effacement. I) The expression of L356Q, G358V dynamin mutant (SEQ ID NO. 3) does not affect podocyte foot process morphology. J) Course of proteinuria in response to the gene delivery of various dynamin mutants. K44A induced significant amount of proteinuria.
Figure 5B:
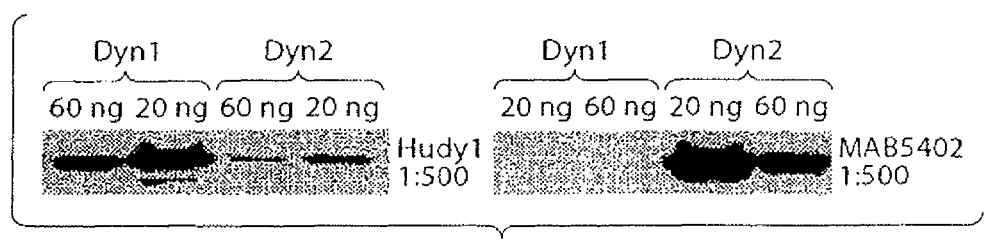

Next it was explored whether gene delivery of dynamin mutants dynR725A and dynL356Q, G358V into mice can be expressed in podocytes and if this procedure can affect podocyte FP architecture and function. First, we needed to establish a safe and reliable detection system of transferred gene expression in podocytes. Therefore we analyzed which dynamin isoforms are expressed in podocytes by RT-PCR. Podocytes express mainly dynamin 2 and little dynamin 3 but no dynamin 1 (FIG. 5A). Gene-transfer CMV promotor driven dynamin 1 constructs were used because neuronal dynamin protein is normally not expressed in podocytes and could be easily tracked by a specific monoclonal dynamin 1 antibody (FIG. 5B). Furthermore, the overexpression of dynamin 2 has been associated with an increase in cell apoptosis, suggesting that cells can better tolerate high levels of dynamin 1 then dynamin 2 Monoclonal dynamin antibodies MAB 5402 (Stressgene) were used, which predominantly recognize dynamin 1 (FIG. 5B). Labeling of glomerular sections with MAB 5402 detected some minimal background labeling of dynamin, representing endogenous dynamin 2

Figure 5C:
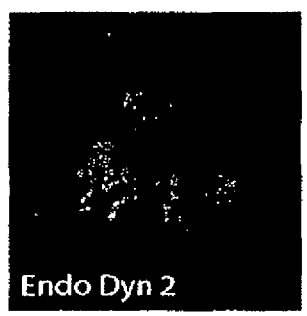
Figure 5D:
Figure 5E:
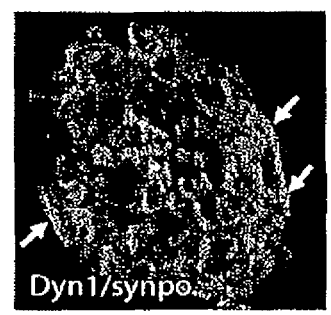
Figure 5F:
Figure 5G:
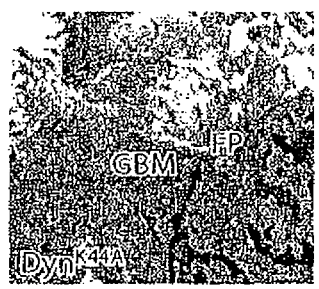
Figure 5H:
Figure 5I:
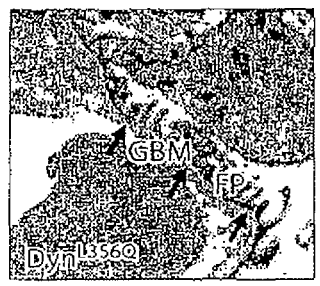
Figure 5J:
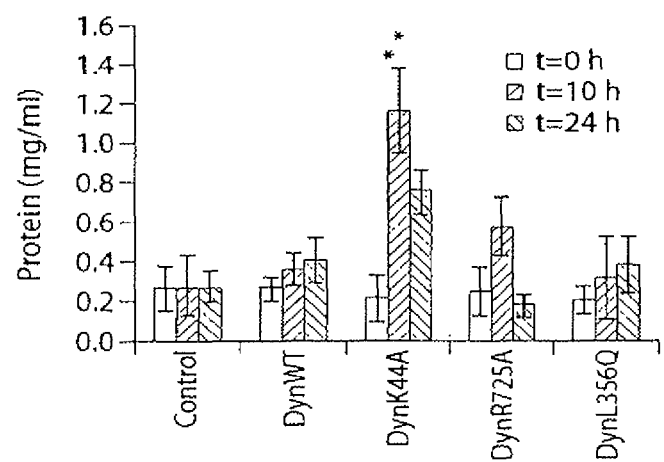

(FIG. 5C). The gene transfer of dynamin 1 expression vectors led to a strong expression of dynamin 1 in glomerular cells including podocytes (FIG. 5D). Some of this labeling was also detected in podocytes, which are marked positively by synaptopodin staining, resulting in a yellow staining pattern (FIG. 5E). The delivery of dynWT did not result in changes of podocyte FP architecture (FIG. 5F). However, gene delivery of the dynK44A, which induced loss of stress fibers in cultured podocytes, induced a severe rearrangement of the actin based podocyte FPs (FIG. 5G). The gene delivery of the dynR725A into wildtype mice resulted in partial FP effacement consistent with the hyperactive function of dynR725A on podocyte stress fiber formation (FIG. 5H). The transfer of the cathepsin L cleavage resistant mutant dynL356Q, G358V did not show any significant changes in podocyte FP structure (FIG. 5I). From these results it was concluded that the level of dynamin:GTP and thus dynamin activity has to be well balanced in order to maintain podocyte FP architecture.

Next, the level of urinary protein loss following gene delivery of dynamin mutants was examined (Table 2). Expression of dynWT in kidney did not lead to increase of the protein in urine (proteinuria). The expression of K44A was associated with severe proteinuria (1.18 mg/ml) at peak gene expression time of 10 hours post injection. The reduction in gene expression was paralleled by a reduction in proteinuria (0.77 mg/ml). Gene transfer of dynR725A caused an increase in proteinuria (0.58 mg/ml). Although this was not a significant increase, it is probable that it is a consequence of the partial podocyte FP effacement seen after gene transfer of dynR725A, and due to increase in the stress fibers formation observed in cultured podocytes. The expression of dynL356Q, G358V did not result in proteinuria (FIG. 5I).

Dynamin R725A and the Novel Cathepsin L Resistant Dynamin Mutant L356Q, G358V can Rescue Podocyte Foot Process Effacement and Proteinuria.

Figure 6A:
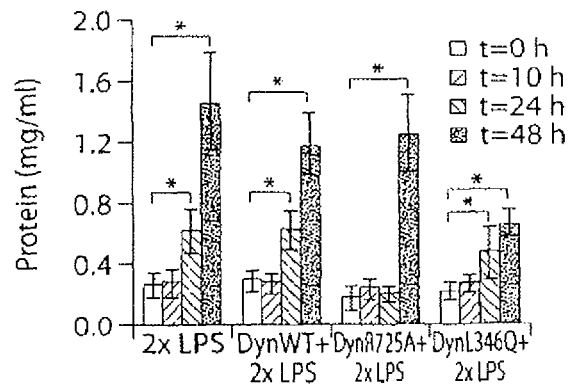
FIG. 6 is a panel of bar graphs (A, C) and a panel of immunostaining images (B, D) showing that R725A (SEQ ID NO. 4) and L356Q, G358V (SEQ ID NO. 3) can protect and remodel podocyte foot processes and influence directly the course of proteinuria. A) Ability of R725A (SEQ ID NO. 4) and L356Q, G358V (SEQ ID NO. 3) to prevent the development of proteinuria. Of note is the time point at 24 hours when there is a peak effect of LPS and strong expression of dynamin mutants. R725A (SEQ ID NO. 4) and L356Q, G358V (SEQ ID NO. 3) confines strong protection at this time points. B) The injection of LPS alone causes severe podocyte foot process effacement. R725A (SEQ ID NO. 4) protects from the development of LPS induced podocyte foot process effacement. Dynamin L356Q, G358V (SEQ ID NO. 3) can also inhibit podocyte foot process effacement. C) Ability of R725A (SEQ ID NO. 4) and L356Q, G358V (SEQ ID NO. 3) to reverse the development of proteinuria. R725A (SEQ ID NO. 4) and L356Q, G358V (SEQ ID NO. 3) expression in proteinuric mice led to a powerful reversal of proteinuria within 10 hours after gene injection. D) R725A (SEQ ID NO. 4) and L356Q, G358V (SEQ ID NO. 3) lead to accelerated remodeling of podocyte foot processes. Whereas wild type dynamin is degrading in LPS injected mice, the expression of the cathepsin L cleavage dynamin mutant L356Q, G358V (SEQ ID NO. 3) is well preserved.
Figure 6B:
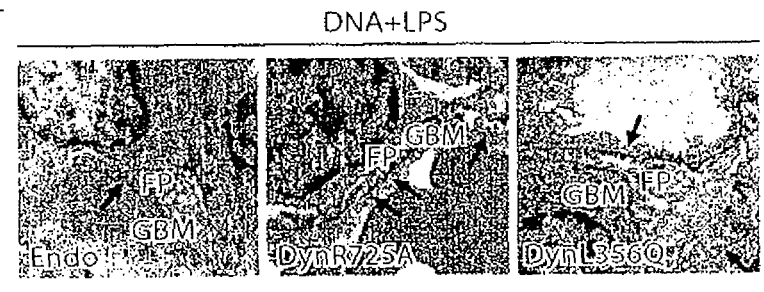
Figure 6C:
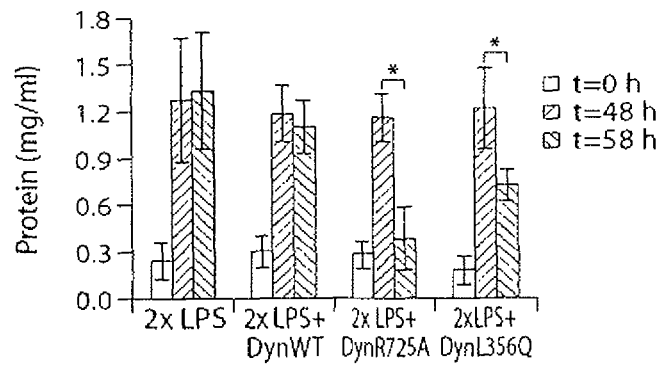

Next, it was examined whether gene transfer of dynR725A and dynL356Q, G358V was able to protect from LPS induced changes of podocyte FP and thus proteinuria (FIGS. 6A-B); (Table 2B). The injection of LPS led to a gradual increase in proteinuria (0.60 mg/ml after 24 hours, 1.46 mg/ml after 48 hours); table 2B and severe FP effacement (FIG. 6A). Whereas the application of wildtype dynamin was unable to protect from LPS induced podocyte FP effacement (data not shown) and proteinuria (0.63 mg/ml after 24 hours, p<0.05 and 1.18 mg/ml after 48 hours, p<0.04); table 2B, the co-administration of R725A together with LPS completely abolished the development of proteinuria after 24 hours (0.20 mg/ml). Podocyte FPs remained normal at this timepoint (FIG. 6B). The decline of R725A expression in podocytes was then associated with the development of proteinuria (1.25 mg/ml, 48 h). At this time point, there was noticeable podocyte FP effacement. The application of the cathepsin L resistant dynamin mutant L356Q, G358V together with LPS conferred a partial protection from proteinuria (0.47 mg/ml, P<0.05). This protection was associated with normal appearing podocyte FP (FIG. 6C). Although this protection was not as strong as the one provided by dynR725A, it was prolonged and was still present even after the second dose of LPS (0.65 mg/dl, P<0.04). This observation argues that lower expression levels of dynL356Q, G358V are required to protect from LPS induced FP effacement but the presence of dynR725A has the most powerful protection.

Figure 6D:
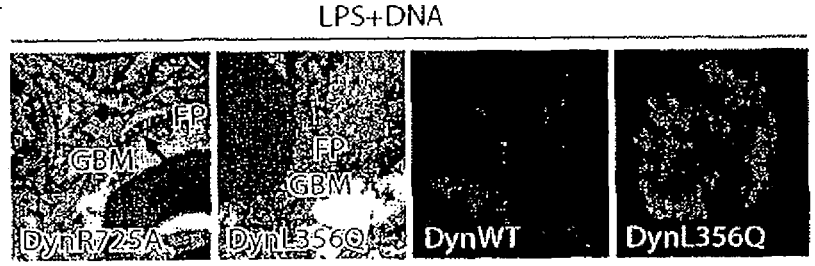
Figure 7:
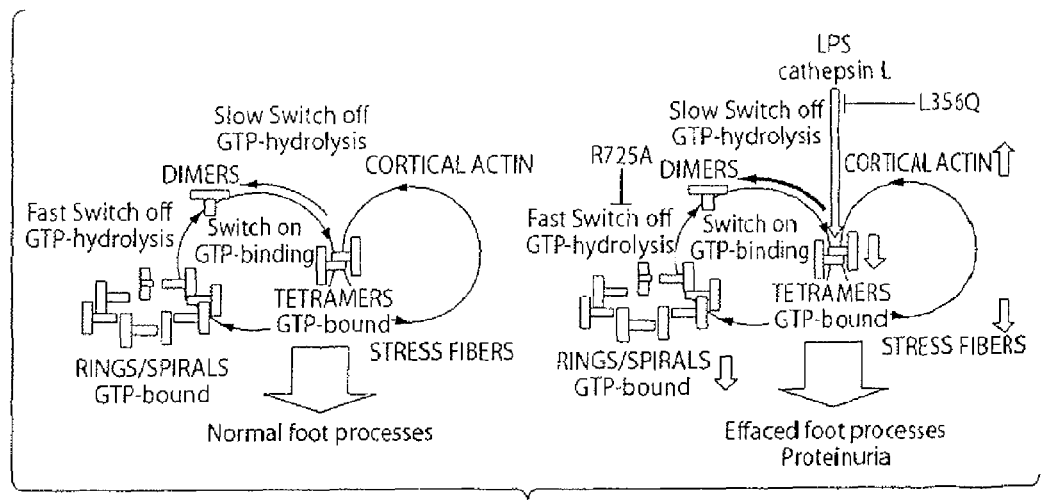
FIG. 7 is a panel of schemes illustrating the role of dynamin in the formation of actin-cytoskeleton in healthy and diseased podocytes.

Another set of experiments was carried out to study whether dynR725A and dynL356Q, G358V are also useful once there is already established podocyte damage and proteinuria (reversal experiments), (FIGS. 6C, D); (Table 2C). First LPS was injected in mice at 0 and 24 hours and the course of urinary protein loss was documented. On the peak phase of proteinuria at 48 hours after the first LPS injection, either delivery solution (control), dynR725A or dynL356Q, G358V dynamin mutants were transferred and the morphology of podocyte FP was analyzed and the degree of proteinuria was determined 10 hours later when there was strong expression of the transferred gene in podocytes. The gene transfer of wildtype dynamin was unable to reshape podocyte FPs and thus proteinuria remained high (1.26 mg/ml to 1.32 mg/ml). However, the gene transfer of dynR725A led to a strong reduction of proteinuria (1.15 mg/ml to 0.38 mg ml within 10 hours). A dramatic reformation of podocyte FPs was also observed (FIG. 6C). The same observation was true for L356Q, G358V (FIG. 6D) which was able to reduce proteinuria from 1.20 mg/ml to 0.71 mg/ml). From the in vitro data it was determined that R725A starts to self assemble into higher order structures in the LPS setting which render dynamin assembly domain protected from cathepsin L cleavage. The protection of dynamin L356Q, G358V mutant in a setting where there is induction of podocyte cathepsin L was obvious when compared to transferred wildtype dynamin which was unable to reduce FP effacement and which expression was rapidly decreased (FIG. 6, panel dynWt) whereas at the same timepoint dynL356Q, G358V was strongly present (FIG. 6, panel dynL356Q, G358V). These results suggest that the resistance of dynamin to cathepsin L cleavage can protect and reverse LPS induced podocyte damage by allowing dynamin to protect its assembly domain and form quaternary structures to hydrolyse GTP and keep the actin cytoskeleton organized (FIG. 7). In addition, dominant activating dynR725A proves useful because despite causing podocyte damage in wildtype mice, it can resist cathepsin L cleavage by self assembly in the LPS setting and have strong activity by impairment in its GTP hydrolysis.

TABLE 1

| Donor | Acceptor | Variant | Mean Lifetime (γ1) | Mean Lifetime p (compared to WT) |
|---|---|---|---|---|
| *GTPase-Alexa488 | none | | 2465 ± 70− | p < 0.05 |
| *GTPase-Alexa488 | DAM-Alexa568 | +control | 1025 ± 71+ | p < 0.05 |
| *GTPase-Alexa488 | GAR-Alexa568 | −control | 2417 ± 69− | p < 0.05 |
| *GTPase-Alexa488 | Hudy1-Alexa568 | WT | 2212 ± 65+ | |
| *GTPase-Alexa488 | Hudy1-Alexa568 | K694A | 2408 ± 40− | p < 0.05 |
| GTPase-Alexa488 | Hudy1-Alexa568 | R725A | 2408 ± 128− | p < 0.05 |
| GTPase-Alexa488 | Hudy1-Alexa568 | WT + LPS | 2558 ± 45− | p < 0.05 |
| GTPase-Alexa488 | Hudy1-Alexa568 | WT + LPS + E64 | 2277 ± 108+ | p < .05 |
| GTPase-Alexa488 | Hudy1-Alexa568 | R725A + LPS | 2267 ± 95+ | p < .05 |
| GTPase-Alexa488 | Hudy1-Alexa568 | R725A + LPS + E64 | 2414 ± 58− | p < 0.05 |

TABLE 2

A

| Protection | Protein in the urine (mg/ml) | | |
|---|---|---|---|
| Experiments | t = 0 | t = 10 h | t = 24 h |
| Control | 0.28 ± 0.11 | 0.28 ± 0.14 | 0.28 ± 0.08 |
| Dyn WT | 0.27 ± 0.06 | 0.37 ± 0.08 | 0.42 ± 0.12 |
| Dyn K44A | 0.23 ± 0.11 | 1.18 ± 0.22* | 0.77 ± 0.11* |
| Dyn R725A | 0.26 ± 0.13 | 0.58 ± 0.17 | 0.20 ± 0.05 |
| Dyn L356Q, G358V | 0.22 ± 0.06 | 0.33 ± 0.21 | 0.40 ± 0.15 |

B

| Prevention | Protein in the urine (mg/ml) | | | |
|---|---|---|---|---|
| Experiments | t = 0 | t = 10 h | t = 24 h | t = 48 h |
| 2 × LPS | 0.26 ± 0.09 | 0.27 ± 0.09 | 0.60 ± 0.14* | 1.46 ± 0.33* |
| Dyn WT + 2 × LPS | 0.28 ± 0.07 | 0.27 ± 0.07 | 0.63 ± 0.12* | 1.18 ± 0.23* |
| Dyn R725A + 2 × LPS | 0.17 ± 0.07 | 0.23 ± 0.07 | 0.20 ± 0.05 | 1.25 ± 0.26* |
| Dyn L356Q, G358V + 2 × LPS | 0.21 ± 0.05 | 0.26 ± 0.05 | 0.47 ± 0.17* | 0.65 ± 0.10* |

C

| Reversal | Protein in the urine (mg/ml) | | |
|---|---|---|---|
| Experiments | t = 0 | t = 48 h | t = 58 h |
| 2 × LPS | 0.24 ± 0.11 | 1.26 ± 0.39 | 1.32 ± 0.37 |
| 2 × LPS + Dyn WT | 0.30 ± 0.10 | 1.17 ± 0.18 | 1.10 ± 0.17 |
| 2 × LPS + Dyn R725A | 0.28 ± 0.08 | 1.15 ± 0.15 | 0.38 ± 0.20* |
| 2 × LPS + Dyn L356Q, G358V | 0.18 ± 0.08 | 1.20 ± 0.27 | 0.71 ± 0.09* |

Example 2

Dynamin Self-Assembly into Higher Order Structures in Live Cells Occurs in the Cytoplasm and is Regulated by Actin Dynamics Identification of Dynamin Self-Assembly into Higher Order Structures by FLIM.

FLIM is based on the fluorescence resonance energy transfer (FRET) between the donor and acceptor that shortens the lifetime of the donor if the acceptor distance is within ≈100 Å (10 nm). Therefore, the detection of shortened lifetimes demonstrates FRET and indicates spatial proximity of the two labeled molecules. To this end, dynamin was tagged with either ECFP or EYFP on its N- and C-termini. Fusion proteins were expressed in COS cells, because these cells are flattened and have minimal background autofluorescence, which allows clear visualization of cells by wide-field microscopy. Cells containing all combinations of tagged dynamin, supported endocytosis, demonstrating that the fusion proteins did not act as dominant negatives. Tagging protein did not alter its subcellular localization (FIG. 8B), demonstrating that majority of overexpressed protein stays in the cytosol, as shown for the overexpressed non-tagged dynamin. Moreover, cells expressing dominant negative dynamins, ECFP-dynK44A or ECFP-dynI690K exhibited potent decrease in the amount of internalized rhodamine-Transferrin (RTfn), whereas cells expressing dominant activator ECFP-dynK694A exhibited increase in the amount of internalized RTfn. Together, these data demonstrate that tagged proteins are functional and are in agreement with functional dynamin tagged by EGFP.

Figure 8A:
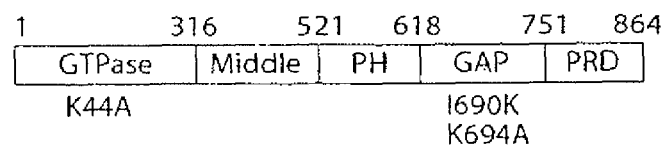
FIG. 8 is a scheme of the dynamin gene (A), showing the various domains of the peptide, a panel (B) of gel-shift assays of dynamin mutants, and a scheme (C), depicting higher order dynamin structures.
Figure 8B:
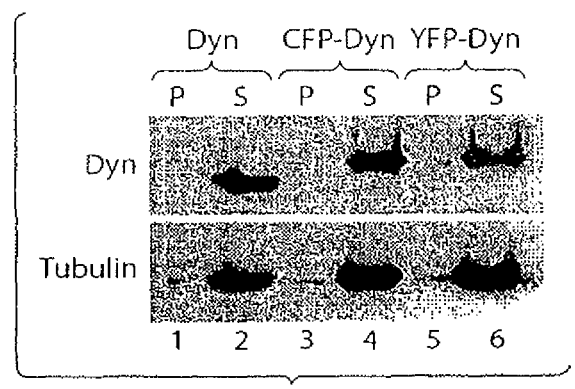
Figure 8C:
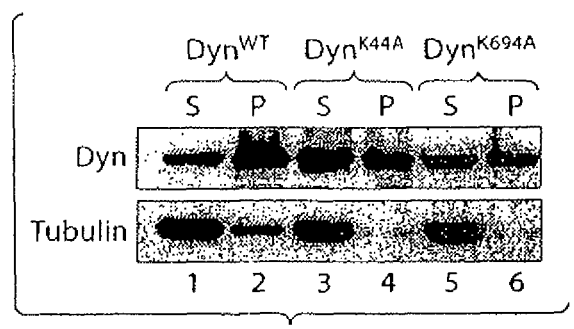
Figure 8D:
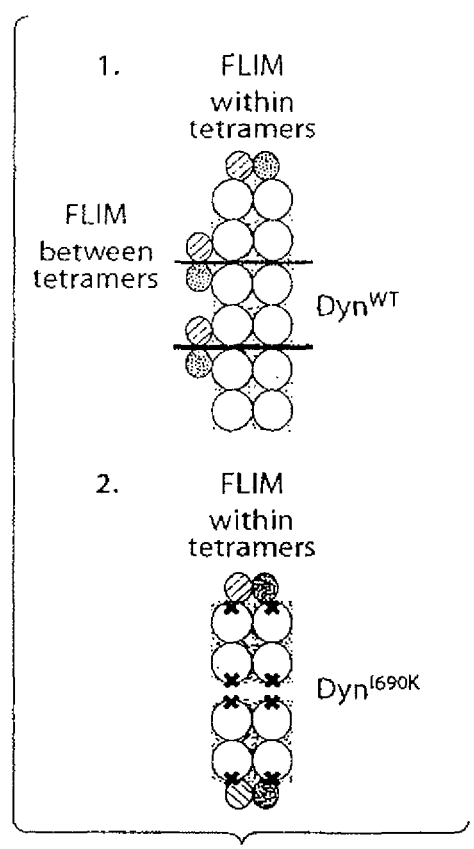
Figure 9A:
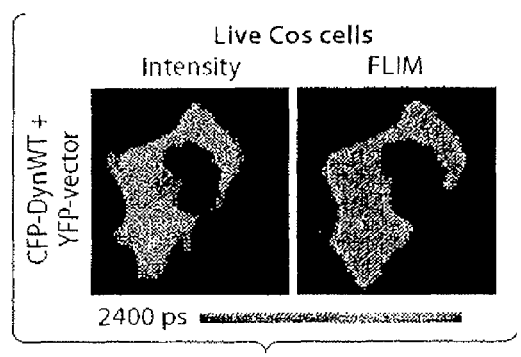
FIG. 9 is a panel of immunostaining images depicting dynamin-dynamin interactions in live COS cells (A-D) and podocytes (E-H), a bar graph (J) depicting the quantification of the dynamin-dynamin interactions.
Figure 9B:
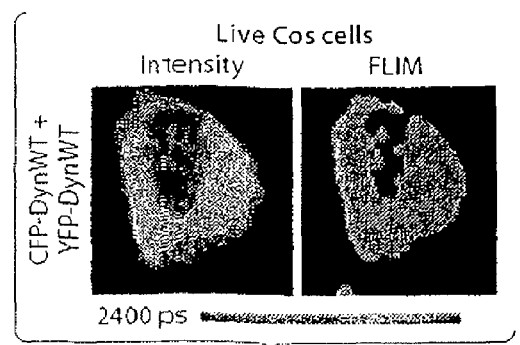
Figure 9C:
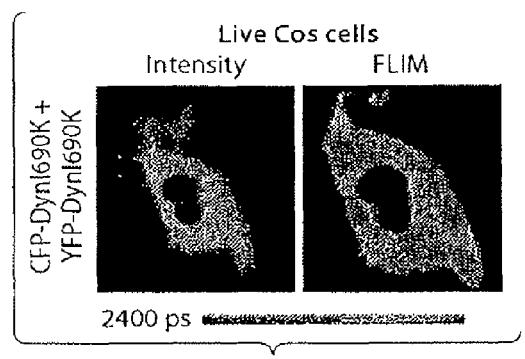
Figure 9D:
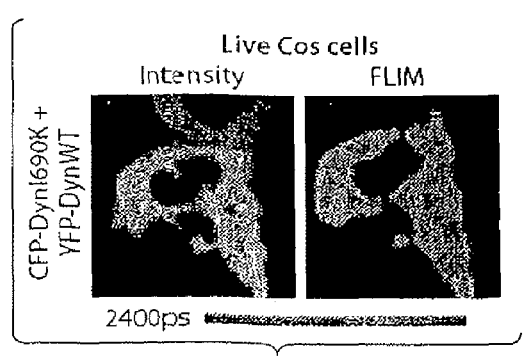

As shown in FIG. 9C, co-expression of ECFP-dynamin (donor) and YFP-dynamin (acceptor) in the same cell resulted in FRET, measured as a decrease in the fluorescence lifetime of ECFP, which is indicated by the orange color. The decrease in lifetime was comparable to a positive control in which ECFP and EYFP are present on the same polypeptide (Table II-1). Negative controls show that FRET only occurred when ECFP and EYFP were each fused to dynamin (FIG. 9A and Table 3). The observed decrease in fluorescence lifetime of CFP-dynamin in cells expressing EYFP-dynamin could result from interactions between dynamin monomers within tetramers/dimers, or from interactions between assembled tetramers/dimmers into higher order structures (FIG. 8C). To distinguish these two possibilities, we used FLIM to examine dynI690K. DynI690K is expected to form tetramers as efficiently as the wild type protein, but it exhibits defective higher order assembly of tetramers in vitro (FIG. 8C model 2). Strikingly, when ECFP-dynI690K and EYFP-dynI690K were co-expressed, the fluorescence lifetime of ECFP was significantly slower than when it was fused to wild type dynamin (FIG. 9C and Table 3). The longer average lifetimes of dynI690K than dynwt argue strongly that the assay detects higher order dynamin self-assembly and not tetramer formation. Moreover, when ECFPdynI690K was co-expressed with EYFP-dynWT, the fluorescence lifetime of ECFP was significantly faster (FIG. 9D). These data demonstrate that I690K phenotype is due to decrease in affinity for self-association, and that this decrease can be partially overcome by the presence of the wildtype enzyme.

In agreement with this interpretation, fluorescence lifetime of ECFP in cells coexpressing ECFP-dynK694A and EYFP-dynK694A, another dynamin mutant impaired in oligomerization, also exhibited slower lifetimes. The fact that this significant decrease in the fluorescence lifetime of ECFP is statistically insignificant is due to high fluctuations of the lifetimes between different cells (high error bar in Table 3). This is most likely due to ability of dynK694A to overcome its assembly defect under certain circumstances as shown in vitro. The fact that ECFP-dynK694A has a faster lifetime than ECFP-dynI690K is in agreement with its less severe assembly defect measured in vitro (apparent affinity of dynK694A is ~7-fold lower then dynWT, whereas it is unmeasurable for dynI690K). Together these data demonstrate that FLIM detected dynamin oligomerization into higher order structures and not dimerization/tetramerization.

To determine whether observed FRET is the result of endocytosis at the plasma membrane, endocytosis was inhibited by treating cells with b-methyl-cyclodextrin (MBCD). This reagent extracts cholesterol from the membrane and is known to cause accumulation of shallow coated pits. Since dynamin self-assembly at the plasma membrane is predicted to occur only during and/or after formation of constricted coated pits, treatment of the cells with MBCD is expected to abolish endocytosis-dependent FRET signals. In contrast to this prediction, dynamin-dynamin higher order interactions occurred unchanged even in the absence of endocytosis (Table 3). Since overexpressed protein is predominantly present in the cytosol, these data suggest that observed FRET was due to dynamin oligomerization in the cytosol and not at the membranes. This interpretation is also in agreement with cytoplasmic distribution of the signal through the cell. Dynamin oligomerization in the cytosol may be due to high levels of overexpression and thus not present properties of endogenous protein. Alternatively, high levels of protein might have enabled detection of interactions that normally do occur in the cytosol. Given that endogenous dynamin is distributed equally between cytosolic and membrane associated fractions, and that FLIM can detect highly transient interactions otherwise missed by electron microscopy, we next attempted to determine what promoted this dynamin oligomerization in the cytosol.

Dynamin Self-Assembles into Higher Order Structures at the Plasma Membrane and in the Cytoplasm in a Nucleotide-Dependent Manner.

Next it was examined whether dynamin self-assembly in vivo in the cytosol requires GTP binding. Current data give mixed messages on this subject. Dynamin can fully assemble onto lipids in the absence of nucleotide. In contrast, dynamin collars have been observed on membranes only in the presence of GTPgS, and dynamin self-assembly in solution also requires GDP:AlF4 or GTPγS suggesting that at least in some instances dynamin-dynamin interactions are GTP-promoted. Using the FLIM assay, it was examined whether the GTPase mutant, dynK44A, which cannot bind GTP or support endocytosis is able to self-assemble in vivo. As shown in Table 3, fluorescence lifetime of ECFP-dynK44A is as slow as in the control cells lacking EYFP-tagged dynamin. These data demonstrate that in live cells dynamin needs to bind GTP in order to engage in dynamin:dynamin interactions in the cytosol, and are in agreement with GTP-dependent dynamin assembly in solution. DynK44A is shown to be a tetramer, further demonstrating that short fluorescence life time measure for the ECFP-dynWT is indeed due to dynamin oligomerization into higher order structures and not formation of tetramers. Dynamin has been isolated as microtuble (MT) binding protein, and MT potently increase its GTPase activity suggesting that dynamin can use MT as a template for self-assembly. In order to examine whether observed self-assembly in cytosol was promoted by MT, Cos cells were pretreated with nocodazole, a reagent that depolymerizes microtubules. As shown in Table 3, MT depolymerization had no effect on dynamin oligomerization.

Given dynamin's role in actin dynamics, we next examined whether changes in cytoskeletal dynamics are critical for dynamin self-assembly. To this end, COS cells were pretreated with either actin depolymerizing agents, cytochalasin D (cyto D), or actin stabilization reagent jasplakinolide. As shown in Table 3, addition of the cyto D, significantly promoted dynamin-dynamin interactions measured by FLIM, whereas addition of jasplakinolide had no effect. Together, these data suggested that short actin filaments and/or mornomeric actin generated by cyto D were promoting dynamin self-assembly in the cytosol.

Figure 9E:
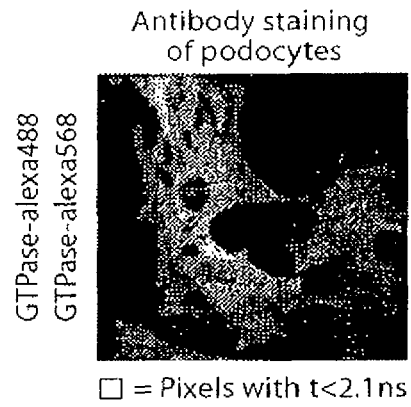
Figure 9F:
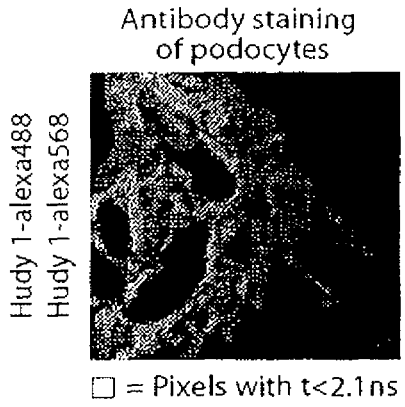
Figure 9G:
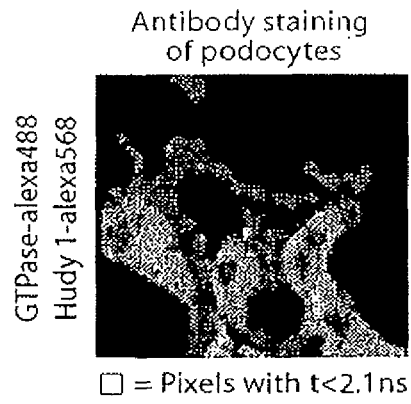
Figure 9H:
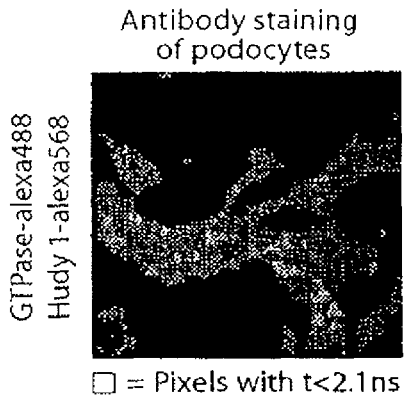
Figure 9J:
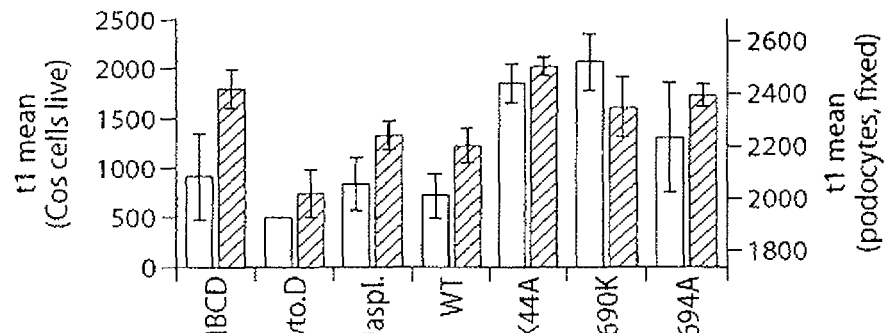

To further test this hypothesis, next dynamin self-assembly was examined in highly specialized kidney cells, podocytes. Podocytes are terminally differentiated cells that support the ultrafiltration of blood. Membrane remodeling of podocytes is essential for their function and it is driven by reorganization of actin filaments. Since podocytes are terminally differentiated and thus are not efficiently transfected, in order to perform FLIM experiments in podocytes, different dynamin mutants were overexpressed using adenoviral expression system, which enables greater than 90% infection efficiency. Cells were fixed and FLIM was performed using mixture of monoclonal anti-dynamin antibodies prior conjugated to either Alexa-488 (donor florophore) or Alexa-568 (acceptor florophore). In this experimental approach, lifetime of alexa-488 should be shortened if alexa-568 is in close proximity. As expected, overexpression of dynK44A or dynI690K potently inhibited endoctyosis of RTfn, whereas overexpression of dynK694A increased amount of internalized RTfn when compared to cell expressing dynWT. In contrast to COS cells, overexpressed dynamin was equally distributed between particular and cytosolic fractions (FIG. 8C), which is identical to distribution of endogenous dynamin (see asterisks in FIG. 8B). For FLIM experiments two different monoclonal anti-dynamin antibodies were used: the GTPase antibodies (Stressgene) that recognize epitope on the very N-terminal region of dynamin, and Hudy-1 (Sigma), antibodies that recognizes epitope within PRD-domain situated at the very C-terminal region of dynamin (FIG. 8A). Both antibodies were conjugated with either Alexa-488 or Alexa-568 and cells were stained by mixing both florophores and examining lifetime of Alexa-488 (a488). All combination of antibodies were examined for the occurrence of FRET. As shown in FIG. 9E, when cells were stained using antibodies against N-terminal GTPase domain, no FRET signal was detected (Table 4). In contrast, labeling cells with Hudy1, resulted in statistically significant decrease in the fluorescence lifetime of Alexa-488 (FIG. 9F and Table 4). The decrease in lifetime was also detected if cells were stained using combination of two antibodies, GTPase-Alexa488 and Hudy1-Alexa568, and this pair was used in all subsequent experiments (FIG. 9G and Table 4). As expected, assembly incompetent mutant, auxI690K exhibited the same level of FRET detected by FLIM as observed for the control cells (Table 4), further demonstrating that FLIM was detecting dynamin self-assembly into higher-order structures. Importantly, FRET only occurred at the region of cell-cells junctions, region that supports active actin rearrangement (Table 4). Thus, it was next examined whether, as in the case of Cos cells, disruption of actin cytoskeleton by cytocholasin D can promote dynamin self-assembly in the cytosol. This was indeed the case as shown in FIG. 9H and Table 4. In cells pretreated with cyto D, decrease in the lifetime of alexa 488 is detected through the cytoplasm, demonstrating that short actin filaments and/or monomeric actin can in deed promote dynamin self-assembly. In contrast, pretreatment of podocytes with jasplakinolide did not effect dynamin self-assembly at the membrane. Together these data demonstrate for the first time that dynamin can self assembles in the cytoplasm, and that this assembly is promoted by short actin filaments.

Role of Dynamin Self-Assembly for Actin Dynamics.

There was no detection of FRET by FLIM in cells expressing auxK694A (Table 4), demonstrating that this protein was not self-assembling. This data are in agreement with the biochemical properties of this mutant. Furthermore, as shown in Table 4, there was no detection of FRET by FLIM in cells expressing dynK44A.

TABLE 3

FLIM analysis for proximity between dynamin-dynamin interactions in live COS cells

| Donor | Acceptor | Treatment | Mean Lifetime (γ1) ps | Mean Lifetime p (compared to WT) |
|---|---|---|---|---|
| CFP-WT | | | 2425 ± 76 | $p < 0.001$ |
| CFP-I690K | | | 2292 ± 297 | $p < 0.001$ |
| CFP-WT | YFP | | 1841 ± 437 | $p < 0.001$ |
| CFP-I690K | YFP | | 1838 ± 309 | $p < 0.001$ |
| CFP-WT | YFP-WT | | 716 ± 224 | |
| CFP-K44A | YFP-K44A | | 1858 ± 187 | $p < 0.001$ |
| CFP-I690K | YFP-I690K | | 2068 ± 283 | $p < 0.001$ |
| CFP-I690K | YFP-WT | | 1113 ± 132 | $p < 0.50$ |
| CFP-K694A | YFP-K694A | | 1299 ± 557 | $p < 0.50$ |
| CFP-WT | YFP-WT | MBCD | 916 ± 427 | $p < 0.50$ |
| CFP-WT | YFP-WT | Cyto. D | 510 ± 29 | $p < 0.05$ |
| CFP-WT | YFP-WT | Jaspl. | 845 ± 263 | $p < 0.50$ |

TABLE 4

FLIM analysis for proximity between dynamin-dynamin interactions in podocytes

| Donor | Acceptor | Variant/TX | Mean Lifetime ($\gamma 1$) | Mean Lifetime p (compared to WT) |
|---|---|---|---|---|
| GTPase-a488 | none | | 2465 ± 70 | $p < 0.05$ |
| GTPase-a488 | DAM-a568 | +control | 1025 ± 71 | $p < 0.05$ |
| GTPase-a488 | DAM-a568 | −control | 2339 ± 71 | $p < 0.05$ |
| GTPase-a488 | GTPase-a568 | WT | 2423 ± 46 | $p < 0.5$ |
| GTPase-a488 | Hudy1-a568 | WT | 2254 ± 60 | |
| GTPase-a488 | Hudy1-a568 | K44A | 2515 ± 43 | $p < 0.001$ |
| GTPase-a488 | Hudy1-a568 | 1690K | 2359 ± 120 | $p < 0.05$ |
| GTPase-a488 | Hudy1-a568 | K694A | 2408 ± 40 | $p < 0.05$ |
| GTPase-a488 | Hudy1-a568 | Colchisine | 2295 ± 98 | $p < 0.5$ |
| GTPase-a488 | Hudy1-a568 | Jaspl. | 2254 ± 58 | $p < 0.5$ |
| GTPase-a488 | Hudy1-a568 | WT + Cyto. D | 2031 ± 94 | $p < 0.001$ |
| GTPase-a488 | Hudy1-a568 | K44A + Cyto. D | 2311 ± 87 | $p < 0.05$ |
| GTPase-a488 | Hudy1-a568 | 1690K + Cyto. D | 2431 ± 94 | $p < 0.001$ |
| GTPase-a488 | Hudy1-a568 | K694A + Cyto. D | 2051 ± 94 | $p < 0.001$ |

Figure 10A:
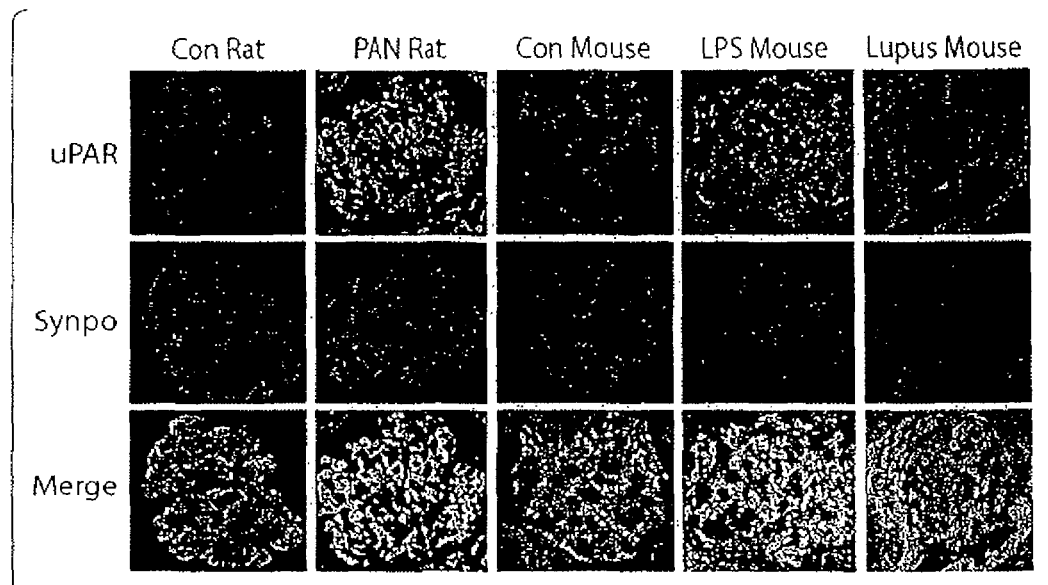
FIG. 10 is a panel of immunostaining images (A,C), bar graphs (B,D), and a gel shift (D) showing the induction of uPAR in podocytes in vivo and in vitro.
A) Confocal microscopy shows low level of uPAR expression (green) in glomeruli of normal rat or mouse. It partially co-localized with a podocyte marker, synaptopodin, resulting in a minimal yellow overlap. uPAR was apparently increased in podocytes in rat PAN nephrosis, mouse LPS transient nephrotic syndrome and lupus nephritis, resulting in an enhanced yellow overlap. B) Taqman Real-time PCR shows that glomerular uPAR mRNA was upregulated in human FSGS and diabetic nephropathy. Values were presented as Mean± SEM. * $p<0.05$ for FSGS or DN versus control patients. C) Expression of uPAR in cultured mouse podocytes. uPAR expression, which was minimally observed in untreated podocytes in the cytoplasm, was significantly increased by LPS or PAN treatment. Of note is that uPAR was enriched in leading edge (arrow). D) Western blotting confirmed the result of immunostaining, showing that uPAR was significantly induced by LPS or PAN, Values were standardized against a tubulin. * $p<0.05$ for LPS or PAN treated podocytes versus controls. Synpo, synaptopodin; cont, controls.

Example 3 uPAR-Guided Spatial Motility of Kidney Podocytes is Essential for the Development of Urinary Protein Loss The urokinase plasminogen activator receptor (uPAR) is a glycosylphophatidylinositol (GPI)-anchored protein. uPAR and its ligand vitronection are involved in the directional invasion of migrating cells, but uPAR has also been recognized as a proteinase receptor that elicits a plethora of cellular response including cellular adhesion, proliferation and migration in a non-proteolytic fashion. Mechanisms by which uPAR exercises these functions involve its ability to complex with other membrane proteins such as integrins for signal transduction. It has been recently shown that cultured podocytes display an increased migratory response when remodeling their cellular structure under experimental proteinuric conditions. To explore a role of uPAR in podocyte migration during proteinuric kidney diseases, the expression pattern of uPAR was explored in three different animal models of inducible proteinuria, including the rat puromycin aminonucleoside (PAN) nephrosis model, the mouse model of LPS-induced transient nephrotic syndrome and the NZB/W F1 model of murine lupus nephritis. Low expression of uPAR was found in glomeruli from control rats or mice (FIG. 1A). uPAR was partially localized in podocytes as indicated by coimmunofluorescent staining with the podocyte marker synaptopodin. In contrast, podocyte expression of uPAR was significantly increased in all three rodent models of proteinuric kidney diseases, as demonstrated by the yellow staining pattern resulting from the overlap with synaptopodin (FIG. 10A). Whereas the glomerular expression of uPAR in the PAN and LPS model was increased uniformly in podocytes (FIG. 10A), uPAR was mainly found in podocytes populating cellular crescents in lupus nephritis (FIG. 10A). In addition to glomerular uPAR labeling, uPAR expression was also found in kidney tubules as described before. Since vitronectin is important for uPAR mediated cell motility, the expression of glomerular vitronectin in these rodent models was also analyzed. Similar to uPAR, vitronectin had a low level of expression in normal podocytes, but was significantly upregulated in PAN-treated nephrotic rats, LPS-treated mice and lupus mice.

Figure 10B:
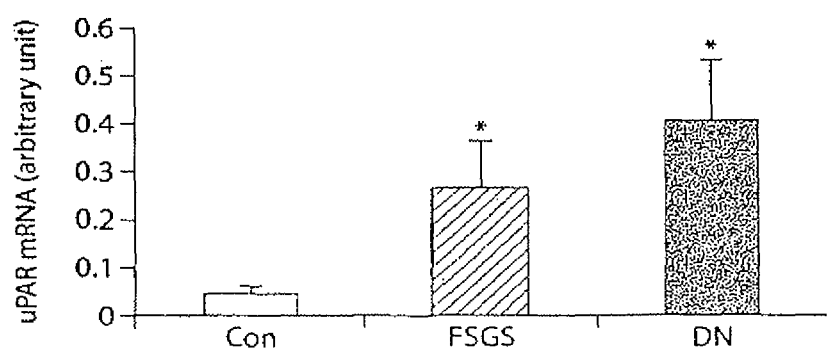

Next, quantitative RT-PCR was performed of uPAR mRNA expression using isolated glomeruli from human biopsies. The uPAR expression was analyzed in patients without glomerular disease and in patients with focal segmental glomerulosclerosis (FSGS) and diabetic nephropathy, both conditions known to display podocyte foot process effacement and proteinuria. Patients without glomerular diseases had a low level of glomerular uPAR mRNA expression FIG. 10B). However, patients with biopsy-proven FSGS had a significant increase in glomerular uPAR expression (p<0.05 versus patients without glomerular disease) (FIG. 10B). Patients with diabetic nephropathy had an even stronger induction of glomerular uPAR expression (p=0.012, versus patients without glomerular disease) (FIG. 10B).

Figure 10C:
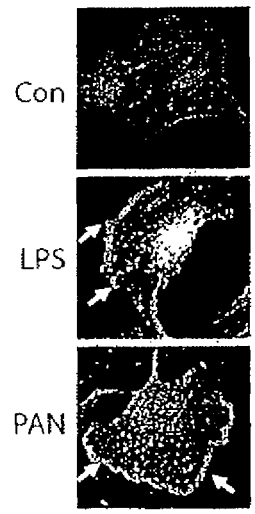
Figure 10D:
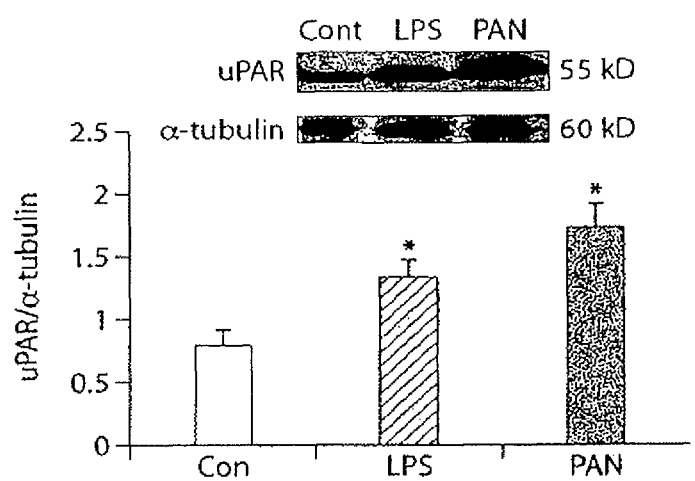

To study the function of uPAR in more detail, a mouse podocyte cell line was utilized Immunoflourescent labeling showed low cytoplasmic expression of uPAR in cultured differentiated podocytes (FIG. 10C). However, 24 h after LPS or PAN treatment of podocytes, the expression of uPAR was significantly increased. Of note is the redistribution of uPAR into the cell membrane, particularly at the leading edge (arrow), which is consistent with the induction of a migratory podocyte phenotype. The baseline expression of uPAR and its upregulation by LPS and PAN treatment were confirmed by western blotting (FIG. 10D). Quantitative analysis of uPAR expression in podocytes revealed the strongest induction of uPAR protein after PAN treatment (FIG. 10D).

Figure 11A:
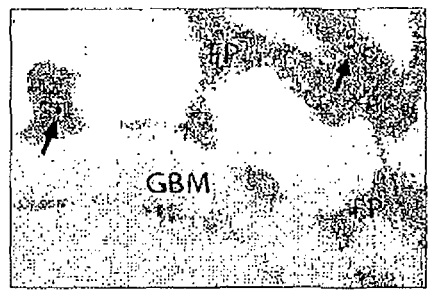
FIG. 11 is a panel of immunostaining images (A,B,D) and gel shifts (C,E) showing the association of uPAR with podocin and lipid rafts. A) Subcellular localization of uPAR Immunoelectron microscopy shows that uPAR was localized in the foot processes close to slit diaphragm. B) Colocalization of uPAR with podocin. uPAR-GFP transfected podocytes were stained with podocin. Confocal microscopy revealed the colocalization of uPAR and podocin, shown as a yellow overlap (arrow). C) uPAR was associated with C-terminus of podocin. D) uPAR was partially colocalized with lipid rafts. Minimal colocalization of uPAR with cholera toxin B, a raft marker, was found in untreated podocytes. After LPS or PAN treatment, the colocalization was enhanced and particularly observed in the focal areas of podocyte membrane. E) Floatation gradient assay. Only minimal level of uPAR was observed in DRM fractions of untreated podoctyes, whereas it was enriched in DRM fractions after PAN treatment. Comparatively, no difference of podocin distribution was observed with or without PAN treatment.
Figure 11B:
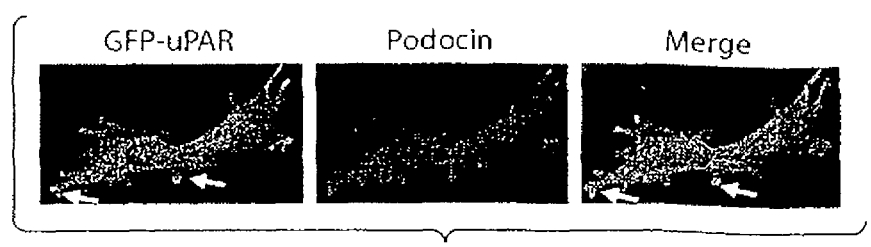
Figure 11C:
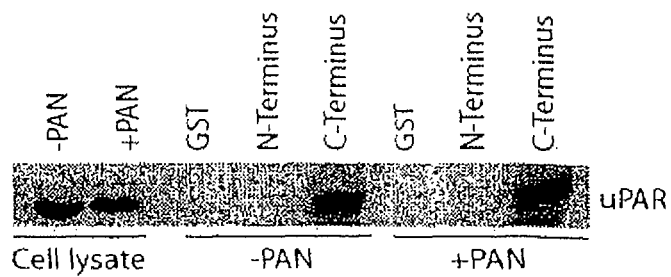

The subcellular localization of uPAR was investigated in ultrathin frozen sections of mouse glomeruli by immuno-electronmicroscopy using antibodies against uPAR. uPAR expression in normal mouse glomeruli was found in podocyte FPs in close vicinity to the SD (FIG. 11A). To analyze uPAR localization with the SD in more detail, a GFP-tagged uPAR construct was overexpressed in normal cultured mouse podocytes and explored its colocalization with the lipid raft associated SD protein podocin. Confocal microscopy examination showed that uPAR partially colocalizes with endogenous podocin in the cell body but also at the cell membrane (FIG. 11B). To study whether uPAR could interact with podocin, we performed GST pull-down assays using the N- and C-terminal fragment of podocin and podocyte lysates respectively. It was found that uPAR specifically associated with the C-terminus of podocin. Since the SD is disrupted under proteinuric conditions, next the association of uPAR with podocin before and after PAN treatment was analyzed (FIG. 2C). Interestingly, the uPAR-podocin interaction was not altered by PAN treatment.

Figure 11D:
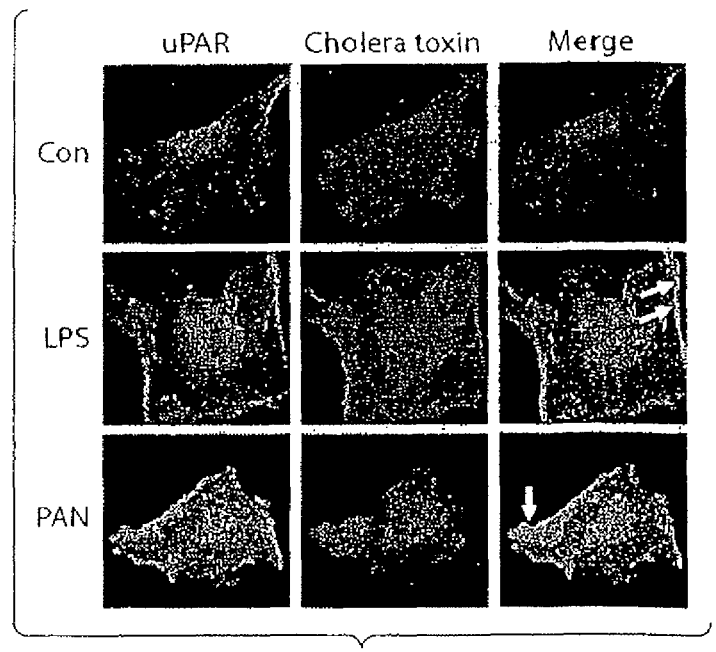
Figure 11E:
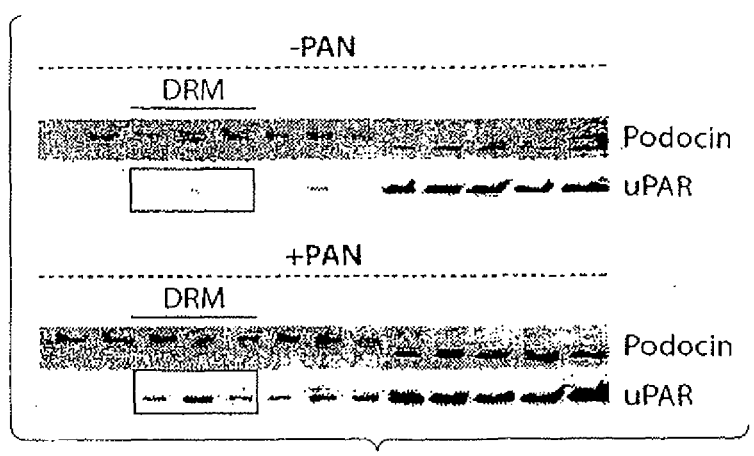

Both podocin and uPAR are known to be associated within detergent resistant membrane fractions (DRM) or lipid raft microdomains. We explored the association of uPAR and podocin with lipid rafts before and after PAN and LPS treatment. In untreated podocytes, there was no obvious colocalization of uPAR with the raft marker cholera toxin B (FIG. 11D). However, LPS and PAN treatment increased uPAR expression in podocytes, leading to a partial colocalization of uPAR and cholera toxin B (FIG. 11D). An association of uPAR in lipid rafts of podocytes was also observed biochemically using flotation gradient assays. In untreated podocytes, podocin was found raft and non-raft associated, whereas uPAR was mainly non-raft associated (FIG. 11E). However, PAN treatment of cultured podocytes led to a shift of uPAR into the detergent resistant membrane fraction whereas the association of podocin with lipid rafts remained unchanged (FIG. 11E).

Figure 12A:
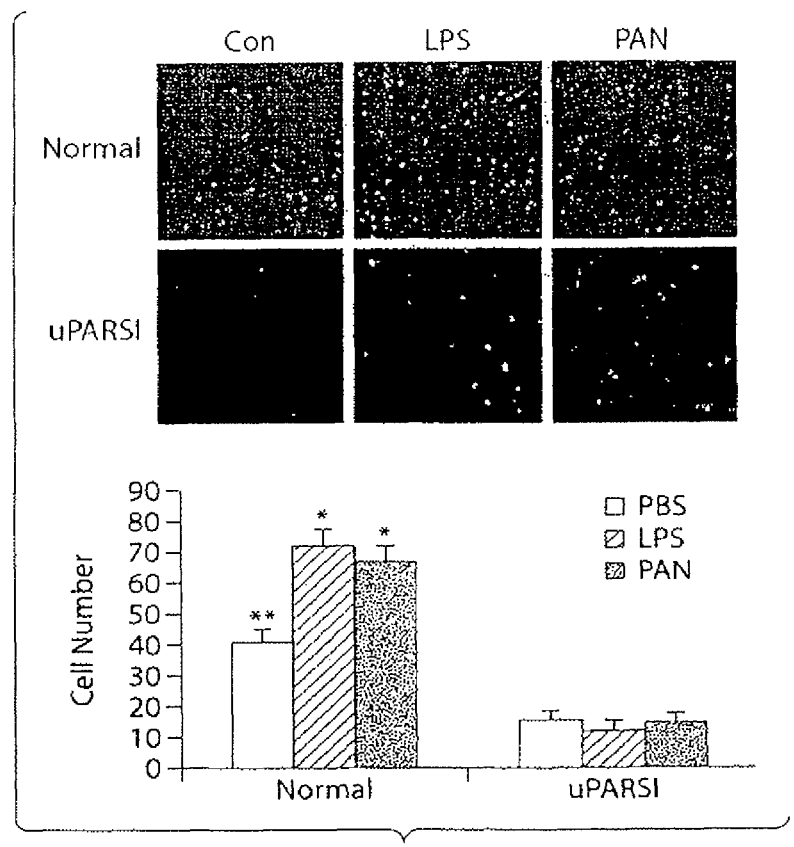
FIG. 12 is as set of immunostaining images and bar graphs (A, C) and gel shifts (B) showing that uPAR mediates podocyte migration. A) Efficiency of uPAR siRNA. The efficiency of uPAR silencing by siRNA in podocytes was proved by RT-PCR as well as Western blotting. B) Multiwell Boyden chamber assay. Podocytes migrated randomly through the membrane were stained with DAPI (blue). As compared to normal control, LPS and PAN pre-treatment for 24 h promoted podocyte migration. Whereas, knock down of uPAR by siRNA inhibited podocyte from migration before and after LPS or PAN treatment. C) Scrape wound assay. LPS or PAN treatment of podocytes for 24 h significantly accelerated wound closure. uPAR siRNA however inhibited podocyte migration and thus wound closure with or without LPS or PAN treatment. uPARSI, uPAR silencing by uPAR siRNA. Solid line shows the initial margin of scrape wound. * $p<0.05$ for LPS or PAN versus PBS treated normal podocytes; ** $p<0.05$ for PBS treated normal podocytes versus uPAR siRNA transfected podocytes.
Figure 12B:
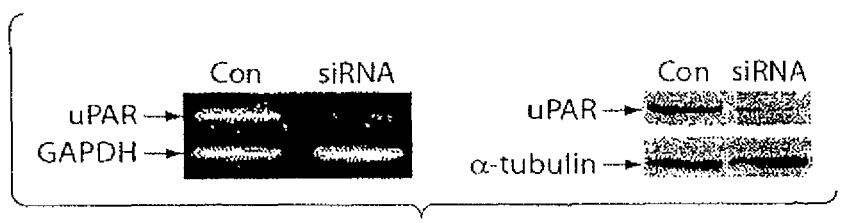
Figure 12C:
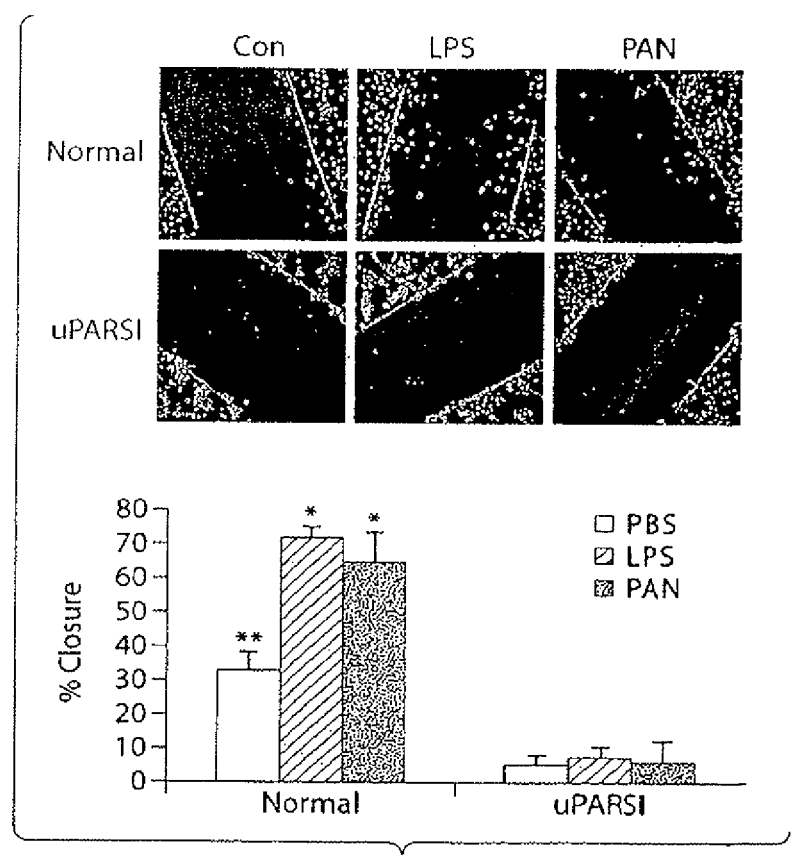

Functionally, lipid raft-associated uPAR has been implicated in cell migration (21). The motility of cultured podocytes was analyzed to explore the consequences of increased uPAR expression in lipid rafts. First, podocyte cell lines were established with stable knock down of uPAR expression using siRNA. The efficiency of uPAR-siRNA was confirmed by both semi-quantitative RT-PCR (>90% inhibition) and Western blotting (>70%) (FIG. 12A). A modified multi-well Boyden chamber assay was used to assess the random migration of differentiated podocytes. LPS- or PAN-treatment for 24 h significantly promoted podocyte migration (FIG. 12B). To test whether this effect was mediated by uPAR, uPAR knock-down studies were performed by stably transfecting uPAR-siRNA into podocytes. Knock down of uPAR significantly decreased the number of migrating podocytes before and after treatment with LPS or PAN (FIG. 12B). These results demonstrate that uPAR is necessary for podocyte cell migration. Since podocyte FP effacement requires the disruption of the SD and the movement of podocyte foot processes on the GBM, it was investigated whether uPAR can provide spatial guidance for podocyte migration. A modified scrape wound assay was used to study podocyte directional movement. The distance from the wound margin migrated by cells was related to the total distance of the scar and expressed as percentage closure 12 h after post-wound incubation. Untreated cells were observed migrating into the scar towards the midline of the wound (31%, FIG. 12C). However, LPS- or PAN-pretreatment significantly promoted wound closure, as podocytes moved much closer to the midline and began to refill the wound track (LPS 71%, PAN 63%, FIG. 12C). In contrast, uPAR siRNA significantly inhibited directional podocyte migration, leaving the wound largely unchanged (FIG. 12C). These data show that uPAR is required for directional podocyte migration.

Figure 13A:
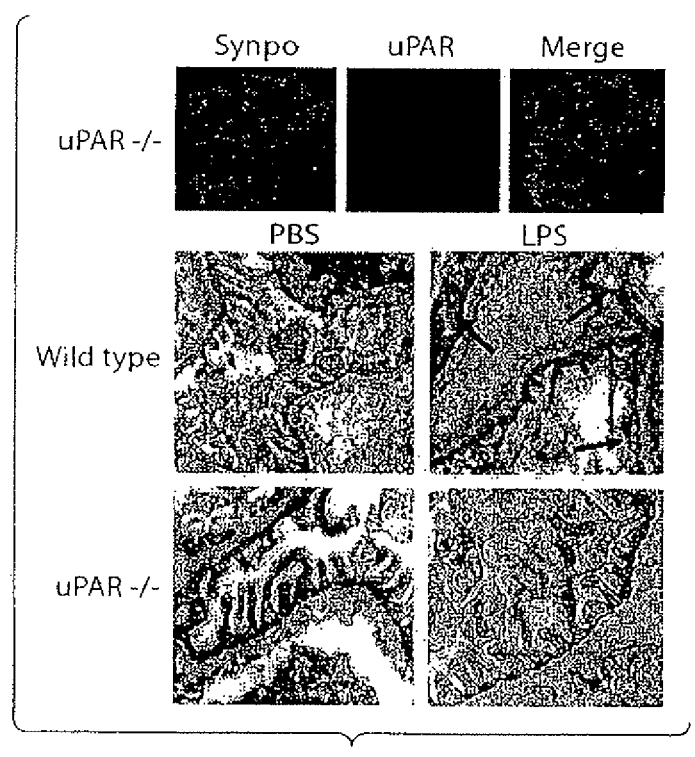
FIG. 13 is a panel of immunostaining images (A, B) and a bar graph (C) showing uPAR is required for the development of proteinuria and foot process effacement in mice. A) uPAR−/− mice were protected from LPS induced FP effacement. The absence of podocyte uPAR in uPAR−/− mice was confirmed by double immunofluorescent staining. TEM revealed no difference of podocyte ultrastructure between PBS treated wild type and uPAR−/− mice. Extensive FP effacement was observed in LPS injected wild type but not in uPAR−/− mice. B) uPAR gene transfer restored uPAR expression into uPAR−/− mouse podocytes, as indicated by immunostaining, whereas synaptodocin was unaffected. Podocyte ultrastructure was not affected by uPAR gene delivery itself uPAR reconstituted mice developed extensive FP effacement after LPS injection. C) Dipstick proteinuria. LPS injection induced proteinuria in wild type BL6 mice, but not in uPAR−/− mice. After uPAR gene delivery, uPAR−/− mice developed proteinuria upon LPS injection. * $p<0.05$ for LPS versus PBS treated mice.

To study the role of uPAR in the development of FP effacement in vivo, uPAR−/− mice were analyzed before and after injection of LPS. The absence of uPAR from podocytes of uPAR−/− mice was confirmed by double immunofluorescent labeling of uPAR with synaptopodin (FIG. 13A). LPS injection causes transient B- and T-cell independent podocyte FP effacement and proteinuria in mice. 24 h after LPS injection, electron microscopy analysis of the kidneys showed FP effacement in wild type but not in uPAR−/− mice (FIG. 13C) providing a functional link between the development of podocyte FP effacement and uPAR expression in this model.

Figure 13B:
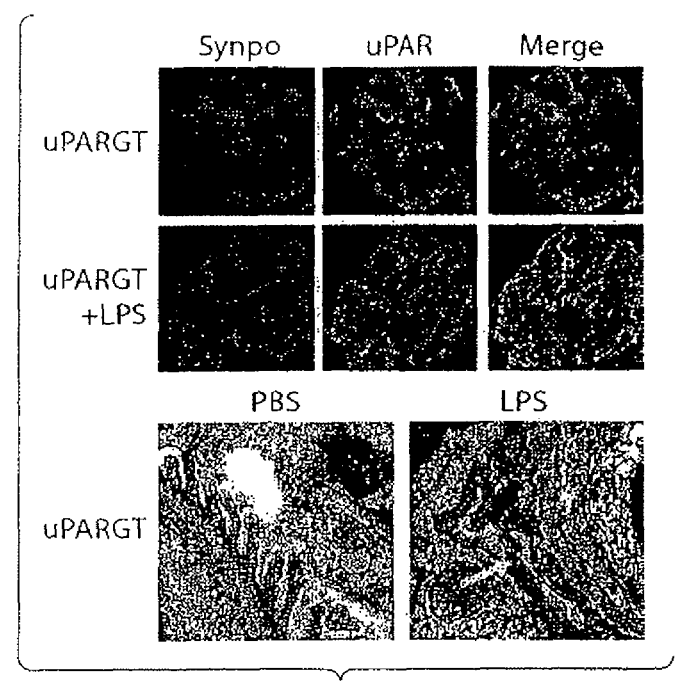

It was asked whether the protection from LPS-induced podocyte FP effacement could be abrogated by the restoration of uPAR expression into podocytes of uPAR−/− mice. A gene delivery protocol was utilized, which has been used before successfully to deliver genes to podocytes. 8 h after uPAR gene delivery, uPAR expression in podocytes was found, as indicated by double-immunofluorescent labeling of uPAR and synaptopodin (FIG. 13A). The expression of uPAR in podocytes peaked 24 h and was present up to 96 h after the uPAR gene delivery. The restoration of uPAR expression in podocytes did not change FP ultrastructure (FIG. 13B). uPAR-reconstituted mice were treated with LPS or PBS control injection respectively. Whereas PBS injected, uPAR-reconstituted mice had normal podocyte FPs, the injection of LPS led to extensive FP effacement (FIG. 13B). This data demonstrate the uPAR is necessary for the development of LPS-induced podocyte FP effacement.

Figure 13C:
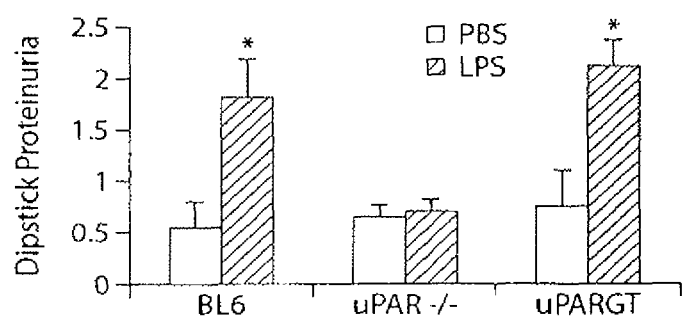
Figure 14A:
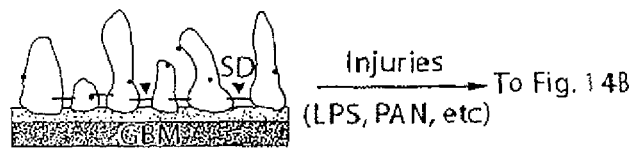
FIG. 14 is a diagram that illustrates uPAR mediation of directed podocyte motility. A) Under normal condition, uPAR expression is low in podocytes. B) Upon podocyte injury (e.g. LPS, PAN) uPAR is induced and enriched in lipid rafts of the SD. C) The SD site is transformed in a migratory pole resulting in spreading of FPs on the GBM. D) FP effacement is the result of uPAR induced directed podocyte motility. SD slit diaphragm, GBM glomerular basement membrane, FP foot processes
Figure 14B:
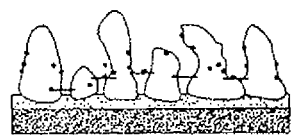
Figure 14C:
Figure 14D:
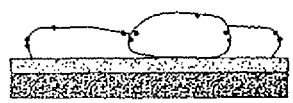
Figure 15:
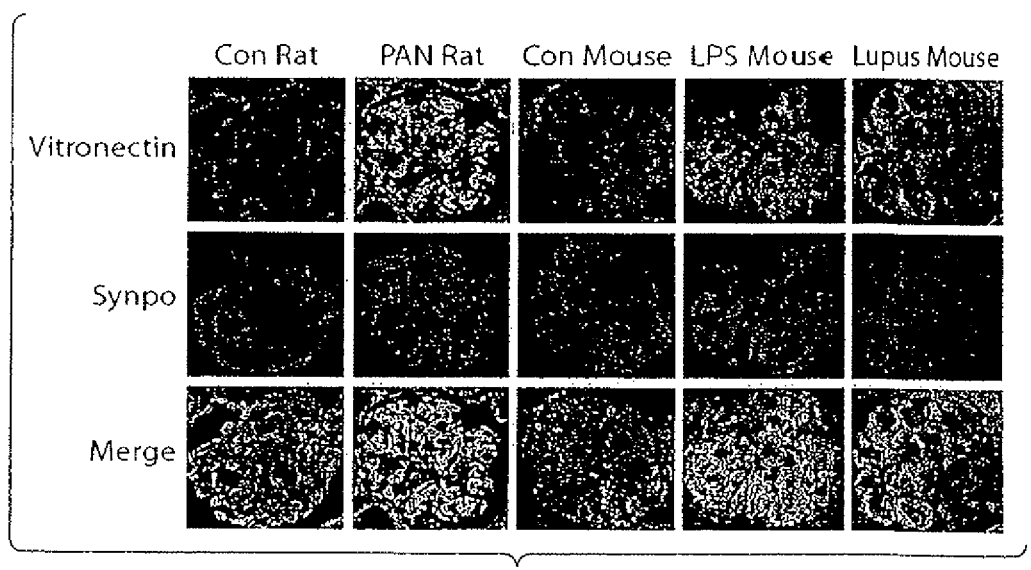
FIG. 15 is a panel of immunostaining images showing upregulation of vitronectin in podocytes of experimental proteinuric kidney diseases. Confocal microscopy reveals only low level of vitronectin expression (green) in glomeruli of normal rat or mouse. It partially co-localized with a podocyte marker, synaptopodin (red), resulting in a minimal yellow overlap. Vitronectin was significantly upregulated in podocytes in rat PAN nephrosis, mouse LPS transient nephrotic syndrome and lupus nephritis, resulting in an obviously enhanced yellow pattern. Con, control; Synpo, synaptopodin.

To study the functional consequences of uPAR reconstitution on the development of proteinuria, the urine protein excretion of wild type, uPAR−/− and uPAR-reconstituted mice before and after LPS injection was analyzed (FIG. 13C). Whereas control mice and uPAR−/− mice did not display any significant proteinuria (0.5+), the injection of LPS induced heavy proteinuria (2++) in wild type mice but not in uPAR−/− mice, indicating that uPAR−/− mice were protected from urinary protein loss. However, mice reconstituted with uPAR did develop heavy proteinuria after LPS injection but after injection with control buffer (PBS), (FIG. 13C). These data indicate that uPAR is essential for the development of LPS-induced FP effacement and proteinuria in mice.

In summary, it was found that uPAR plays a novel critical role in providing directional control in podocytes, and in mediating the pathophysiological process of podocyte membrane remodeling that leads to the development of urinary protein loss. This function of uPAR is initiated by an induced expression and by a relocation into lipid raft microdomains at the SD. Activated uPAR at the SD is located at the ideal sites to initiate FP effacement (FIG. 14). The induction of podocyte uPAR in both animal and human proteinuric kidney diseases suggests this mechanism to be widely operative. Spatial coordination of FP remodeling is necessary for the development of FP effacement. The lack of an overt kidney phenotype in untreated uPAR−/− mice fits well with the model of increased podocyte migration under pathological but not under normal conditions.

Materials and Methods

Animals and treatments. All animal studies were approved by the Subcommittee on Research Animal Care. uPAR−/− mice were obtained from University of Leuven, Belgium, NZB/W F$_1$ mice were purchased from Japan SLC (Shizuoka, Japan), C57BL6 mice were obtained from Jackson Laboratory (Bar Harbor). LPS induced mouse proteinuria model was utilized as previously described (Reiser, J. et al. J Clin Inves 113; 1390 (2004); Asanuma, K. et al., J Clin Inves 115; 1188 (2005)). Rat PAN nephrosis model was set up by a single intraperitoneal injection of PAN (15 mg/100 g of body weight, Sigma-Aldrich) into Sprague-Dawley rats as described before (Nakamora, T. et al., Lab Invest; 64; 640 (1991)).

Patients.

Microdissected glomeruli from 34 patients with proteinuric diseases and 8 control subjects were analyzed. Patients were stratified according to their histologic diagnosis into focal and segmental glomerulosclerosis (FSGS; n=14), and diabetic nephropathy (DN, n=20). For control biopsies, renal tissue was derived from pretransplantation kidney biopsies during cold ischemia time from 7 living and 1 cadaveric donors (n=8).

Immunohistochemistry and Immunocytochemistry.

Mice or rats kidneys were harvested and snap-frozen. Fixation and sectioning were following standard protocols. For double-immunofluororescent staining, sections were blocked for 30 min at room temperature, then incubated with anti-mouse synaptopodin (pure), and anti-rabbit uPAR (1:50) or anti-rabbit vitronectin (1:50) (Santz Cruz Biotech Inc) for 1 h respectively. After washing with PBS, sections were incubated with Alexa Fluor 568 conjugated anti-mouse and Alexa Fluor 488 anti-rabbit antibodies (1:1000, Molecular Probes) for 45 min. Thereafter, sections were washed with PBS, and $H_2O$ and mounted for view with a confocal microscope (Bio-Rad Laboratories).

Immunocytochemistry was done on podocytes growing on cover-slips. Primary antibodies against uPAR and podocin (1:200) were used. To label lipid rafts, we used cholera toxin subunit B, Alexa Fluor 594 conjugate (1:50, Molecular Probes Inc).

Transmission Electron Microscopy (TEM), Immunoelectron Microscopy (IEM).

TEM and IEM were performed according to the standard protocols as previously described (Reiser et al., J Am Soc Nephrol 11; 1 (2000)).

Cell Culture and Transient Transfection.

WT podocytes were cultured as described before (Mundel, P. et al., Esqr (24 Res 236; 248 (1997)). A uPAR-GFP construct was generated by inserting mouse uPAR cDNA into pEGFP-C2 (Clontech). For transient transfection, podocytes were seeded on a 6-well plate, cultured under non-permissive conditions for 10 days, and then transfected with 4 μg of uPAR-GFP by Lipofectamine™ 2000 (Invitrogen) following the manufacturer's protocol.

siRNA.

Mouse uPAR siRNA (sense: CTTCCTGAAGTGTTG-CAACTA; SEQ ID NO. 24) was constructed and inserted into a pRNA-H1.2/Neo vector (Genescript). Stable transfection was done with podocytes maintaining at 33° C. by Lipofectamine™ 2000. Positive clones were selected by G418 (Sigma-Aldrich) at 500 μg/ml. For further experiments with uPAR siRNA, cells were grown under non-permissive conditions for 14 days before proceeded with migration experiments.

Migration Assay.

Podocyte migration was analyzed using a 12-well chemotaxis chamber (Neuro Probe) according to the manufacturer's protocol. In brief, differentiated podocytes were treated with 50 μg/ml of LPS or PAN for 24 h and then harvested for the migration assay. Bottom plates were coated with type-I collagen, while upper plates were loaded with equal number of cells ($5 \times 10^4$) suspended in medium. The chamber was incubated at 37° C. for 4 h before unassembled. The membrane was then taken out, processed and finally stained with diamidino phenylindole (DAPI) (Vector). The average number of migrated cells was counted in four fields in six independent experiments.

Wound Healing Assay.

To study the directional movement of podocytes, wound healing assay was performed. Briefly, podocytes were densely seeded on collagen or vitronectin coated cover-slips and cultured for 14 days at 37° C. before treated with LPS or PAN for 24 h. To create a scrape wound approximately 0.1 cm wide, the narrow end of a P1000 pipette tip was perpendicularly pushed through the monolayer. Cover-slips were then washed twice with PBS and incubated in full medium for 12 h. After incubation, cells were fixed with 2% PFA and stained with DAPI for analysis. The cell migratory distance was calculated by averaging the distance from the wound edge to the DAPI-labeled nucleus of the maximally migrated cell in five distinct border zones. The percentage of closure was calculated as migratory distance from both sides versus initial wound track width.

Western Blotting.

For western blotting, podocytes were lysed in RIPA buffer containing a cocktail of protease inhibitors. The lysate was centrifuged for 20 min at 10,000 rpm and the supernatant was kept. Total protein assay was performed to ensure equal amount of loading. Proteins were separated by 10% SDS-PAGE gels and then transferred to a PVDF membrane. After blocking for 30 min with 5% milk, the membrane was incubated with primary antibody for 1 h, followed by secondary antibody for 1 h. After washing, the membrane was visualized by enhanced chemiluminescence (ECL) immunoblot detection kits (Pierce).

Sucrose Gradient Ultracentrifugation.

Preparation of detergent-resistant membranes (DRMs) was performed as described previously (Schwarz, K. et al., J Clin Invest, 108; 7621 (2001). Briefly, cultured podocyte lysates were incubated on ice for 45 min in the presence of 0.2% Triton X-100 and 40% sucrose. Samples were then overlaid with a sucrose step gradient and centrifuged for 20 h at 120,000 g at 4° C. in a swing-out rotor. 12 fractions (1 ml) were collected starting from the top and analyzed by Western blotting with uPAR or podocin primary antibodies.

GST pull-down assay. GST pull-down assays were performed as reported previously (Schwarz, K. et al., J Clin Inves, 108; 1621 (2001)). In brief, fusion proteins were expressed in E Coli in the presence of 2 mM isopropyl-β-d-thiogalactopyronoside. Cells were lysed, centrifuged and the supernatants were then applied to the prepacked fast-flow Gluthathione Sepharose 4B columns (Sigma-Aldrich) according to the manufacturer's instructions. After uploading the podocyte lysates, the columns were properly washed and the bound fusion protein was eluted with 4 volumes of elution buffer (10 mM reduced glutathione in 50 mM Tris, Ph 8.0). The elutes were then collected and analyzed by Western blotting.

In Vivo Gene Delivery.

uPAR-GFP plasmids were introduced into mouse using the TransIT in vivo gene delivery system according to the manufacturer's instruction (Mirus). In brief, 15 μg of uPAR-GFP or control vectors was mixed with 15 μl polymer solution and 170 μl of endotoxin-free $H_2O$. It was then topped up with 1.8 ml delivery solution before injection through tail vein. 24 h after gene delivery, proteinuria was assessed by Multistix 8 SG strips (Bayer Corporation) and Bradford protein assay and mice were sacrificed for TEM and immunohistochemistry.

Quantitative RT-PCR.

TaqMan real-time RT-PCR was done as previously reported (Schmid, H. et al., J Am Soc Nephrol, 14, 2958 (2003)). Commercially available predeveloped TaqMan assay reagents (Applied Biosystems) were used for uPAR mRNA analysis. The mRNA expression of uPAR was related to that of synaptopodin, which worked as a podocyte reference gene (primer oligonucleotide sequences: sense CCCAAGGTGACCCCGAAT (SEQ ID NO. 25), antisense CTGCCGCCGCTTCTCA (SEQ ID NO. 26), internal probe sequence: ACTTGCTGGATCTGGTACAGACAGCGG (SEQ ID NO. 27)). Using this approach, the confounding factor of alterations in the proportion of podocyte cell number per total glomerular cells was counterbalanced, and only RNA from the podocyte compartment of the glomerulus was integrated in the analysis, as demonstrated recently (Schmid, H. et al., J Am Soc Nephrol, 14, 2958 (2003)).

Statistical Analysis.

Statistical analyses were performed by using a Student t-test, and the null hypothesis was rejected at the 0.05 level. Values were presented as Mean±SD, unless stated otherwise.

Example 4

Processing of the GTPase Dynamin by Cytoplasmic Cathepsin L Defines a Mechanism for Proteinuric Kidney Disease CatL is Important for Podocyte FP Effacement and Proteinuria in a Mouse Model.

Figure 16A:
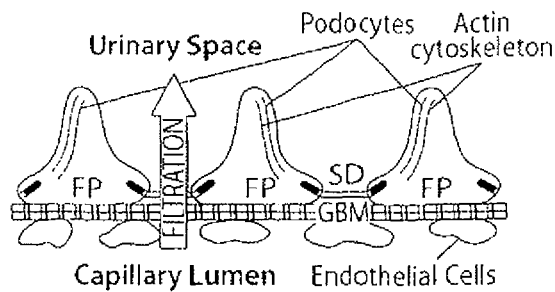
FIG. 16 is a panel of a scheme (A), immunocytochemistry images (B,C), electron micrographs (D, E, F), bar graph (G) and tissue slides (H, I) that show CatL is essential for proteinuric kidney diseases. A) Schematic depiction of the kidney filtration barrier that consists of podocyte foot processes (FP), slit diaphragm (SD), glomerular basement membrane (GBM) and endothelial cells. Filtration occurs from the capillary lumen into the urinary space. B, C) Immunocytochemistry of mouse glomeruli using monoclonal anti-CatL antibody before (B), and after (C) LPS injection. D, E, F) Electron micrographs of FPs in CaL−/− mice after LPS injection (D), and wild type mice before (E), and after (F) LPS injection. G) Quantitative real-time RT-PCR of microdissected glomeruli from human biopsies of patients with acquired proteinuric diseases minimal change disease (MCD; n=7), membranous glomerulonephritis (MGN; n=9; p<0.01), focal segmental glomerulosclerosis (FSGS; n=7; p<0.01), and diabetic nephropathy (DN; n=10; p<0.01). Control (CON, n=8). H) CatL labeling of normal human kidney. I) CatL labeling of human kidney with diabetic nephropathy.
Figure 16B:
Figure 16C:
Figure 16D:
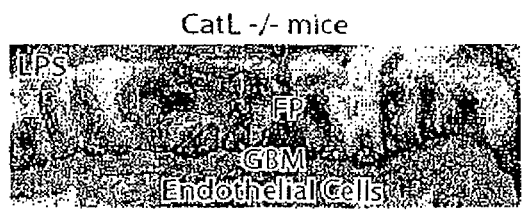
Figure 16E:
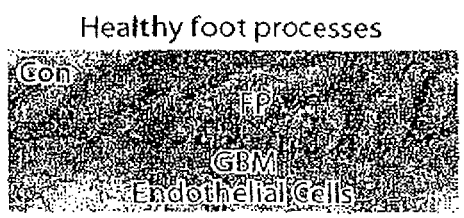
Figure 16F:
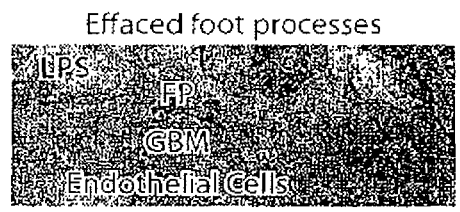

This experiment examined whether upregulation of CatL occurs in the lipopolysaccharide (LPS) mouse model of proteinuria Immunocytochemistry using anti-CatL antibodies detected weak CatL staining in normal glomeruli (FIG. 16), as described before in normal rat glomeruli. CatL labeling increased within glomeruli 24 hours after a single LPS-injection (FIG. 16). LPS treatment resulted in FP effacement (FIGS. 16E and 16F) and urinary protein increased from a baseline of ~0.25 mg/ml to 1.2±0.15 mg/ml, which is considered proteinuric. Strikingly, CatL-/- mice were protected from LPS-induced FP effacement (FIGS. 16D and 16F). In addition, proteinuria was absent in LPS challenged CatL-/- mice (0.25±0.11 mg/ml). These data suggest that CatL could be important to induce proteinuria in rodent models.

CatL is Upregulated During Human Proteinuric Kidney Diseases.

Figure 16G:
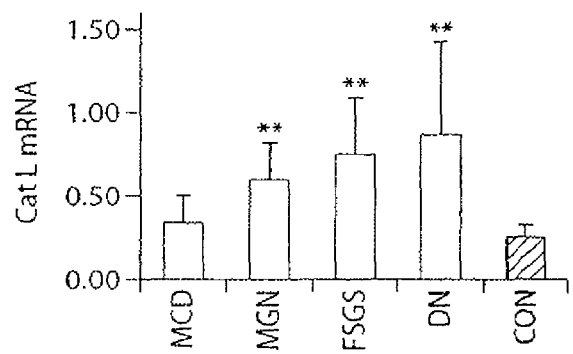
Figure 16H:
Figure 16I:

CatL mRNA levels were examined using quantitative real-time (RT)-PCR on microdissected glomeruli from patients with acquired proteinuric diseases. Three types of proteinuric kidney diseases, membranous glomerulonephritis (MGN), focal segmental glomerulosclerosis (FSGS) and diabetic nephropathy (DN) had two-fold or greater CatL mRNA levels compared to controls (FIG. 16G). Minimal change disease (MCD), which is characterized by reversible podocyte FP effacement, showed only a minor increase. It appeared that the increase in CatL mRNA correlated with the severity of podocyte damage and the progressive nature of the disease, with MCD being a disease with a high degree of reversibility. In agreement with the increase in mRNA levels for CatL, there was a significant increase in staining for CatL in the glomerulus of patients with diabetic nephropathy (FIGS. 16H and 16I). The glomerulus contains three major cell-types: podocytes, endothelial cells, and mesangial cells. CatL was detected in the nuclei of glomerular cells. Mesangial cells had a lower incidence of nuclear CatL staining (FIG. 16I). There was a strong increase in CatL in the Bowman's capsule (FIG. 16I) and proximal tubules as shown in proteinuric states before. Finally, CatL staining was also elevated in the cytoplasm of podocytes (FIG. 16I). These results suggest that CatL could be a factor in the development of proteinuric kidney disease in humans, as seen in rodent models.

LPS Induces Expression of Cytoplasmic CatL.

Figure 17A:
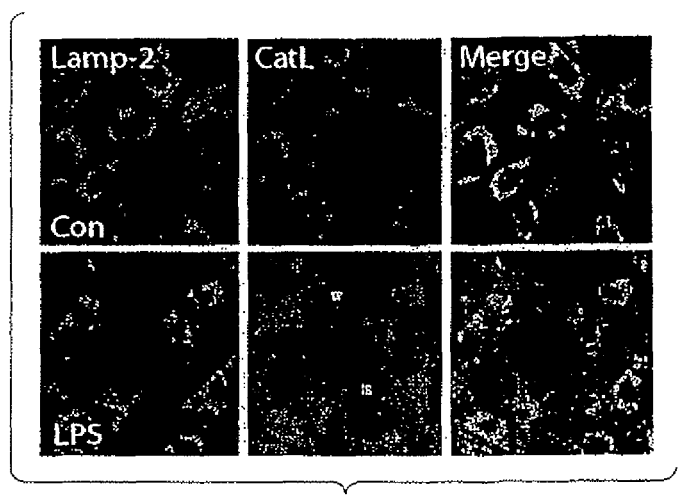
FIG. 17 is a panel of immunostaining images (A, B, E, F), a scheme (C) and a Western blot (D) that show induction of cytoplasmic CatL protein and activity by LPS. A, B) Labeling of cultured podocytes using anti-CatL antibody (A), CatB (B) and anti-Lamp-2 antibody. Staining was carried out in untreated cells, or cells treated with 50 Ng/ml of LPS for 24 hours (LPS panels). C) Schematic of CatL mRNA and resulting proteins. D) Subcellular fractionation of podocytes in isotonic sucrose prior (control) and 24 h and 48 h after LPS treatment (LPS). Total proteins from the soluble (S) and the particulate (P) fractions were analyzed by Western blotting using antibodies as indicated in the figure. E) Lysosomal leakage assay using Lucifer Yellow. Lysosomes of untreated control cells, cells after LPS treatment, and cells after treatment with sphingosine (lysosomal leakage) were analyzed for the presence of Lucifer Yellow. F) Cultured podocytes were stained using anti-Lamp-2 antibodies and BIOMOL CV-CatL/B activity detection kit. Control cells (upper panel), cells treated with 50 pg/ml of LPS for 24 h LPS (middle panel), and cells treated with LPS and 1 pM of a selective CatL inhibitor Z-FF-FMK (lower panel) are shown.
Figure 17B:
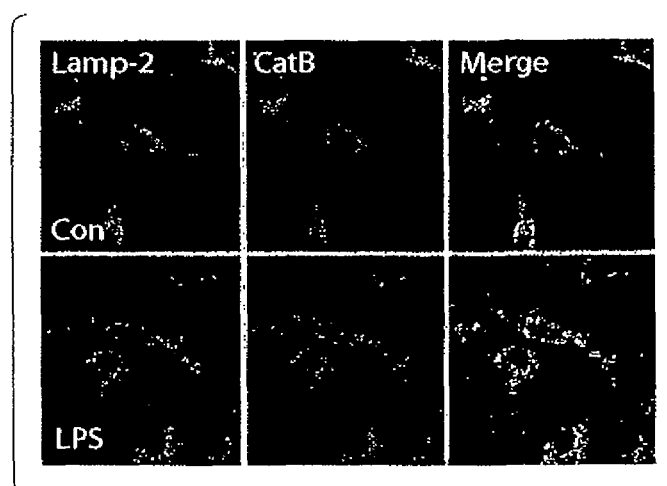
Figure 23A:
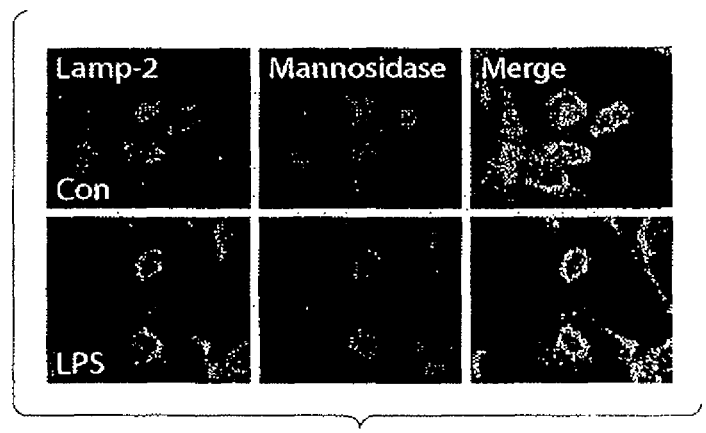
FIG. 23 is a panel of immunostaining images (A, B, C), a scheme (D), and Western blots (E, F) further illustrating the invention. A) Cultured podocytes were stained with anti-mannosidase alpha antibody and anti-Lamp-2 antibody to specifically label lysosomes. Staining was carried out in untreated cells (upper panels), or cells treated with 50 µg/ml of LPS for 24 h (lower panels). B) Labeling of cultured podocytes using anti-CatL antibody and anti-Lamp-2 antibody. Staining was carried out in cells treated with 50 µg/ml of LPS for 24 h. C) Double immunofluorescence of cultured CatL−/− fibroblasts after transfection with a control vector (upper panel), HA-tagged long CatL (middle panel) and HA-tagged short CatL (lower panel). D) Schematic of CatL mRNA and resulting proteins. E) Subcellular fractionation of podocytes after transfection with HA-tagged long CatL, and HA-tagged short CatL and Western Blot using anti-HA antibodies (lanes 1-4). F) Detection of endogenous WT-1 transcription factor from fractionated podocyte lysates (lanes 1-3), Nuc=nucleus.
Figure 23B:
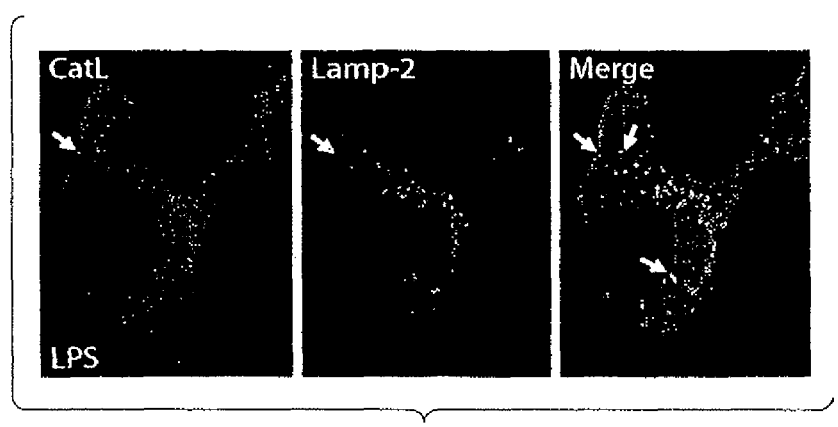

Subcellular distribution of CatL was examined before and after LPS treatment. CatL co-localized with the lysosome-associated membrane protein Lamp-2 in control podocytes (FIG. 17A). Strikingly, after LPS treatment there was a dramatic, overall increase in staining for CatL (FIG. 17A, LPS), and it was no longer limited to sites of Lamp-2 staining, being distributed throughout the cytosol and in the nucleus. Some of the induced CatL was seen in Lamp-2 positive vesicles extending in podocyte processes close to the plasma membrane, which likely represent vesicles targeted for secretion (FIG. 23B). The relocalization of CatL upon LPS treatment was specific since other lysosomal proteases such as CatB (FIG. 17B) and mannosidase alpha (FIG. 23A) co-localized exclusively with Lamp-2 before and after LPS treatment. Thus, CatL localization in cultured podocytes and in glomeruli (FIG. 16I) are strikingly similar both under normal and proteinuric conditions.

Next the reason for the relocalization of CatL in LPS treated podocytes was examined. To examine the possibility of lysosomal leakage, the localization of Lucifer Yellow, a cellular dye that is readily taken up into lysosomes was examined. Lucifer Yellow was found in perinuclear lysosomes in the presence and absence of LPS (FIG. 17E, Con and LPS), suggesting that lysosomal integrity was not disrupted by LPS. In contrast, the administration of sphingosine led to the expected lysosomal rupture, as seen by diffuse staining of Lucifer Yellow within the perinuclear cytoplasm (FIG. 2E, sphingosine). Therefore, lysosomal leakage does not account for cytoplasmic CatL after LPS treatment.

Figure 17C:
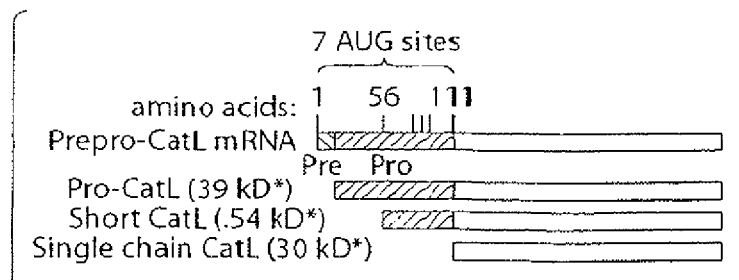

Next it was investigated whether translational regulation might be involved in CatL relocalization. The mRNA for CatL contains several AUG codons (FIG. 17C). Alternative translation initiation from a downstream AUG results in a CatL isoform devoid of a lysosomal targeting sequence. The resulting cytoplasmic CatL isoform can enter the nucleus in S-phase of the cell cycle to cleave the CDP/Cux transcription factor. Thus, it seemed possible that LPS might induce alternative translation in podocytes to generate cytoplasmic CatL.

Figure 17D:
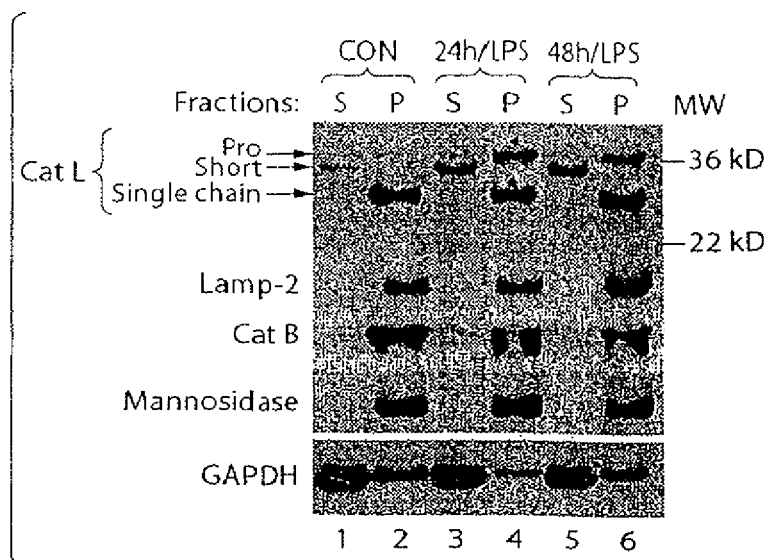
Figure 17E:
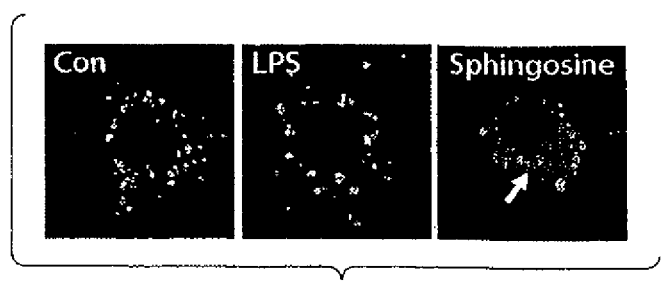
Figure 23C:
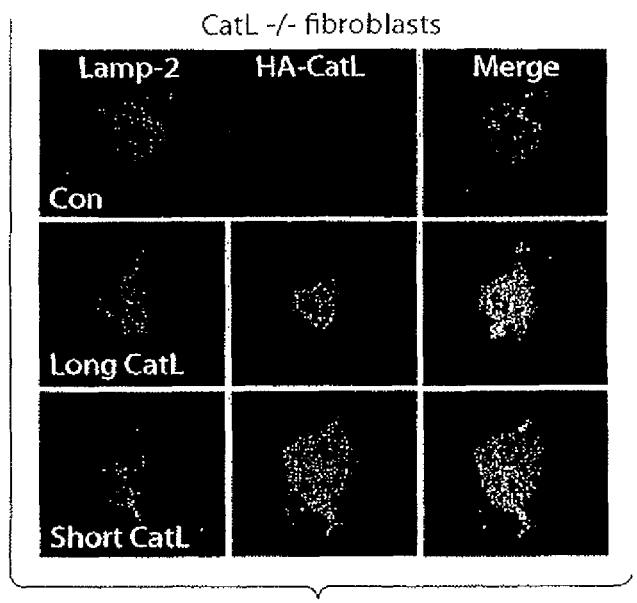

Hence, subcellular fractionation experiments using cultured podocytes were performed. The particulate fraction contains membranes, including lysosomes, whereas the soluble fraction represents cytoplasm. GAPDH was used as a marker for soluble cytosolic proteins and the efficiency of lysis. As expected, mature single chain CatL (30 kD) was present in the particulate fraction, which also contained Lamp-2, CatB and mannosidase alpha (FIG. 17D, lane 2). LPS treatment for 24 and 48 hours led to strong induction of a 34 kD "short" form of CatL, which was present exclusively in the cytoplasm (FIG. 17D, compare lane 1 with 3 and 5). In contrast, there was no significant increase in the amount of 30 kD CatL present within the lysosomes (FIG. 17D, lanes 2, 4, 6). The same was true for the overall amount of CatB, Lamp-2, and mannosidase alpha, demonstrating that LPS was specifically inducing expression of the short CatL. In addition, the soluble fractions were not contaminated with nuclear proteins such as transcription factor WT-1 (FIG. 23H). Interestingly, addition of LPS also induced expression of the 39 kD proCatL for secretion (FIGS. 17D and 23B). The ability of mRNA for CatL to initiate translation from the downstream AUG codons and thus generate cytoplasmic CatL was confirmed by transiently transfecting CatL-/- fibroblasts with a cDNA in which the first AUG codon had been mutagenized (FIGS. 23C and 23G).

Figure 17F:
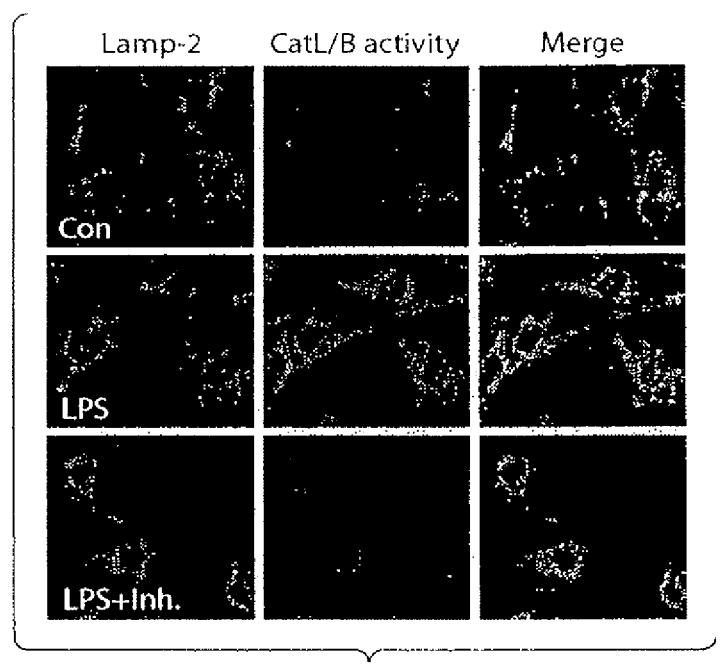

Finally, it was examined whether CatL can be enzymatically active in the cytosol. Subcellular sites of CatL and CatB activity were visualized by a fluorogenic substrate, CV-(FR)$_2$, which emits light upon cleavage by CatL. In untreated podocytes, protease activity was low and confined to perinuclear lysosomes (FIG. 17F). LPS treatment dramatically increased protease activity, which now extended outside lysosomes into the cytoplasm (FIG. 17F, LPS panel). The vast majority of extralysosomal cathepsin activity after LPS administration was sensitive to the CatL inhibitor Z-FF-FMK, which does not inhibit CatB (in FIG. 17F, notice only perinuclear staining). Together, these data show that LPS induces expression of an enzymatically active 34 kD cytoplasmic form of CatL that is translated from the downstream AUG codons.

Loss of Dynamin Staining in Podocytes Correlates with the Onset of Proteinuria and is CatL-Dependent.

Since FP effacement is thought to result from actin reorganization, it was examined if cytoplasmic CatL cleaves proteins that regulate actin dynamics. Among this class of proteins, the GTPase dynamin was identified as a potential CatL substrate by a computer-based algorithm termed 'PEPS' (Prediction of Endopeptidase Substrates (Lohmuller et al., Biol Chem 384; 899-909 (2003)). Thus, first dynamin distribution in podocytes using immunogold electron microscopy was examined As shown in FIG. 18A, dynamin antigenic sites were detected within FPs of rat kidney cortex using a monoclonal antidynamin antibody coupled to 10 nm gold particles. Gold particles were associated with the cytoplasmic side of coated vesicles (FIG. 18A, labeled V), electron dense dark areas rich in cortical actin (FIGS. 18A and 18B, labeled a), and they were also present in the center of FPs, which contain parallel actin bundles (FIG. 18B, asterisk). The electron dense appearance of the vesicles (V) and their round morphology both suggest that they are coated with clathrin. The presence of dynamin on clathrin coated pits is in agreement with its role in endocytosis, while the association with actin suggests a role in actin dynamics in podocytes.

Figure 23D:
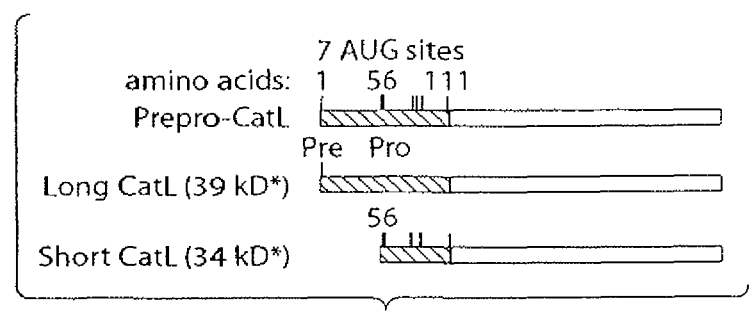
Figure 23E:
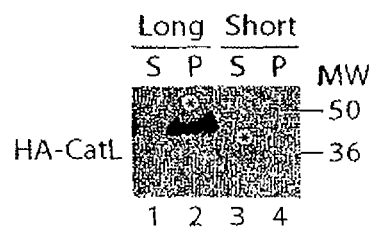
Figure 23F:
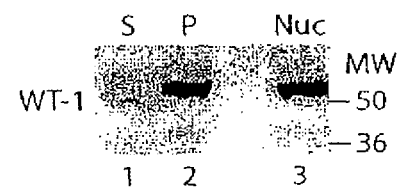
Figure 24A:
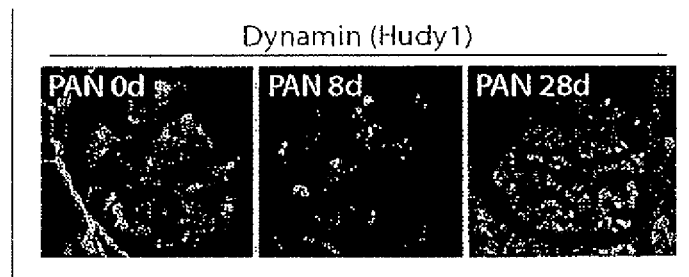
FIG. 24 is a panel of immunostaining images (A, B), immunoblot (C), and a bar graph (D), further illustrating the invention. A) Immunocytochemistry of dynamin in rat kidney using Hudy-1 antibody during PAN-nephrosis. B) Transient gene expression of short and long CatL Immunocytochemistry of CatL−/− mice glomeruli 24 h after LPS injections (LPS panel) or 24 h after cDNA injections encoding long or short forms of CatL. Glomeruli were stained using anti-CatL and anti-dynamin hudy 1 antibody. C) Immuoblot of CatL in wild type podocytes and after stable knockdown of CatL using siRNA. D) Quantitative PCR analysis of CatL in wild type and CatL knockdown podocytes.
Figure 24B:
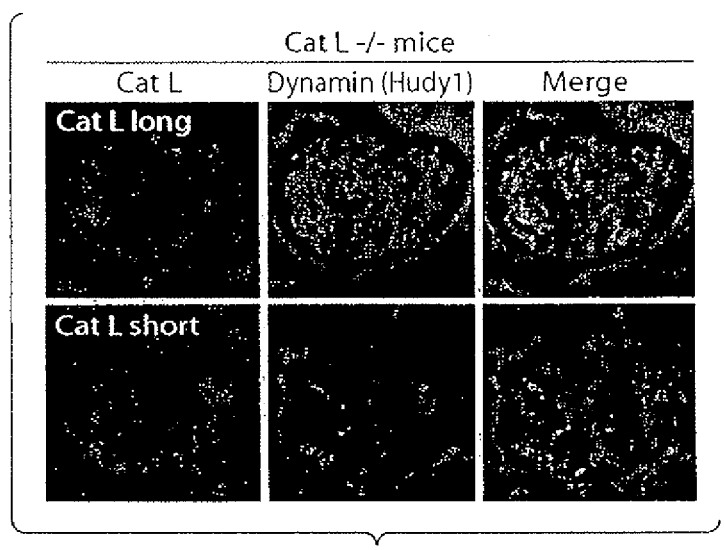

Next, dynamin staining in mice before and after LPS treatment was examined. Immunocytochemistry in control mice detected dynamin staining in glomeruli (FIG. 18C). 24 h after a single LPS-injection, dynamin labeling was significantly altered when compared to the control animals, with reduced and clustered staining in glomerulus (FIG. 18D), but remained unchanged in tubules. A similar dynamin staining pattern was observed in a rat model for proteinuric kidney disease in which animals are injected with puromycin aminonucleoside (PAN), (FIG. 24A), suggesting that changes in glomerular dynamin staining are characteristic of proteinuria. Importantly, dynamin staining was preserved in CatL−/− mice treated with LPS (FIG. 18E), suggesting a link between CatL induction and altered dynamin staining. To examine whether changes in dynamin staining were due to expression of the short cytoplasmic CatL, DNA expressing only short or only long forms of CatL (FIGS. 23D and 23E) were injected in CatL−/− mice using transient gene delivery. As shown in FIG. 24B, both DNA constructs resulted in expression of detectable levels of CatL. While dynamin staining was preserved if mice were injected with the long (lysosomal) CatL isoform (FIG. 24B, panel long), expression of the short CatL isoform resulted in changed dynamin staining (FIG. 24B, panel short) similar to the one observed in LPS treated wild type mice (FIG. 18D). Together, these data suggest that the presence of cytoplasmic CatL is responsible for changes in dynamin staining during proteinuria in mice.

Figure 18F:
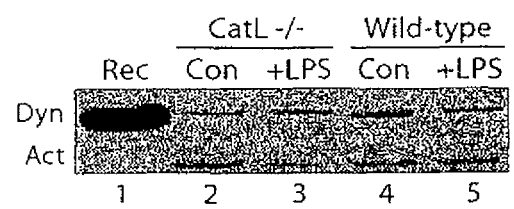
FIG. 18 is a panel of immunostaining images (A-E), an immunoblot (F) and a bar graph (G) that show altered dynamin staining in glomerulus after LPS treatment is CatL dependent. A) Immunogold analysis of dynamin in podocyte FPs in situ. PAN treated rats were studied after 6 days. A) Gold particles are associated with the cytoplasmic side of vesicles (v), and with electron dense actin areas (a), (magnification ×45,000). The bracket indicates accumulation of dynamin along the cell membrane around a vesicle. E: endosome; Ly: lysosome; GBM: glomerular basement membrane; US: urinary space. B) Association of dynamin with the actin cytoskeleton in podocyte foot processes. Dynamin is associated with the cortical actin (a) as well as with parallel actin bundles running in the center of the foot processes (asterisk) (magnification ×30,000). C, D, E) Immuno-cytochemistry of mouse glomeruli using monoclonal antidynamin hudy 1 antibody before (C), and after (D, E) injection of LPS. Nephrosis was induced by injection of LPS (200 μg/20 g body weight). F) Immunoblot of endogenous dynamin in cultured podocytes. (1) recombinant dynamin, CatL−/− podocytes (2) before and (3) after LPS, wild-type podocytes (4) before and (5) after LPS. G) Quantification of dynamin expression in wild-type and CatL−/− podocytes before and after LPS treatment. Dynamin signal was adjusted to actin levels.
Figure 24C:
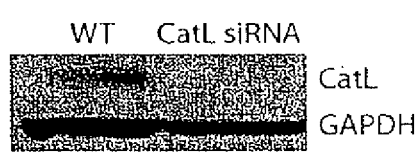
Figure 24D:
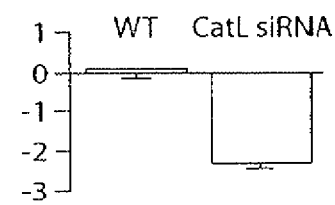

Without wishing to be bound by theory, the change in dynamin staining could be due to (1) proteolysis, (2) different subcellular distribution, and/or (3) altered biochemical properties (e.g., dynamin self-association could impair antibody accessibility). Western blotting of podocyte lysates revealed a ~30% decrease in the amount of endogenous dynamin after LPS treatment (FIG. 18F, compare lanes 4 and 5 and see quantification in FIG. 18G, columns 1 and 2). Importantly, when CatL was downregulated using stable expression of a CatL siRNA (FIGS. 24C and 24D), the reduction in dynamin was not observed (FIG. 18F, compare lanes 2 and 3, and 18G). Thus, changes in dynamin staining in the glomerulus and the decrease in the level of dynamin in cultured podocytes together suggest the possibility that dynamin is proteolyzed by CatL in proteinuric animal models.

CatL Cleaves Dynamin:GTP In Vitro and In Viva.

Figure 19C:
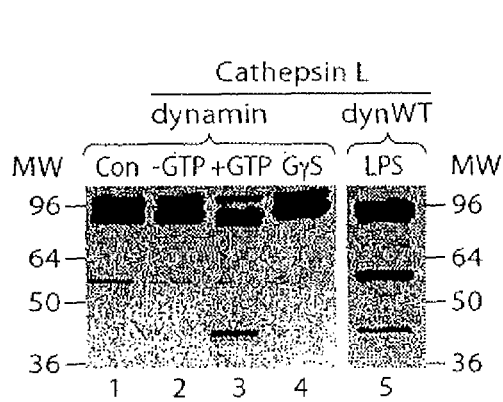
FIG. 19 is a panel of schemes (A, A'), amino acid sequences (B), and Western Blots (C-G) that show effects of the nucleotide-bound and assembly state of dynamin on CatL cleavage in vitro and in vivo. A) Domain structure of dynamin, corresponding antibodies and aminoacid sequence of predicted CatL cleavage sites. A') Schematic depiction of the dynamin's GTPase cycle. In its basal state, dynamin is a homotetramer. Self-assembly into higher order structures such as rings or spirals activates GAP-mediated GTP-hydrolysis, which in turn disassembles dynamin. B) The CatL cleavage site ELSGGA and flanking aminoacids are shown for several species. Note that the ELSGGA sequence is a highly conserved motif throughout the species and is found in dyn1 and 2 isoforms. C) Recombinant dyn1 (20 pmol) was mixed with CatL (1 pmol) at pH 7.0 under non-assembly conditions (200 mM NaCl). Where indicated, 200 NM GTP, or 1 mM GTPrS was present. Proteolytic products were detected by monoclonal anti-dynamin antibodies against the GTPase domain. Lane 5, cytosol from podocytes that were infected with dynWT and treated with LPS for 24 h. D) Silver staining of recombinant dynamin incubated with CatL at different pHs in presence or absence of $GTP_\gamma S$. E) Western blot analysis of subcellular fractionation of podocytes expressing dynWT 24 h after LPS treatment. Supernatant (S) and pellets (P). Extracts were blotted using antibodies against the GTPase domain, GAP domain, Lamp-2, and tubulin. F) Same as (C), except that the protease added was CatB or furin. G) Western blot analysis using GTPase antibody of cellular extracts of control podocytes (lanes 2-5) or podocytes treated with 100 μg/ml LPS for 20 h (lanes 6-10). Lane 1, 100 ng recombinant dynamin. Lane 6, cells were treated with 1 μM of a selective CatL inhibitor Z-FF-FMK for the duration of the LPS treatment.
Figure 19D:
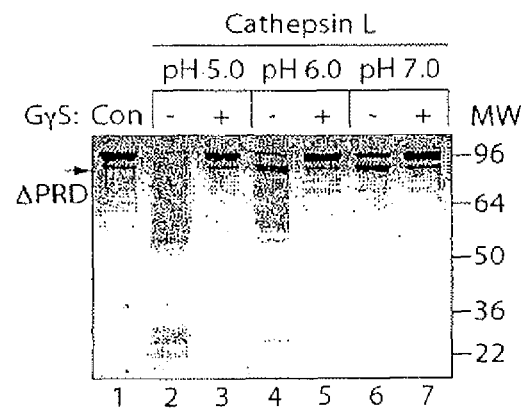
Figure 19E:
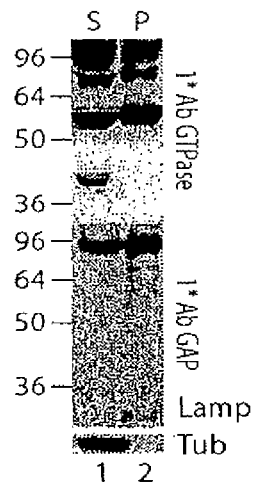
Figure 19F:
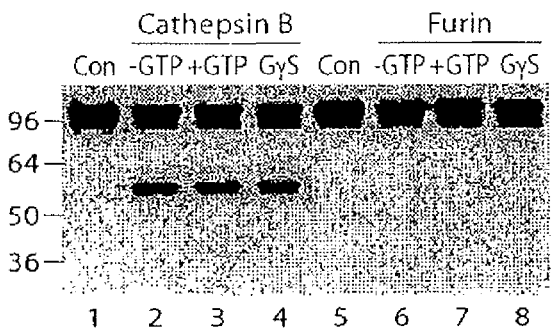

To further examine if proteolysis of dynamin by cytoplasmic CatL occurs during proteinuric kidney disease, it was examined whether purified dynamin is cleaved by CatL in vitro at neutral pH. The PEPS algorithm identified three putative CatL recognition motifs within dynamin (FIG. 19A): amino acids 55-59 (LPRGS; SEQ ID NO. 28) within the GTPase domain, 354-359 (ELSGGA; SEQ ID NO. 29) within the middle domain, and 614-618 (FLRAG; SEQ ID NO. 30) within the pleckstrin-homology (PH) domain. Interestingly, the ELSGGA motif is conserved from yeast to mammals (FIG. 19B). As shown in FIG. 19C, CatL did not cause significant cleavage of purified dynamin at pH 7.0 (compare lanes 1 and 2). Strikingly, addition of GTP resulted in the generation of a prominent proteolytic fragment with a molecular weight of ~40 kD (p40) (FIG. 19C, lane 3). The cleavage pattern obtained in vitro is almost identical to that observed in podocytes after addition of LPS (FIG. 18A, compare lanes 3 and 5). p40 is the predicted size of the N-terminal fragment after cleavage at the ELSGGA sequence (FIG. 19A; SEQ ID NO. 29). Another fragment, p55, is observed in the absence of added protease (FIG. 19C, lane 1), likely during protein preparation. Thus, p55 is not a precursor of p40. Furthermore, incubation of dynamin with CatB generated p55 in a nucleotide-independent manner (FIG. 19F, lanes 2-4), whereas furin, another protease also found in podocytes in vivo, was unable to cleave dynamin (FIG. 19F, lanes 6-8). Thus, while p55 is produced by a number of proteases and thus represents a "hot spot" for proteolysis, p40 is generated by CatL only when dynamin is in the GTP-bound conformation.

Interestingly, addition of GTP$_\gamma$S, (non-hydrolysable GTP analog) did not stimulate cleavage by CatL (FIG. 19C, lane 4). GTP$_\gamma$S promotes oligomerization of dynamin into higher order structures such as rings or spirals since the disassembly process, which requires GTP hydrolysis, is blocked. Dynamin oligomerization is mediated by the middle and GAP domains of dynamin. Based on a cryo-EM reconstruction of assembled dynamin, amino acids 356-ELSGGA-359, which are located in the middle domain, are predicted to be inaccessible when dynamin is self-assembled (FIG. 19A'). Thus, self-assembly of dynamin might protect from CatL cleavage.

To test this hypothesis, we performed additional cleavage experiments at acidic pH where CatL is more active. At pH 5.0 and 6.0, CatL was highly reactive towards recombinant dynamin, even in the absence of GTP (FIG. 19D, lanes 2 and 4). Strikingly, this proteolysis was completely inhibited by addition of GTP$_\gamma$S (FIG. 19D, lanes 3 and 5). This data suggests that the primary site recognized by CatL is situated within a domain that becomes inaccessible upon dynamin self-assembly.

Figure 19G:
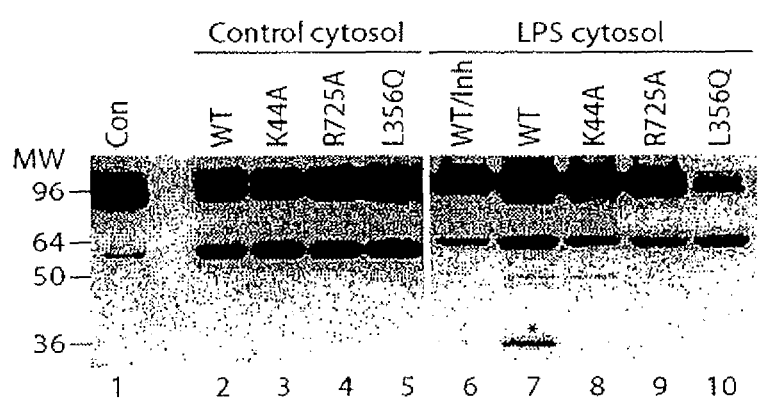

To explore CatL-mediated dynamin cleavage in vivo, cultured podocytes were infected with adenoviruses encoding different dynamin mutants and subsequently treated with LPS (FIG. 19G). As expected, addition of LPS to cells expressing dynWT resulted in generation of p40 (FIG. 19G, lane 7), which was inhibited by the addition of the CatL inhibitor Z-FF-FMK (FIG. 19G, lane 6). Importantly, LPS treatment of podocytes expressing dynK44A (a mutant that cannot bind GTP) did not result in detectable levels of p40 (FIG. 19G, lane 8), which is in line with in vitro cleavage of dynamin by CatL at neutral pH being GTP-dependent. To confirm the identity of the cleavage site, the ELSGGA (SEQ ID NO. 29) sequence was mutated to EQSVGA (SEQ ID NO. 31) (for simplicity, the mutant is subsequently referred to as dynL356Q). The addition of LPS to cultured podocytes overexpressing dynL356Q yielded no p40 (FIG. 19G, lane 10). Finally, a GTPase-defective dynamin mutant was examined. Dynamin carrying a mutation in its GAP domain (dynR725A) oligomerizes, but is impaired in assembly-stimulated GTP-hydrolysis. DynR725A is therefore predicted to live longer in the assembled state. Consistent with our model, LPS treatment of cells expressing dynR725A did not generate p40 (FIG. 19G, lane 9).

To determine if dynamin cleavage by CatL occurred in the cytoplasm, subcellular fractionation experiments were performed. As shown in FIG. 19E, p40 was detected only in the supernatant fractions (lane 1, panel GTPase). In addition, while N-terminal p40 seems to exist as a stable intermediate, the predicted 60 kD C-terminal fragment resulting from CatL cleavage was undetectable (FIG. 19E, panel GAP, lane 1), and thus may be degraded. As shown previously, overexpressed full-length dynamin, like the endogenous protein, is equally distributed between the particulate and the soluble fractions (FIG. 19E, lanes 1 and 2, top two panels), probably because the protein exists in cytosolic and membrane associated pools. Together, these data suggest that CatL specifically targets the GTP-bound form of dynamin in the cytoplasm by recognizing an evolutionarily conserved ELSGGA motif, and that dynamin self-assembly into higher order structures such as rings or spirals inhibits CatL cleavage.

Dynamin is Cleaved by CatL During Proteinuric Kidney Disease.

Figure 20A:
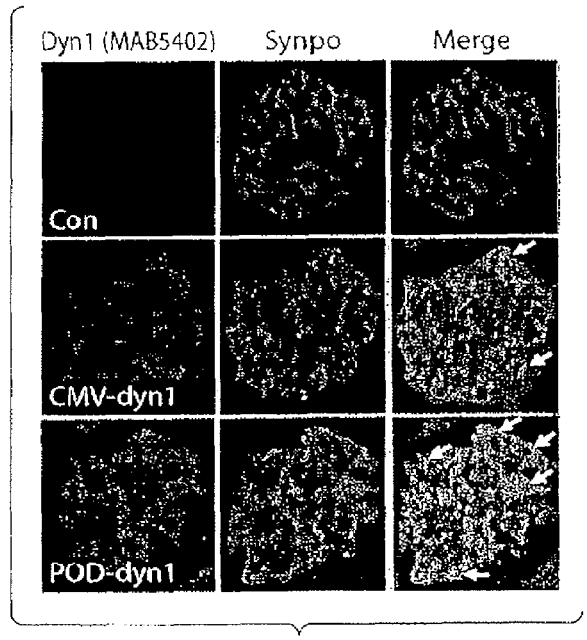
FIG. 20 is a panel of immunostaining images (A,D) and Western blots (B,C) that show CatL cleaves dynamin in kidneys. A) Double-immunofluorescence of dynamin (MAB5402 antibody) and the podocyte marker synaptopodin. Mice were either injected with CMV or podocin driven dynamin vectors. B) Western blot analysis of kidney extracts after gene delivery of dynamin mutants using N-terminal GTPase antibody before and after LPS. C) Western blot analysis of CatL−/− kidney extracts after gene delivery of dynWT before and after LPS. D) Immunocytochemistry of glomeruli from mice that were injected with LPS. 24 h after LPS injections animals received cDNA expressing dynWT, dynL356Q (SEQ ID NO. 3) and dynR725A (SEQ ID NO. 4), and were sacrificed 10 h later. Glomeruli were stained using monoclonal anti-dynamin hudy 1 antibodies.
Figure 25A:
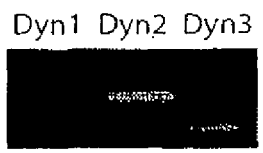
FIG. 25 is a panel of an electrophoresis image (A), a Western blot (B), a bar graph (C), an immunoblot (D), and electron micrographs (E, F), further illustrating the invention. A) RT-PCR of dynamin in podocytes. For total RNA isolation, differentiated podocytes were harvested and lysed in Trizol reagent. RT was performed using oligo-dT primer and Superscript™ II reverse transcriptase (Invitrogen, Carlsbad, Calif.). PCR was done with DNA Taq polymerase (Qiagen, Germantown, Md.). The primer pairs used for amplifying dynamin isoforms were as follows.
Figure 25B:
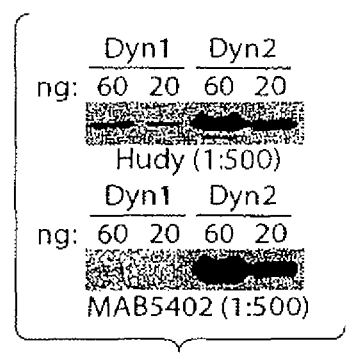
Figure 25C:
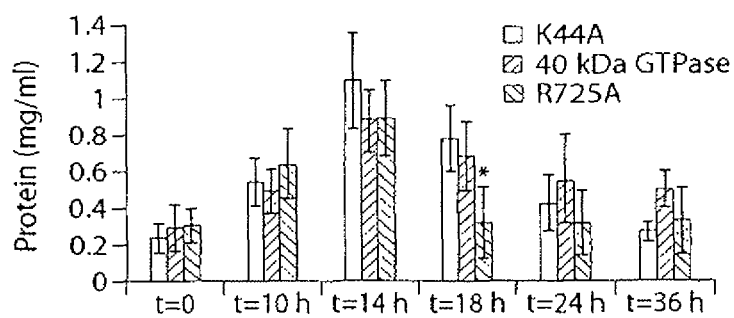
Figure 25D:
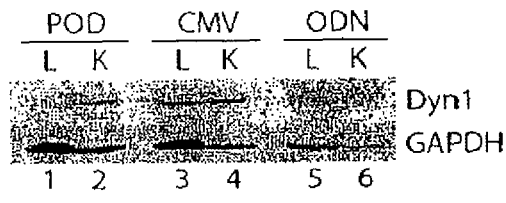
Figure 25E:
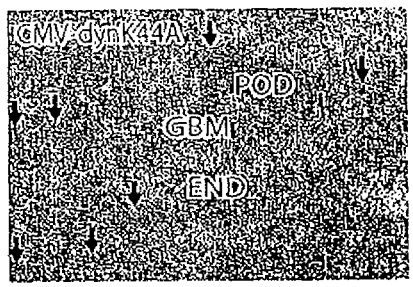
Figure 25F:
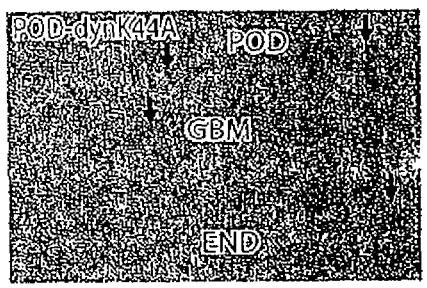

To further examine the possibility that dynamin is cleaved by cytoplasmic CatL during proteinuric kidney disease, dynamin cleavage in kidney extracts from mice before and after LPS treatment was studied. Since the GTPase antibody, which recognizes p40, was not sufficiently sensitive to detect endogenous dynamin cleavage fragments, dynamin was expressed in podocytes using a gene delivery protocol which involves tail vein injection of DNA. Dyn1 was delivered because overexpression of dyn2 can induce apoptosis. RT-PCR showed that podocytes normally express dyn2 (ubiquitous form) and dyn3 (predominantly expressed in testis), but no dyn1 (neuronal isoform, FIG. 25A). Dyn1 was expressed from a CMV promoter (CMV-dyn), or a podocin-specific promoter (POD-dyn). Gene delivered dyn1 was distinguished from endogenous dyn2 using the monoclonal dynamin antibody MAB-5402, which predominantly recognizes dyn1 (FIG. 25B). As shown in FIG. 20A, MAB-5402 antibodies exhibited very weak staining of endogenous dyn2 in the glomerulus. In contrast, 12 hours after gene delivery of CMV-dyn1, dyn1 was detected in virtually all resident cell types of the glomerulus including podocytes, as seen by partial co-localization with synaptopodin (Mundel et al., 1997) (FIG. 20A, CMV-dyn1). Dyn1 was also detected in glomerular endothelial and mesangial cells, in parietal epithelial cells as well as in a few kidney tubular structures (data not shown). The gene delivery of POD-dyn1 led to strong expression of dyn1 specifically in podocytes, as demonstrated by colocalization with synaptopodin (FIG. 20A, POD-dyn1, white arrows). The presence of dyn1 in FPs of podocytes was further confirmed using electron microscopy (FIGS. 25E and 25F) Immunoblot analysis identified dyn1 in liver and kidney extracts when dynamin was expressed from the CMV promoter (FIG. 25D, lanes 3 and 4), whereas POD-dyn1 yielded expression in kidney but not liver (FIG. 25D, compare lanes 1 and 2). Interestingly, there was almost identical expression of dynamin in kidney cytosols isolated from animals injected with CMV-dyn1 or POD-dyn1 (FIG. 25D, compare lanes 2 and 4), suggesting that podocytes preferentially take up injected DNA. Together, these data demonstrate that dynamin can be efficiently expressed in podocytes of mice using transient gene-delivery.

Figure 20B:
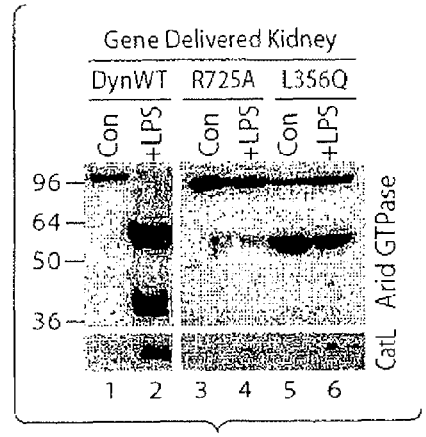
Figure 20C:
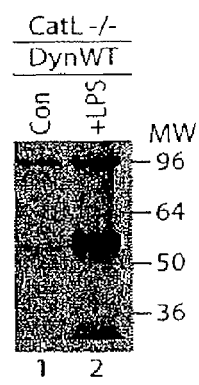
Figure 20D:
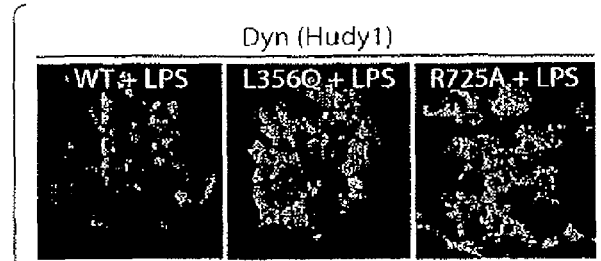

Next the cleavage pattern of dyn1 in kidney extracts following LPS injection was examined. Kidney cytosols were probed with antibody against the GTPase domain of dynamin, which detects p40. Injection of LPS into mice at the time of gene delivery using dynWT caused induction of CatL expression and proteolytic cleavage of dyn1 in kidney extracts with generation of p40 (FIG. 20B, lane 2). Generation of p40 required the presence of CatL, since it was not detected in CatL-/- mice injected with LPS (FIG. 20C, lane 2), and this fragment was not generated in animals that were injected with dynL366Q (FIG. 20B, lane 6). In addition, expression of dynR725A also did not result in generation of p40 (FIG. 20B, lane 4), which is consistent with the data already presented on cultured podocytes (FIG. 19G). Western blotting also detected a dynamin fragment of ~55 kD. As in cultured podocytes, the presence of this fragment was LPS- and CatL-independent (FIG. 20B, lane 5 and 20C, lanes 1 and 2), further supporting the idea that it is generated by other proteases during tissue preparation. Finally, dynL356Q and dynR725A showed normal staining in LPS-treated kidney glomeruli (FIG. 20D), in contrast with the loss of staining observed for dynWT (FIG. 20D, WT panel). In summary, CatL-dependent generation of p40 in mouse kidneys after addition of LPS is consistent with data obtained in cultured podocytes, and further supports a model in which the cytoplasmic short form of CatL cleaves dynamin during proteinuria.

Dynamin is Required for Normal Glomerular Function.

Figure 21A:
FIG. 21 is a panel of electron micrographs (A-C) and bar graphs (D-F) that show the effects of dynamin mutants on podocyte structure and function. A, B, C) Electron micrographs of glomeruli in control mice (A), after injection of POD-dynK44A (B) and after LPS injection (C). D, E, F) Urinary protein levels determined using standard Bradford protein assay. (D) Urine was collected immediately before, 14 h after and 24 h after injection of podocin-driven dynamin vectors. (E) Mice were injected with DNA or delivery solution, followed immediately by a single dose of LPS. Proteinuria was assessed 10, 24, and 48 h after injections. (F) Mice were injected at 0 h and 24 h with LPS. At 48 h, mice were injected with DNA or delivery solution. At 58 h, proteinuria was assessed. Each data point represents at least 10 animals. Pod: podocin-driven dynamin vectors.
Figure 21B:
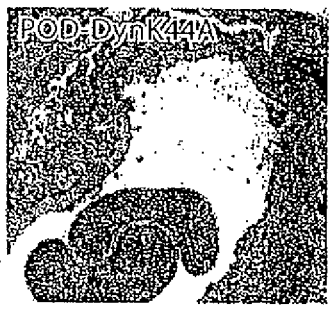
Figure 21C:
Figure 21D:
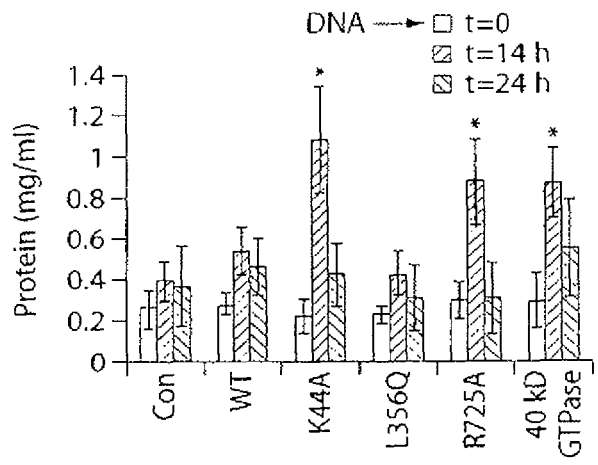

To explore whether functional dynamin is required for the maintenance of FP morphology in healthy kidneys, it was examined whether expression of dominant negative dynK44A disrupts podocyte function. In healthy mice, expression of dynWT using the podocin promoter did not cause changes in FP architecture (data not shown), or a significant increase in urinary protein (FIG. 21D and Table 5). The same was true for expression of dynL356Q (FIG. 21 and Table 5), suggesting that cleavage of dynamin by CatL is not essential for normal kidney morphology. These data are also in agreement with a normal FP architecture in CatL-/- mice (data not shown), and CatL-/- podocytes. In contrast, podocin driven expression of dynK44A, the dynamin mutant that cannot bind GTP, caused FP effacement (FIG. 21B) and proteinuria (1.1±0.26 mg/ml) at the peak of gene expression 14 hours after gene delivery (FIGS. 21D and 25C). Interestingly, expression of dynR725A, a dynamin mutant that is impaired in GTP-hydrolysis and is therefore predicted to live longer in the GTP-bound state (Sever et al., 1999), resulted in partial FP effacement (data not shown) and an intermediate increase in proteinuria (0.88±0.21 mg/ml) (FIG. 6D). In classical models of GTPases, the GTP-bound form represents the active conformation, thus the results with dynR725A suggest that hyperactive dynamin might be deleterious for kidney function. In other words, tight regulation of the life-time of the GTP-bound form of dynamin appears to be required for normal FP morphology and ultrafiltration.

DynL356Q and dynR725A Protect Against FP Effacement and Proteinuria.

Figure 21E:
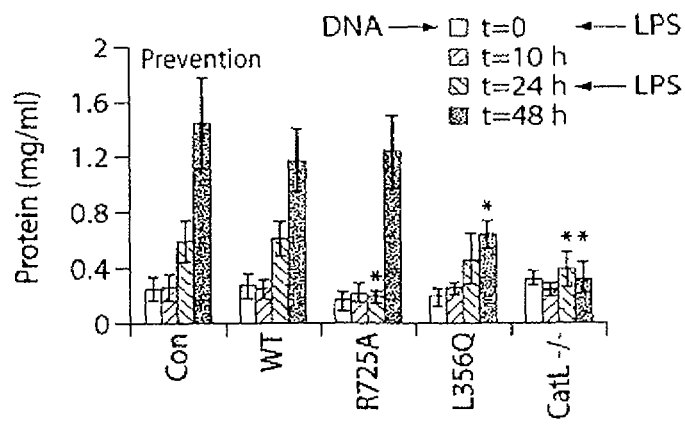

If dynamin is a target of CatL, then dynL356Q and dynR725A, which are resistant to CatL cleavage, might protect kidneys from LPS. In control mice, two injections of LPS led to FP effacement (FIG. 21C) and a large increase in proteinuria (FIG. 21E, Con). Gene delivery of dynWT immediately before LPS injection did not protect against these changes. In contrast, delivery of dynL356Q reduced proteinuria by ~50% (FIG. 21E. Strikingly, delivery of dynR725A completely inhibited development of proteinuria after 24 hours (FIG. 21E). The decline of dynR725A expression in podocytes (data not shown and FIG. 25C) was then associated with the development of proteinuria at 48 hours, after the second injection of LPS.

Figure 21F:
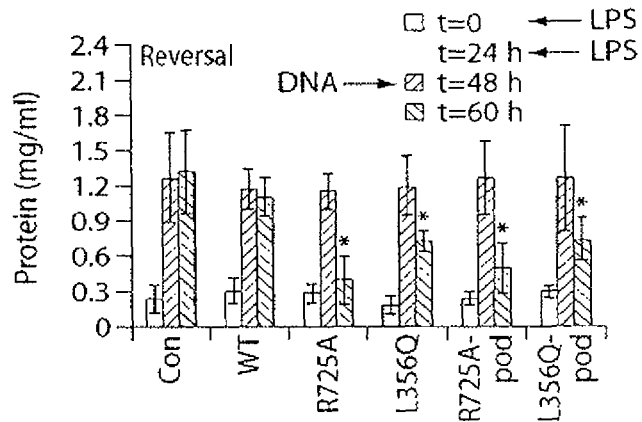

Nest it was examined whether dynL356Q and dynR725A can reverse already established proteinuria. LPS was injected into mice at 0 and 24 hours. At the peak of proteinuria at 48 hours, mice were injected with dynWT, dynL356Q, or dynR725A, and the degree of proteinuria was analyzed 12 hours post injection. While expression of dynWT did not reduce proteinuria, expression of dynL356Q reduced proteinuria by ~50% (FIG. 21F, 60 hours). Strikingly, expression of dynR725A led to almost complete reversal of proteinuria (FIG. 21F). The rescue could be achieved with both podocin and CMV-driven protein expression. These data suggest that both dynamin mutants protect from LPS-induced FP effacement but that dynR725A provides more powerful protection, most likely due to restoration of optimal cellular levels of dynamin:GTP.

CatL Cleavage of Dynamin Generates a Fragment with Dominant Negative Characteristics.

Figure 18G:
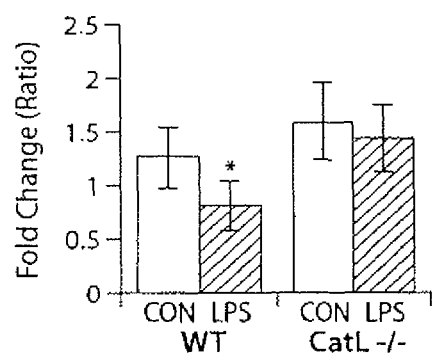

The inability of dynWT to protect or reverse proteinuria although it was overexpressed above endogenous levels was puzzling. Furthermore, Western blot analysis showed that loss of endogenous dynamin upon LPS treatment of podocytes was ~30% (FIG. 18G). Together, these data suggest that (1) only a fraction of dynamin is active and this pool is specifically targeted by dynamin and/or that (2) CatL cleavage of dynamin generates a dominant negative species of dynamin, likely to be p40, that inhibits podocyte function. To test the latter possibility, p40 was expressed in mouse kidneys using podocin driven constructs. As shown in FIG. 21D, expression of p40 resulted in increased urinary protein levels (0.87±0.17 mg/ml). These data show that generation of p40 is harmful for podoctyes, suggesting that CatL not only decreases the amount of functional dynamin, but also generates a dominant negative fragment.

Dynamin:GTP Regulates Actin Dynamics in Podocytes.

Figure 22A:
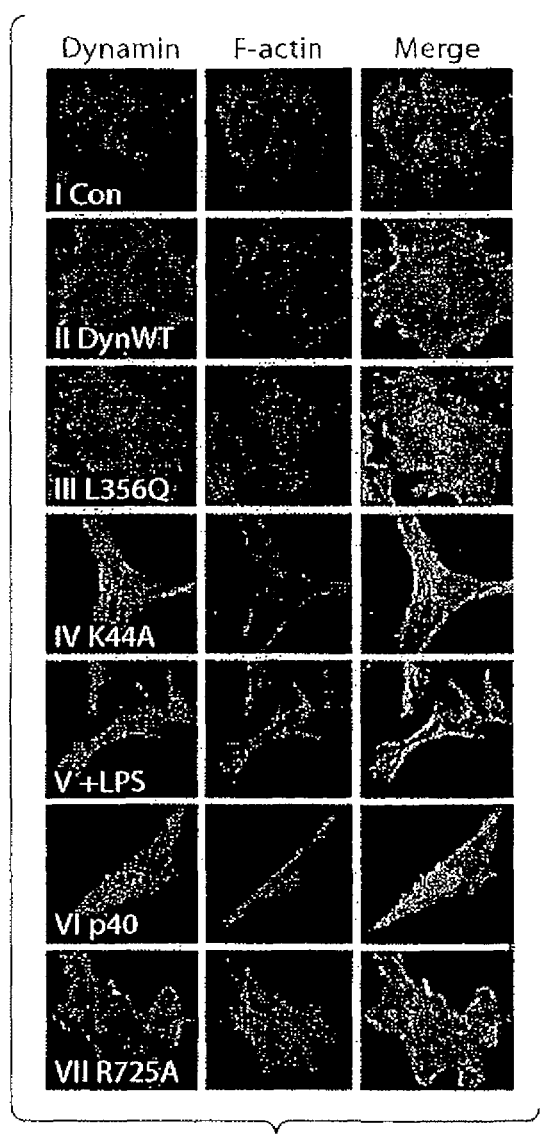
FIG. 22 is a panel of immunostaining images (A, C) and a bar graph (B) that show the GTPase activity of dynamin regulates actin organization and podocyte motility independently of endocytosis. A) GTP-binding by dynamin is required for formation of actin stress fibers in cultured podocytes. Cultured podocytes were infected with adenoviruses expressing the indicated dynamins constructs. 18 h after infection, cells were stained with hudy 1 to stain for dynamin, and rhodamine phalloidin to visualize F-actin. B) Effects of dynamin on podocyte migration using a modified Boyden chamber assay. C) Effects of dynamin mutants on the podocyte actin cytoskeleton during LPS exposure.
Figure 22B:
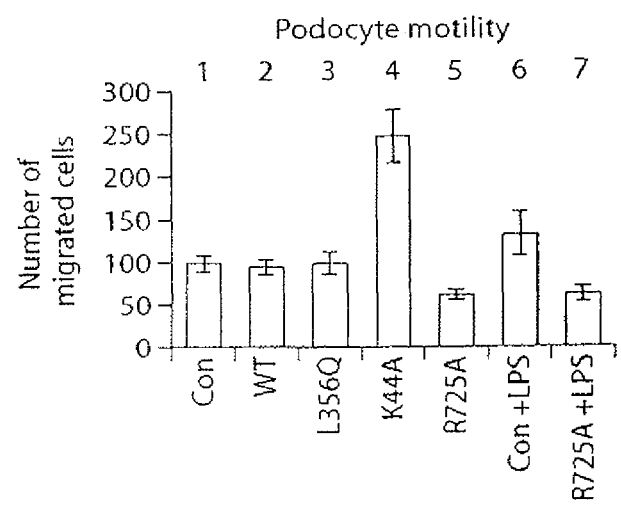

Since podocyte FP effacement is primarily driven by the rearrangement of the actin cytoskeleton (Asanuma et al., 2006), we next examined actin morphology in cultured podocytes expressing different dynamin mutants. Podocytes were infected with various dynamin constructs using an adenoviral expression system that enables greater than 90% efficiency of infection. The experiments were performed using dyn1 (FIG. 22) as well as dyn2, with identical results (data not shown). As shown in FIG. 22A, podocyte actin is organized in parallel bundles of stress fibers and a cortical ring of filamentous actin (row I). Expression of dynWT or dynL356Q did not significantly alter the F-actin staining pattern (compare rows II and III with I), or change significantly the motility of podocytes (FIG. 22B, columns 2 and 3, respectively), which is a functional read-out of actin dynamics. In contrast, the expression of dynK44A (which does not bind GTP) abolished stress fibers while enhancing the cortical actin web (row IV), causing a profound change in cell morphology towards a polygonal shape, as well as dramatically increased motility (FIG. 22B, column 4). A similar actin and cell morphology phenotype was associated with PAN and LPS treatments (FIG. 22A, row V), which also increased cell motility (FIG. 22B, column 6). Finally, expression of p40 in mice causes proteinuria (FIG. 21D), and loss of stress fibers in podocytes (FIG. 22A, row VI). Thus, treatments which abolish actin stress fibers in cultured podocytes cause proteinuria in mice. Strikingly, expression of dynR725A had the opposite effect of dynK44A and LPS, decreasing cortical actin and inducing stress fibers, some of which resembled thin cable-like filament bundles (FIG. 22A, row VII), and decreasing motility (FIG. 22B, column 5). When delivered into healthy mice, dynR725A also induced proteinuria. These observations suggest that a proper balance between cortical actin and actin stress fibers in podocytes is essential to maintain normal kidney function. Consistent with this notion, the deleterious effects of LPS (which reduces stress fibers) on kidney function were ameliorated by expression of dynR725A (which induces stress fibers).

Figure 22C:
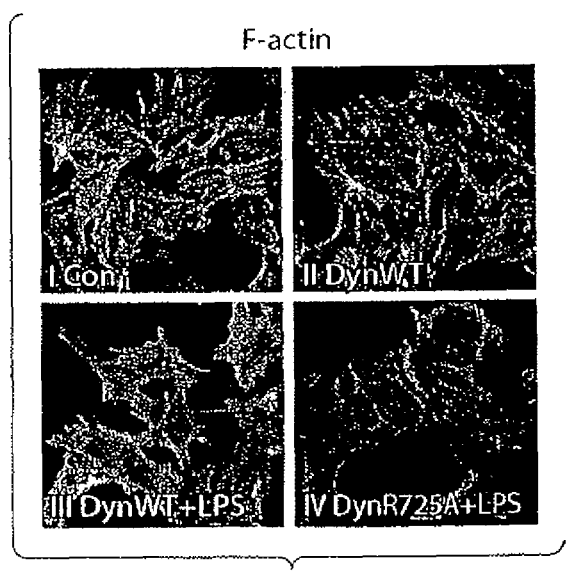

To test more directly whether dynR725A protects against LPS through an effect on actin dynamics, cultured podocytes were treated with LPS in the presence of dynWT or dynR725A. In contrast to dynWT, dynR725A inhibited the ability of LPS to reduce stress fibers and to increase cortical actin (FIG. 22C, panel IV). Consistent with this observation, dynR725A also blocked the LPS-induced increase in podocyte motility (FIG. 22B, column 7). Preservation of stress-fibers was also observed in cells expressing dynL356Q treated with LPS, but to a less dramatic extent than dynR725A (data not shown). Thus, preservation of stress fibers in cells can account for the observed protection/reversal of proteinuria in the LPS model. The inability of dynWT to protect from LPS-induced changes in actin dynamics, although only a small fraction of overexpressed dynWT was cleaved by CatL, could be explained by the generation of p40 by cytoplasmic CatL (FIG. 19G, lane 7). Together, these data suggest that protection of dynamin from CatL cleavage maintains a functional podocyte actin cytoskeleton.

The effects of dynamin mutants on actin could be due to a direct connection between these proteins, an indirect consequence of changes in clathrin-mediated endocytosis, or both. While at present there is no direct evidence for a direct connection between actin and dynamin, several lines of evidence suggest that inhibition of endocytosis by itself is not sufficient to explain the effects. First, LPS treatment dramatically changed actin morphology (FIG. 22A, row VI) and motility (FIG. 22B, column 6), but it did not alter R-Tfn internalization (FIG. 26A, Panel II). Second, expression of a known endocytosis inhibitor, dominant-negative auxilinH875Q impaired endocytosis to the same extend as dynK44A (FIG. 26, compare panels IV and VIII), yet it did not alter actin morphology or podocyte motility (FIG. 26B, and data not shown). Third, while expression of dynR725A increased stress fibers, the level of endocytosis was at wild type levels, as shown previously. Thus, the ability of dynR725A to increase proteinuria in mice could not be explained by the inhibition of endocytosis. In sum, there was no correlation between levels of endocytosis and actin dynamics in podocytes, raising the possibility that dynamin mutants might affect podocyte actin dynamics directly.

TABLE 5

Protein in mice urine determined by standard Bradford assay

| Experiments | Protein in the urine (mg/ml) | | |
|---|---|---|---|
| Basic Phenotype | t = 0 | t = 14 h | t = 24 h |
| Control (podo vector) | 0.26 ± 0.09 | 0.40 ± 0.10 ($1.9 \times 10^{-2}$) | 0.37 ± 0.20 |
| WT (podo) | 0.28 ± 0.06 | 0.54 ± 0.13 ($4.2 \times 10^{-3}$) | 0.46 ± 0.16 ($4.6 \times 10^{-2}$) |
| K44A (podo) | 0.24 ± 0.08 | 1.09 ± 0.27 ($3.0 \times 10^{-5}$) | 0.42 ± 0.16 ($5.2 \times 10^{-3}$) |
| R725A (podo) | 0.29 ± 0.10 | 0.79 ± 0.22 ($4.4 \times 10^{-5}$) | 0.45 ± 0.18 ($3.6 \times 10^{-2}$) |
| L356Q (podo) | 0.24 ± 0.05 | 0.45 ± 0.12 ($2.5 \times 10^{-3}$) | 0.35 ± 0.018 |
| P40 (podo) | 0.33 ± 0.14 | 0.87 ± 0.18 ($9.2 \times 10^{-6}$) | 0.52 ± 0.027 |
| Prevention | t = 0 | t = 24 h | t = 48 h |
| 2 × LPS control | 0.26 ± 0.09 | 0.60 ± 0.15 ($2.6 \times 10^{-4}$) | 1.46 ± 0.36 ($1.9 \times 10^{-6}$) |
| WT (CMV) + 2 × LPS | 0.28 ± 0.07 | 0.63 ± 0.12 ($1.3.2 \times 10^{-3}$) | 1.18 ± 0.23 ($7.6 \times 10^{-5}$) |
| R725A (CMV) + 2 × LPS | 0.17 ± 0.08 | 0.20 ± 0.05 | 1.25 ± 0.29 ($5.0 \times 10^{-6}$) |
| L356Q (CMV) + 2 × LPS | 0.21 ± 0.06 | 0.47 ± 0.19 ($9.0 \times 10^{-3}$) | 0.65 ± 0.10 ($3.9 \times 10^{-6}$) |
| CatL −/− mice | 0.34 ± 0.11 | 0.40 ± 0.16 | 0.34 ± 0.013 |
| Reversal | t = 0 | t = 48 h | t = 58 h |
| 2 × LPS control | 0.24 ± 0.11 | 1.26 ± 0.39 | 1.32 ± 0.37 |
| 2 × LPS + WT(CMV) | 0.30 ± 0.11 | 0.17 ± 0.20 | 1.10 ± 0.18 |
| 2 × LPS + R725A (CMV) | 0.28 ± 0.10 | 1.15 ± 0.17 | 0.38 ± 0.23 ($1.8 \times 10^{-3}$) |
| 2 × LPS + L356Q (CMV) | 0.18 ± 0.08 | 1.20 ± 0.28 | 0.71 ± 0.09 ($1.5 \times 10^{-4}$) |
| 2 × LPS + R725A (podo) | 0.23 ± 0.07 | 1.26 ± 0.34 | 0.49 ± 0.23 ($1.6 \times 10^{-4}$) |
| 2 × LPS + L356Q (podo) | 0.29 ± 0.05 | 1.36 ± 0.49 | 0.73 ± 0.29 ($6.9 \times 10^{-3}$) |

Number of mice per each experimental data set was at least 10. Numbers in parentheses show 'p' values generated by two-tailed t-test, where the changes are relative to 48 h data for the values reported in the 'reversal' part and relative to t = 0 data for all others.
The statistically significant values (where p < 0.05) are printed in bold.

Experimental Procedures

Cells, Antibodies, Reagents and Standard Techniques.

Conditionally immortalized mouse podocyte cell lines were grown as described previously (Mundel et al., Exp Cell Res 236; 248-258; (1997)). Dynamin antibodies: Anti-dynamin (hudy 1) monoclonal antibody was purchased from Upstate Technology (Lake Placid, N.Y.); mouse anti-dyn1 monoclonal antibody (MAB 5402) was from Chemicon (Temecula, Calif.); mouse anti-dyn1 monoclonal antibody (VAM-SVO41) was from StressGene (Victoria, Canada). The rabbit antiserum against mouse CatL was used as described (Ishidoh and Kominami, 1994). For immunogold and immunocytochemistry analysis of CatL, we used a rabbit polyclonal antibody against CatL as described before (Ahn et al., Traffic 3, 147-159 (2002)). CatL−/− fibroblasts were maintained as described previously (Hsieh et al., J Immunol 168, 2618-2625 (2002)). Stable CatL knock-down cell lines were generated with a vector-based siRNA directed against CatL (target sequence 5'-GTGGACTGTTCTCACGCT-3; SEQ ID NO. 32). Quantitative PCR was performed on a Applied Biosystems 7300 Real-Time PCR System. Fold-expression changes were calculated using the comparative $C_T$ method for relative quantitation with the equation $2^{-\Delta\Delta CT}$. Protein expression levels for dynamin and CatL were calculated using densitometric analysis with Kodak imaging software. Statistical significance was assessed with the unpaired t-test with Welch's correction. Transfections with CatL constructs were performed using Lipofectamine 2000 (Invitrogen) following manufacturer's instructions Immunocytochemical analysis of cultured podocytes was done as described (Reiser et al., J Biol Chem 279, 34827-34832 (2004)). Immunoperoxidase labeling of human tissue was done on formalin fixed kidney biopsies embedded in paraffin. Transmission electron microscopy (TEM) and immunoelectron microscopy (IEM) were performed as described (Regele et al., J Am Soc Nephrol 11, 403-412 (2000)). Subcellular fractionation of cultured cells was performed as described (Damke et al., J Cell Biol 127, 915-934 (1994)). Internalization of rhodamine-transferrin (R-Tfn) was performed using 20 μg/ml R-Tfn in PBS containing 1 mM CaCl$_2$, 1 mM MgCl$_2$, 5 mM glucose, and 0.2% BSA for 10 min at 37° C.

Animals and Treatments.

All animal studies were approved by the MGH Subcommittee for Research Animal Care. C57BL6 mice were obtained from Jackson Laboratory (Bar Harbor, Me.). CatL−/− mice are in a pure C57BL6 background (Nakagawa et al., Science 280, 450-453 (1998)). LPS induced mouse proteinuria model was utilized as previously described (Reiser et al., J Clin Invest 113, 1390-1397 (2004)). Rat PAN nephrosis model was induced by a single intravenous injection of PAN (180 mg/kg body wt; Sigma-Aldrich, St. Louis, Mo.) (Kim et al., Am J Physiol Renal Physiol 286, F922-935 (2004)).

Patients and quantitative glomerular RT-PCR. Microdissected glomeruli from patients with proteinuric diseases and from control subjects were analyzed. For control biopsies, renal tissue was derived from pre-transplantation kidney biopsies during cold ischemia time from 7 living and 1 cadaveric donors (n=8) (Schmid et al., J Am Soc Nephrol 14, 2958-2966 (2003)). Statistical analysis was performed using the Kruskal-Wallis-Test and Mann-Whitney-Test.

Processing of Dynamin by CatL In Vitro.

Recombinant dynamin was purified as described (Damke et al., 2001). 1 μg of dynamin (10 pmol) was diluted in buffer containing 200 mM NaCl, 10 mM HEPES pH 7.0, 2 mM EGTA, 1 mM MgCl$_2$ and 1 mM DTT. When indicated 200 μM of GTP or 1 mM of GTP$_\gamma$S was added, and dynamin was allowed to bind nucleotides for 10 min on ice. Reaction was initiated by addition of 0.5 μl of purified CatL (S.A. 4.13 units/mg of protein from Sigma, Saint Louis, Mo.), and samples were placed at 37° C. in the water bath for 10 min. Total assay volume was 20 μl. Reaction was terminated with addition of E-64d inhibitor (Sigma, Saint Louis, Mo.), and sample buffer. For Western blot analysis 5 μl of the samples was run on 10% SDS-PAGE. When CatB (S.A. 3 units/mg of protein from Sigma, Saint Louis, Mo.) or recombinant human furin (from R&D Systems, Minneapolis, Minn.) were used, 2 µl of the enzymes were added in the assay.

Adenoviral Infections of Cultured Podocytes.

Podocytes were grown under non-permissive conditions to 70% confluence. Cells were washed twice with 1×PBS and infected with 1.2 ml of serum-free DMEM media containing 100 µl transactivator virus, 100 µl virus expressing dyn1 or dyn2. After 2 h of infection at 37° C., media containing virus was replaced with full DMEM. If cells were treated with LPS or PAN, 50 µg/ml of LPS or 50 µg/ml PAN was added at this point. 18-24 h post-infection, cells were detached using trypsin and processed either for subcellular fractionation or tested in the motility assays as described in (Reiser et al., J Biol Chem 279, 34827-34832 (2004)). When stated, 20 µM of Z-FF-FMK CatL specific inhibitor (Calbiochem, San Diego, Calif.) was added simultaneously with addition of LPS.

Kidney Extracts.

Four mice kidneys were homogenized in buffer containing 20 mM HEPES pH 7.5, 100 mM NaCl, 1 mM $MgCl_2$, 1 mM PMSF, proteinase inhibitors, calpain inhibitor (Calbiochem, San Diego, Calif.) and E-64d using dounce homogenizer. Subsequently, cytosol was centrifuged for 10 min at 7000 rpm. Proteins were solubilized by 1% Triton X, 1 h at 4° C., before it was spun at 50,000 rpm for 1 h.

In Vivo Gene Delivery.

CatL plasmids encoding short and long CatL (Goulet et al., Biol Chem 387, 1285-1293 (2004)), Dyn1 plasmids (pcDNA-driven) or p2.5 Podocin-driven (Moeller et al., Genesis 35, 39-42 (2003)) were introduced into mice (n>10, each construct) using the TransIT in vivo gene delivery system according to the manufacturer's instruction (Mirus Bio Corporation, Madison, Wis.). 10 and 24 h after gene delivery, proteinuria was assessed by Multistix 8 SG strips (Bayer Corporation, Elkhart, Ind.) (data not shown), and Bradford protein assay (Sigma, Saint Louis, Mo.). From the same urines the protein/creatinine ratio was determined with Albuwell M and Creatinine Companion protein/creatinine ELISA kits (Exocell Inc., Philadelphia, Pa.), (data not shown).

Example 5

Dominant-Activating Dynamin Mutants Act as Suppressor of Metastasis

Dynamin was recently identified as being synthetically lethal with Drosphila abnormal wing discs (awd). Interestingly, awd encodes nucleoside diphosphate kinase (NDK), which is required for synthesis of GTP. Since levels of dynamin:GTP determine the rate of endocytosis, the synthetic lethality with dynamin suggests that NDK-dependent supply of GTP might help determine the rate of endocytosis; in other words NDK regulated level of GTP will determine the amount of dynamin:GTP. Importantly, awd is the *Drosophila* ortholog of a human gene nm3, which is the first metastasis suppressor gene identified. Reduced expression of Nm23 protein appears to be a primary determinant of tumor progression, invasiveness, and serum-stimulated motility of several metastatic tumors including breast tumors. In light of these novel findings, an early effect of nm23-mediated metastatic processes is due to slowing down dynamin-dependant endocytosis by lowering the levels of GTP inside the cell. Point mutations in dynamin's GAP domain, have been generated which slow down GTP-hydrolysis by dynamin, and thus prolog the lifetime of dynamin:GTP. Expression of these mutants in the HeLa cells potently activates endocytosis. These mutants represent the first experimental manipulation that has ever effected a stimulation of endocytosis. The dynamin mutants are used to suppress metastasis due to low levels of Nm23. Transgenic mice expressing dominant-activating dynamin mutants are generated to examine whether increased level of endocytosis can protect against breast cancers induced by different oncogenes, or their metastatic potential.

This study takes advantage of our tetracycline (tet) regulatable adenoviruses that express $dyn^{K694A}$. $Dyn^{K694A}$ is impaired in dynamin self-assembly, and therefore assembly-stimulated GTP-hydrolysis, and its expression in HeLa cells potently increases the rate of endocytosis, which leads to downregulation of the number of receptors at the cell surface. Adenoviruses can be co-transfected with adenovirus expressing a chimeric tetracycline-regulatable transcription activator (tTA), which allows expression of dynamin in variety of different cell lines in tet-controllable manner. Cells infected with the virus grown in the presence of tetracycline, which inhibits protein expression, will be used as a control for viral infection. Thus, dominant-activating $dyn^{K694A}$ is expressed in highly metastatic murine melanoma cells and human breast carcinoma cells both shown to have inversely correlated tumor metastatic potential to the levels of nm23 protein. It has been shown that overexpression of nm23 in those cells suppresses their motility in an in vitro assay, and their metastatic potential in nude mice. Increased levels of dynamin:GTP due to slowing down the hydrolysis counter act the low levels of GTP due to decrease in the level of Nm23 protein. These trends are observed in vitro, as well as in vivo assays as expression of Nm23.

A transgenic mice that will express $dyn^{K694A}$ is generated. As discussed herein mammalian cells express three closely related dynamin isoforms: dynamin-1 is exclusively found in neuronal cells, dynamin-2 is ubiquitously expressed, whereas dynamin-3 is predominantly expressed in testis. Transgenic mice are generated, which express ubiquitous dynamin-2 carrying activating mutation from a tetracycline-responsive promotor, which allows inducible expression of dynamin gene. This strategy permits the creation of transgenic mice in which expression of a reporter gene can be controlled by altering the concentration of tetracycline in the drinking water of the animals. Inducible mRNA and protein are easily detected in cell lines by RNA and Western blotting. Importantly, trans-gene-positive mice maintain expression of gene up to 3.5 months in the absence of tetracycline. Given that dynamin is essential for endocytosis, the ability to temporally control dynamin expression in transgenic mice is essential to obtain live animals. Plasmids carrying autoregulatory plasmid pTet-tTAk and pTet-Splice for cloning of dynamin gene can be obtained from Professor David G. Schatz (Yale University School of Medicine, New Haven, Conn.).

Once transgenic mice are obtained they are crossed with four different strains of breast-cancer-prone mouse mammary tumor virus (MMTV)-oncogene transgenic mice to examine whether increased level of endocytosis can protect against breast cancers induced by different oncogenes, or their metastatic potential. For these studies strains overexpressing the oncogenes v-Ha-ras, c-neu, c-myc and Wnt-1 are used. MMTV-v-Ha-ras, MMTV-c-neu and MMTV-c-myc mice are purchased from the Charles River Laboratories, and MMVT-Wnt-1 mice are purchased from the Jackson Laboratory. Transgenic mice are also generated for the neuronal specific dynamin-1 isoform as well as for testis specific dynamin-3 isoform.

All patents, publications and references cited herein are hereby fully incorporated by reference. In case of conflict between the present disclosure and incorporated patents, publications and references, the present disclosure should control.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for treating kidney disease comprising administering to a patient in a need thereof an effective amount of a thiol alkylating agent for treating the kidney disease.

2. The method of claim 1, wherein the administering of the thiol alkylating agent results in the formation of actin stress fibers in podocytes.

3. The method of claim 1, wherein the administering of the thiol alkylating agent results in multimeric dynamin structures.

4. The method of claim 1, wherein the thiol alkylating agent is a maleimide.

* * * * *